United States Patent
Tang et al.

(10) Patent No.: US 10,612,040 B2
(45) Date of Patent: Apr. 7, 2020

(54) FERTILITY GENE AND USE THEREOF

(71) Applicants: SHENZHEN INSTITUTE OF MOLECULAR CROP DESIGN, Guangdong (CN); HUNAN WANGHUA AGRICULTURAL BIOTECHNOLOGY CO., LTD, Hunan (CN); SHENZHEN XINGWANG BIOSEED CO., LTD., Guangdong (CN); XINGWANG INVESTMENT CO., LTD., Beijing (CN)

(72) Inventors: Xiaoyan Tang, Guangdong (CN); Zhufeng Chen, Guangdong (CN); Gang Xie, Guangdong (CN); Na Wang, Guangdong (CN); Jiawei Lu, Guangdong (CN); Zaoxia Li, Guangdong (CN)

(73) Assignees: SHENZHEN INSTITUTE OF MOLECULAR CROP DESIGN, Guangdong (CN); HUNAN WANGHUA AGRICULTERAL BIOTECHNOLOGY CO., LTD., Hunan (CN); SHENZHEN XINGWANG BIOSEED CO., LTD., Guangdong (CN); XINGWANG INVESTMENT CO., LTD., Beijing (CN)

(*) Notice: Subject to any disclaimer, the term of this patent is extended or adjusted under 35 U.S.C. 154(b) by 0 days.

(21) Appl. No.: 15/903,977

(22) Filed: Feb. 23, 2018

(65) Prior Publication Data

US 2018/0187209 A1  Jul. 5, 2018

Related U.S. Application Data

(62) Division of application No. 14/439,565, filed as application No. PCT/CN2013/086657 on Nov. 7, 2013, now Pat. No. 9,938,538.

(30) Foreign Application Priority Data

Nov. 9, 2012  (CN) .......................... 2012 1 0445558

(51) Int. Cl.
*A01H 5/00* (2018.01)
*C12N 15/82* (2006.01)

(52) U.S. Cl.
CPC .......... *C12N 15/8289* (2013.01); *A01H 5/00* (2013.01); *C12N 15/823* (2013.01); *C12N 15/8231* (2013.01)

(58) Field of Classification Search
None
See application file for complete search history.

(56) References Cited

U.S. PATENT DOCUMENTS 7,868,149 B2 *  1/2011  Boukharov ..........  C07K 14/415
536/23.1

* cited by examiner

*Primary Examiner* — Phuong T Bui
(74) *Attorney, Agent, or Firm* — Michael X. Ye; Morris, Manning & Martin, LLP

(57) ABSTRACT

The present disclosure relates to an expression vector for restoring male sterility in a plant. The expression vector comprises a regulatory region sequence operably linked to a heterologous nucleotide sequence.

11 Claims, 12 Drawing Sheets

Specification includes a Sequence Listing.

Mutant    Wild-type

Mutant    Wild-type

Mutant    Wild-type

Mutant　　　　　Wild-type

Double exposed stigmas　Single exposed stigma

```
                    10        20        30        40        50        60
             ....|....|....|....|....|....|....|....|....|....|....|....|
HHZ.seq      MAALGRASSSAPVLAAAAAAAVLLSLCLAALSEEQEQLENLRFVRHAQDAPLVSSYNYIV  60
Mutant.seq   MAALGRASSSAPVLAAAAAAAVLLSLCLAALSEEQEQLENLRFVRHAQDAPLVSSYNYIV  60
Nip.seq      MAALGRASSSAPVLAAAA--AVLLSLCLAALSEEQEQLENLRFVRHAQDAPLVSSYNYIV  58

70        80        90       100       110       120
             ....|....|....|....|....|....|....|....|....|....|....|....|
HHZ.seq      IGGGTAGCPLAATLSEHSRVLLLERGGLPYANMSSEQHFTDALADTSPASPAQRFISEDG 120
Mutant.seq   IGGGTAGCPLAATLSEHSRVLLLERGGLPYANMSSEQHFTDALADTSPASPAQRFISEDG 120
Nip.seq      IGGGTAGCPLAATLSEHSRVLLLERGGLPYANMSSEQHFTDALADTSPASPAQRFISEDG 118

130       140       150       160       170       180
             ....|....|....|....|....|....|....|....|....|....|....|....|
HHZ.seq      VVNARARVLGGGSCLNAGFYTRASNEYVRAAGWDARLVNSSYRWVERSLVFRPDVPPWQA 180
Mutant.seq   VVNARARVLGGGSCLNAGFYTRASNEYVRAAGWDARLVNSSYRWVERSLVFRPDVPPWQA 180
Nip.seq      VVNARARVLGGGSCLNAGFYTRASNEYVRASGWDARLVNSSYRWVERSLVFRPDVPPWQA 178

190       200       210       220       230       240
             ....|....|....|....|....|....|....|....|....|....|....|....|
HHZ.seq      ALRDALLEVGVTPDNGFTFDHVTGTKIGGTIFDNSGQRHTAADFLRHARPRGLTVLLYAT 240
Mutant.seq   ALRDALLEVGVTPDNGFTFDHVTGTKIGGTIFDNSGQRHTAADFLRHARPRGLTVLLYAT 240
Nip.seq      ALRDALLEVGVTPDNGFTFDHVTGTKIGGTIFDNSGQRHTAADFLRHARPRGLTVLLYAT 238

250       260       270       280       290       300
             ....|....|....|....|....|....|....|....|....|....|....|....|
HHZ.seq      VSRILFKSQDGVPYPVAYGVVFSDPLGVQHRVYLRDGDKNEVIVSAGTLGSPQLLMLSGV 300
Mutant.seq   VSRILFKSQDGVPYPVAYGVVFSDPLGVQHRVYLRDGDKNEVIVSAGTLGSPQLLMLSGV 300
Nip.seq      VSRILFKSQDGVPYPVAYGVVFSDPLGVQHRVYLRDGDKNEVIVSAGTLGSPQLLMLSGV 298

310       320       330       340       350       360
             ....|....|....|....|....|....|....|....|....|....|....|....|
HHZ.seq      GPQAHLEAHGIEVIVDQPMVGQGVADNPMNSVFIPSPVPVELSLVQVVGITRSGSFIEGV 360
Mutant.seq   GPQAHLEAHGIEVIVDQPMVGQGVADNPMNSVFIPSPVPVELSLVQVVGITRSGSFIEGV 360
Nip.seq      GPQAHLEAHGIEVIVDQPMVGQGVADNPMNSVFIPSPVPVELSLVQVVGITRSGSFIEGV 358

370       380       390       400       410       420
             ....|....|....|....|....|....|....|....|....|....|....|....|
HHZ.seq      SGSEFGMPVSDGALRWARSFGMLSPQTGQLGTLPPKQRTPEALQRAAEAMMRLDRRAFRG 420
Mutant.seq   SGSEFGMPVSDGALRWARSFGMLSPQTGQLGTLPPKQRTPEALQRAAEAMMRLDRRAFRG 420
Nip.seq      SGSEFGMPVSDGALRWARSFGMLSPQTGQLGTLPPKQRTPEALQRAAEAMMRLDRRAFRG 418

430       440       450       460       470       480
             ....|....|....|....|....|....|....|....|....|....|....|....|
HHZ.seq      GFILEKILGPVSSGHVELRTTDPRANPSVTFNYFREAEDLERCVHGIETIERVIQSRAFS 480
Mutant.seq   GFILEKILGPVSSGHVELRTTDPRANPSVTFNYFREAEDLERCVHGIETIERVIQSRAFS 480
Nip.seq      GFILEKILGPVSSGHVELRTTDPRANPSVTFNYFREAEDLERCVHGIETIERVIQSRAFS 478

490       500       510       520       530       540
             ....|....|....|....|....|....|....|....|....|....|....|....|
HHZ.seq      NFTYANASVESIFTDSANFPVNLLPRHVNDSRSPEQYCMDTVMTIWHYHGGCHVGAVVDD 540
Mutant.seq   NFTYANASVESIFTDSANFPVNLLPRHVNDSRSPEQYCMDTVMTIWHYHGGCHVGAVVDD 540
Nip.seq      NFTYANASVESIFTDSANFPVNLLPRHVNDSRSPEQYCMDTVMTIWHYHGGCHVGAVVDD 538

550       560       570       580
             ....|....|....|....|....|....|....|....|...
HHZ.seq      DYRVFGVQGLRVIDSSTFKYSPGTNPQATVMMLGRYMGVKIQSERWKK 588
Mutant.seq   DYRVFGVQGLRVIDSSTFKYSPDTNPQATVMMLGRYMGVKIQSERWKK 588
Nip.seq      DYRVFGVQGLRVIDSSTFKYSPGTNPQATVMMLGRYMGVKIQSERWKK 586
```

Fig. 7

FERTILITY GENE AND USE THEREOF

This application is a Divisional of application Ser. No. 14/439,565, filed Apr. 29, 2015, now U.S. Pat. No. 9,938,538; which is a National Stage Entry of PCT/CN2013/086657, filed Nov. 7, 2013; which claims priority of Chinese Patent Application No. 201210445558.1, filed Nov. 9, 2012. The entirety of the aforementioned applications is incorporated herein by reference.

FIELD

The present disclosure relates to the field of biotechnology, in particular to plant hybrid methods, including the preparation of a sterile line and the production of hybrid seeds, more particularly to a fertility gene FL2, and its mutant and use in hybrid breeding.

BACKGROUND

Hybrid breeding is an effective way of improving the production of crops. Compared to conventional plants, hybrids often exhibit heterosis, and usually have a significantly increased yield, better resistance, and wider adaptability. In addition, hybrid breeding is less time-consuming and has a shorter breeding cycle than conventional breeding. Therefore, hybrid breeding has become a major approach in the breeding of many crops.

An efficient male sterile line is the key factor in hybrid breeding. The male sterile line, which cannot produce effective male gametes is used as a maternal line to be pollinated by a paternal line. The following factors should be considered during the selection and generation of male sterile lines:

1. Hybrid vigor with other lines: the male sterile line can be crossed with other male-fertile lines to produce hybrids with a better combination of traits;
2. The reproduction of the male sterile line: the sterile line can restore fertility to self-maintain under certain conditions;
3. The efficiency of the reproduction and hybrid seed production using the male sterile line: a good sterile line should be easy to cross and lead to efficient hybrid seed production.

Male sterility can be either cytoplasmic or nuclear. Current hybrid rice utilizes the combination of both types of male sterility. Cytoplasmic male sterility (CMS) is caused by mutations in extranuclear genes and shows maternal inheritance. Manifestation of male sterility in CMS lines may be controlled through the interaction between cytoplasmic and nuclear factors. The widely used three-line method in hybrid rice breeding involves a male sterile line, a restorer line and a maintainer line. The three-line method requires specific restorer lines, which are generated through a complex process and greatly limits the utilization of heterosis among different varieties. By contrast, a two-line method utilizes a male sterile line, in which the sterility is controlled by a nuclear gene and the fertility can be restored under specific growing conditions, and therefore combines the restorer line and the maintainer line into one line. Compared with three-line method, two-line method has greatly simplified the hybrid seed production process by eliminating the demand of maintainer lines and significantly expanded the usage of male sterility hybrid breeding. However, there are also constraints in the utilization of two-line hybrid breeding method. The male sterile line need to switch fertility between ON and OFF under different conditions. It has to remain male sterile for hybrid seed production but be fertile to reproduce itself when the conditions change, in order to maintain the sterile system. The widely used male sterile lines in two-line method are mostly photo-thermo-sensitive sterile (PTGMS), and their fertility is influenced by temperature and light. Therefore, the instability of environment may result in the instability of the fertility of sterile lines, leading to either self-breeding and reduced purity of the hybrid seed, thereby increasing the risk of seed production. Furthermore, the methodology used for selection and generation of sterile lines for two-line method is very limited. For example, there are hardly any male sterile lines suitable for two-line method in *Oryza japonica* rice, restricting wide use of rice variety resources.

To bypass the problems existing in the current methods of hybrid rice breeding, such as the stability of the sterile line, the limitation of hybrid variety resources, the complexity in seed production and the high cost of seed production etc., a new hybrid breeding technique that can fully utilize male sterility controlled by recessive nuclear genes to construct stable sterile lines that are not affected by environmental changes to eliminate the potential risk in seed production is under development. Meanwhile, the recessive nuclear sterility gene is suitable for vast majority of crop varieties to improve heterosis utilization. Embodiments of the present disclosure provide a gene regulating plant fertility, the mutation of which results in male sterility and the sterility is stable and not influenced by environment and may be reversed through introduction of the wild-type gene into plants. The gene and the sterile line generated by the gene mutation provide necessary components for a new hybrid breeding system.

SUMMARY

The present disclosure provides a DNA sequence, which has a function of regulating plant fertility, and the DNA sequence is at least one selected from a group consisting of:
  a) nucleotide sequences of SEQ ID NO: 1, 5 or 27,
  b) nucleotide sequences of SEQ ID NO: 10 or 11,
  c) nucleotide sequences of SEQ ID NO: 13 or 14,
  d) nucleotide sequences of SEQ ID NO: 16 or 17,
  e) nucleotide sequences of SEQ ID NO: 19,
  f) nucleotide sequences of SEQ ID NO: 21 or 22,
  g) nucleotide sequences hybridizable with any one of the nucleotide sequences of (a)-(f) under a stringent condition, or
  h) nucleotide sequences complementary to any one of the nucleotide sequences of (a)-(g).

The above-mentioned DNA sequences may encode an amino acid sequence of SEQ ID NO: 2, 6, 8, 12, 15, 18, 20 or 23.

The present disclosure also provides an expression cassette comprising the above-mentioned DNA sequence.

The present disclosure also provides an expression vector comprising the above-mentioned expression cassette.

The present disclosure also provides an engineered bacterium comprising the above-mentioned expression vector.

The present disclosure also provides use of a gene in regulation of plant fertility, and the gene regulating plant fertility comprises a nucleotide sequence selected from a group consisting of:
  a) nucleotide sequences of SEQ ID NO: 1, 5 or 27,
  b) nucleotide sequences of SEQ ID NO: 10 or 11,
  c) nucleotide sequences of SEQ ID NO: 13 or 14,
  d) nucleotide sequences of SEQ ID NO: 16 or 17,
  e) nucleotide sequences of SEQ ID NO: 19, f) nucleotide sequences of SEQ ID NO: 21 or 22, g) nucleotide sequences hybridizable with any one of the nucleotide sequences of (a)-(f) under a stringent condition, or h) nucleotide sequences complementary to any one of the nucleotide sequences of (a)-(g).

Embodiments of the present disclosure also include a method to obtain a male sterile material through mutating the gene regulating plant fertility of SEQ ID NO: 1, 5, 10, 11, 13, 14, 16, 17, 19, 21, 22 or 27.

The term "mutation" used herein comprises substitution, deletion or addition of one or more nucleotide in the DNA sequence of the gene regulating plant fertility.

The present disclosure also provides a method for fertility recovery in the male sterile material by introducing the above-mentioned DNA sequence, with the male sterile material being obtained by a gene mutation of SEQ ID NO: 1, 5, 10, 11, 13, 14, 16, 17, 19, 21, 22 or 27 correspondingly.

The present disclosure also provides use of a mutant material obtained by a mutation of a nucleotide sequence comprising SEQ ID NO: 1, 5, 10, 11, 13, 14, 16, 17, 19, 21, 22 or 27.

The above-mentioned "mutation" may be point mutation, DNA deletion, insertion mutation or gene silence by means of RNAi or site-directed mutagenesis.

Embodiments of the present disclosure provide a method to utilize the above-mentioned material and DNA sequences in breeding, particularly comprising crossing a male sterile plant as a female parent to be crossed with a restorer line to produce a hybrid seed.

The present disclosure also provides a promoter having a characteristic of anther specific expression, comprising a nucleotide sequence of SEQ ID NO: 3 or 9. The present disclosure also includes an expression cassette containing the described promoter, an expression vector containing the described expression cassette, and/or an engineered bacterium that containing the described expression vector.

The present disclosure also provides a method of expressing a target polynucleotide sequence in a plant, comprising:
introducing a DNA construct into the plant, and
the DNA construct comprises:
a promoter comprising a nucleotide sequence of SEQ ID NO: 3 or 9; and
the target nucleotide sequence operably linked to the promoter.

The expression of "target nucleotide sequence" used herein may be a structural gene, a regulator gene, an antisense sequence of the structural gene, an antisense sequence of the regulator gene or microRNA interfering with the expression of an endogenous gene, which is specifically expressed late in pollen development and regulates pollen fertility and pollen germination.

The present disclosure also provides use of the above-described DNA sequence or the promoter in any one of (a) to (d):
(a) breeding of plant varieties or strains;
(b) breeding of plant varieties or strains for enhanced fertility;
(c) breeding of plant varieties or strains for reduced fertility;
(d) breeding of male sterile plant varieties or strains.

The present disclosure also provides a method of maintaining a male sterile plant at a homozygous recessive state, comprising:
(a) providing the first plant being male sterile and being homozygous for the recessive allele of FL2 gene;

(b) generating the second plant being homozygous for the recessive allele of FL2 gene and being hemizygous for a construct by introducing to the first plant the construct, and the construct comprising:
i) the first nucleotide sequence having FL2 nucleotide sequence to recover male fertility of the first plant when expressed in the first plant;
ii) the second nucleotide sequence to inhibit the formation or function of a gamete of male fertility when expressed in the second plant, with the second nucleotide sequence being a pollen inactivation gene ZM-PA; and
(c) fertilizing the first plant with the male gamete of the second plant to maintain an offspring of the first plant in a homozygous state.

BRIEF DESCRIPTION OF THE DRAWINGS

FIG. 6A-C— Alignment of OsFL2 cDNA related sequences, including Huanghuazhan wild-type OsFL2, cDNA of Huanghuazhan mutant OsFL2 and cDNA of Nipponbare wild-type OsFL2. HHZ represents the sequence of Huanghuazhan wild-type OsFL2 (SEQ ID NO: 1), Mutant represents the sequence of Huanghuazhan mutant OsFL2 (SEQ ID NO: 7), Nip represents the sequence of Nipponbare wild-type OsFL2 (SEQ ID NO: 5). The bottom sequence (SEQ ID NO: 43) is a consensus sequence based on the three sequences above it.

FIG. 7—Alignment of OsFL2 related protein sequences, including Huanghuazhan wild-type OsFL2, Huanghuazhan mutant OsFL2 and Nipponbare wild-type OsFL2. HHZ represents the protein sequence of Huanghuazhan wild-type OsFL2 (SEQ ID NO: 2), Mutant represents the protein sequence of Huanghuazhan mutant OsFL2 (SEQ ID NO: 8), Nip represents the protein sequence of Nipponbare wild-type OsFL2 (SEQ ID NO: 6).

DETAILED DESCRIPTION

Figure 1:
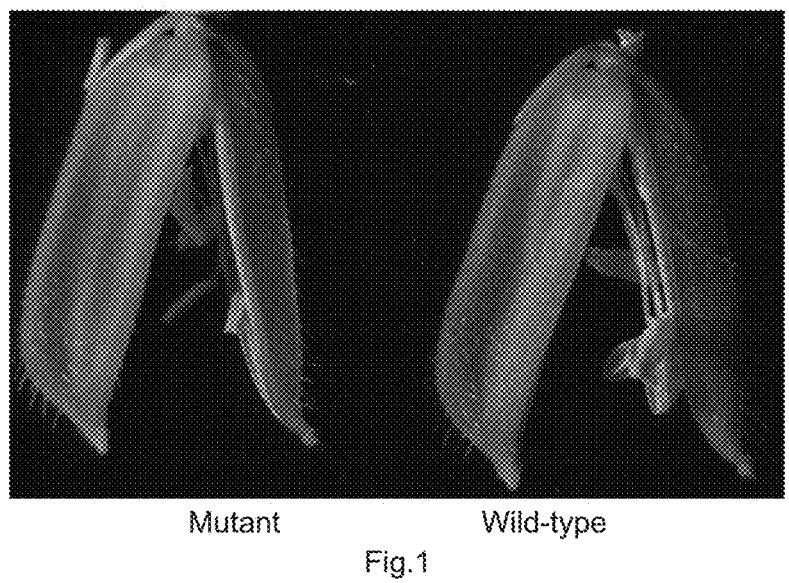
FIG. 1—The floret morphology of Huanghuazhan with mutant OsFL2 or wild-type OsFL2.

All references mentioned herein are incorporated herein by reference.

Unless specifically defined otherwise, all technical and scientific terms used herein have the same meaning as commonly understood by one of ordinary skill in the art to which this invention belongs. Unless defined otherwise, the technologies used or cited in the present disclosure are standard technologies well known by one of ordinary skill in the art to which this invention belongs.

The materials, methods and embodiments described herein are explanatory, illustrative only, which shall not be construed to limit the scope of the present disclosure.

The present disclosure provides a fertility gene, a nucleotide sequence, a protein sequence thereof, and use of the fertility gene in regulation of plant male fertility. By way of non-limiting examples, any method described below may be used together with the corresponding nucleotide sequence of the present disclosure, for example, any method selected from the following may be used: introducing the mutant sequence of the fertility gene into a plant to obtain plant male sterility, mutating a plant endogenous sequence, introducing an antisense sequence of the fertility gene into the plant, utilizing a form of hairpin, ligating the corresponding nucleotide sequence with other nucleotide sequence to regulate a plant phenotype, or any method for influencing the plant male fertility known to persons skilled in the art.

The fertility gene FL2 provided herein is a gene involved in pollen development. The fertility gene FL2 locates in chromosome 10 of the rice plant. The fertility gene FL2 has a nucleotide sequence of SEQ ID NO: 1, 4 or 27 in *Oryza Sativa* ssp. *indica*, and the corresponding amino acid sequence is SEQ ID NO: 2. The fertility gene FL2 has a nucleotide sequence of SEQ ID NO: 5 in *Oryza japonica*, and the corresponding amino acid sequence is SEQ ID NO: 6. The fertility gene FL2 has a nucleotide sequence of SEQ ID NO: 10 or 11 in barley, and the corresponding amino acid sequence is SEQ ID NO: 12. The fertility gene FL2 has a nucleotide sequence of SEQ ID NO: 13 or 14 in sorghum, and the corresponding amino acid sequence is SEQ ID NO: 15. The fertility gene ZmFL2 has a nucleotide sequence of SEQ ID NO: 13 or 14 in maize, and the corresponding amino acid sequence is SEQ ID SEQ ID NO: 15. The fertility gene ZmFL2 has a nucleotide sequence of SEQ ID NO: 16 or 17 in maize, and the corresponding amino acid sequence is SEQ ID SEQ ID NO: 18. The fertility gene FL2 has a nucleotide sequence of SEQ ID NO: 19 in millet, and the corresponding amino acid sequence is SEQ ID NO: 20. The fertility gene FL2 has a nucleotide sequence of SEQ ID NO: 21 or 22 in *Brachypodium distachyon*, and the corresponding amino acid sequence is SEQ ID NO: 23.

The present disclosure also provides one of the following sequences: a) a DNA sequence with at least 90% (preferably at least 95%) sequence similarity of FL2 gene described above and a homologous function, b) an DNA sequence hybridizable with the DNA sequence of a) under a stringent condition; c) an DNA sequence complementary to any one of the DNA sequence described above in a)-b).

The fertility gene described above may be isolated from various plants. As known by one skilled in the art, the fertility gene of the present disclosure comprises functionally equivalent sequences which are highly homologous to FL2 gene and regulate fertility likewise. The highly homologous and functionally equivalent sequences include DNA sequences hybridizable with FL2 gene of the present disclosure under a stringent condition. "A stringent condition" used in the present disclosure is commonly understood by one of ordinary skill in the art and may comprise: hybridizing in a hybridization solution consisting of 400 mM NaCl, 40 mM PIPES (pH6.4) and 1 mM EDTA at 60° C. for 12-16 h, then washed with the wash solution consisting of 0.1% SDS and 0.1×SSC at 65° C. for 15-60 min.

The functionally equivalent sequence also includes a DNA sequence regulating plant fertility with at least 90%, at least 95%, at least 96%, at least 97%, at least 98%, or at least 99% sequence similarity of FL2 gene in the present disclosure, which may be isolated from any plant. A percentage of sequence similarity may be obtained by bioinformatic algorithms commonly known by a person skilled in the art, including Myers and Miller algorithm (Bioinformatics, 4(1): 11-17, 1988), Needleman-Wunsch global alignment method (J. Mol. Biol., 48(3):443-53, 1970), Smith-Waterman local alignment method (J. Mol. Biol., 147: 195-197, 1981), Pearson and Lipman similarity search method (PNAS, 85(8): 2444-2448, 1988), Karlin and Altschul algorithm (Altschul et al, J. Mol. Biol., 215(3): 403-410, 1990; PNAS, 90: 5873-5877, 1993), which are well known to those skilled in the art.

The nucleotide sequence of the fertility gene of present disclosure may be isolated from any plant, including but not limited to, *Brassica*, maize, wheat, sorghum, *Crambe* Zinn, *Sinapis alba*, castor bean, sesame, cottonseed, linseed, soybean, *Arabidopsis, Phaseolus*, peanut, alfalfa, oat, rapeseed, barley, oat, rye, millet, dhurra, riticale, einkorn, Spelt, emmer, flax, Gramma grass, Tripsacum, euchlaena Mexicana, *Festuca ovina*, Perennial wheatgrass, sugarcane, *Vaccinium oxycoccos*, papaya, banana, Safflower, oil palm, muskmelon, apple, cucumber, dendrobe, gladiolus, chrysanthemum, Liliaceae, cotton, eucalyptus, sunflower, *Brassica rapa*, beet, coffee, ornamental plant, conifer and so on. Preferably, the plant includes maize, soybean, Safflower, mustard, wheat, barley, rye, rice, cotton, and sorghum.

Also provided in the present disclosure is a method of influencing plant fertility by influencing a nucleotide sequence of FL2 or by regulating the transcription and expression of FL2 gene. The expression of "influencing plant fertility" means changing the fertility of a plant, for example obtaining male sterility, by regulating the expression of FL2 gene. Particularly, depending on the specific application, the FL2 gene expression in plant may be influenced by many methods to regulate the plant male fertility. More particularly, the expression of FL2 gene may be manipulated by all kinds of tools available to one of ordinary skill in the art. For example, mutation, mutagenesis, introduction of an antisense gene, co-suppression, introduction of hairpin, and alike can be used to interfere the normal expression of FL2 gene, and to obtain the male sterile plant. In other embodiments, the present disclosure also includes the way of recovering the male fertility to the plant with disturbed FL2 expression by introducing the wild-type nucleotide sequence of FL2 to the plant.

Further provided in the present disclosure are the mutant nucleotide sequence of FL2 gene that leads to male sterility and a male sterile mutant material. More particularly, the male sterile mutant material is obtained by a process of mutating endogenous FL2 gene of rice, or mutating of the nucleotide sequence of a gene highly homologous to FL2 gene, leading to loss of male fertility. The term of "mutating" includes, but is not limited to the following methods, for example gene mutation induced by physical or chemical method. The chemical method includes mutagenesis induced by mutagen such as EMS etc. The mutation may be point mutation, nucleotide deletion, or nucleotide insertion, or gene silencing by means of RNAi, site-directed mutagenesis and so on.

Figure 6A:
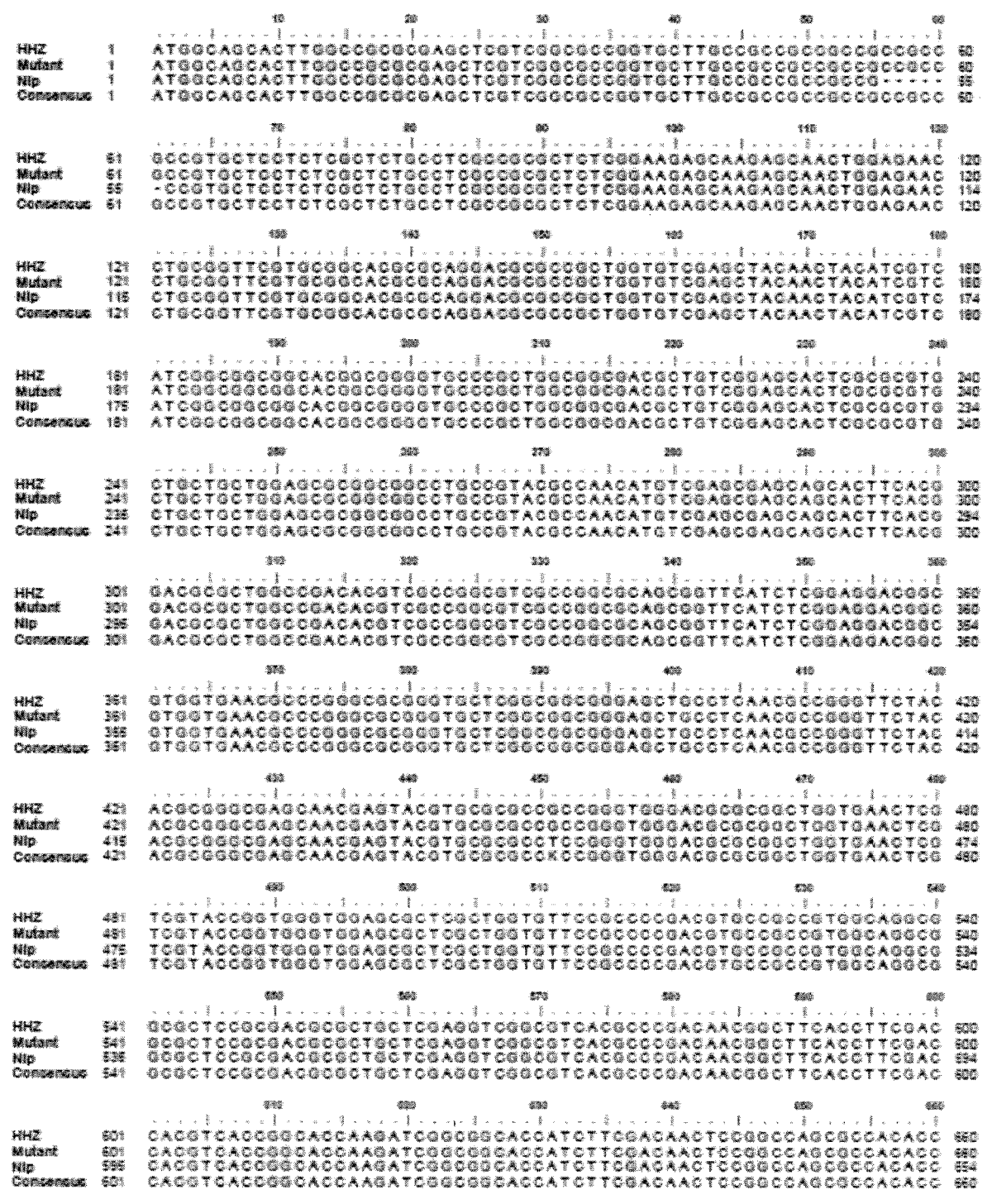
Figure 6B:
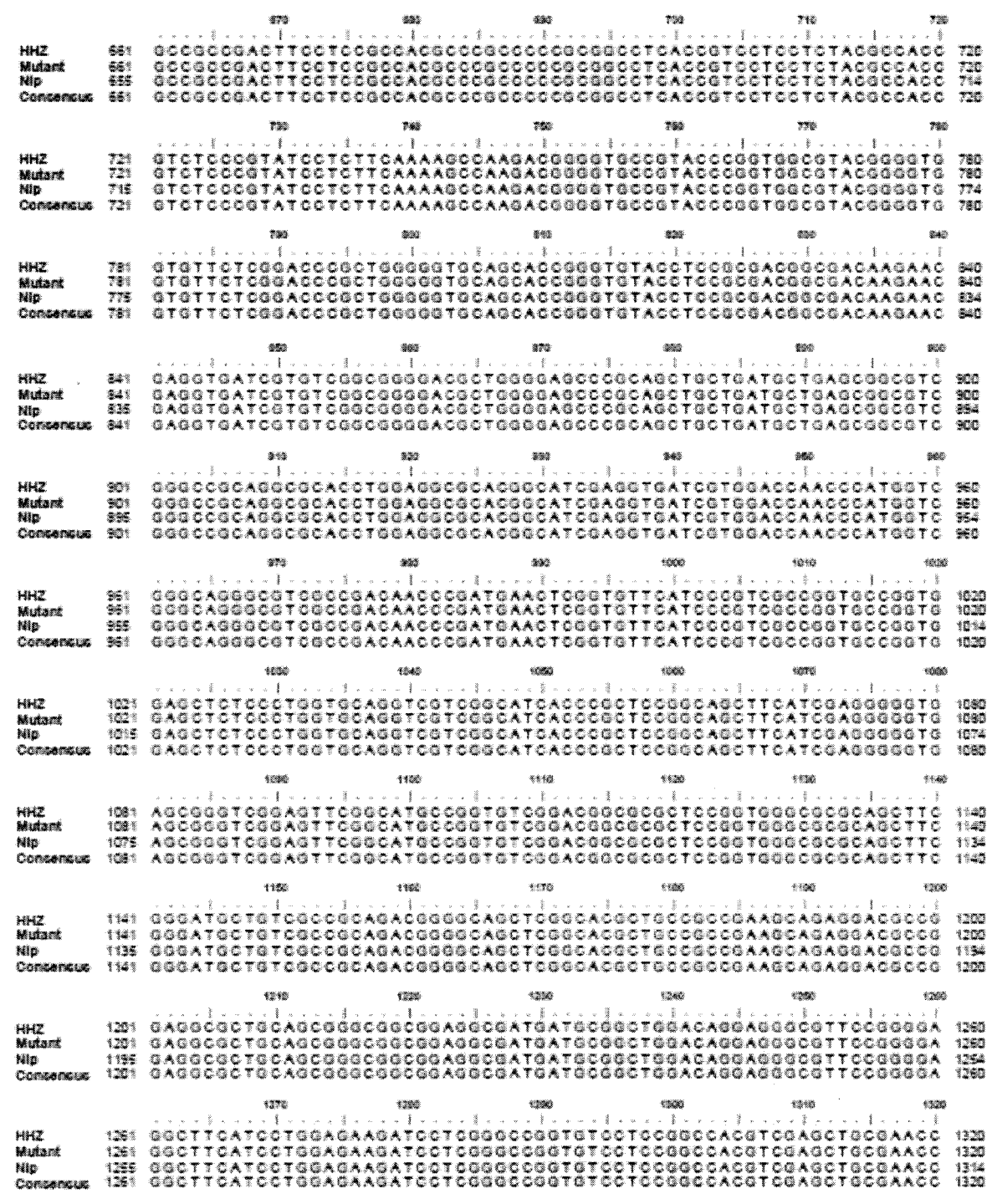
Figure 6C:
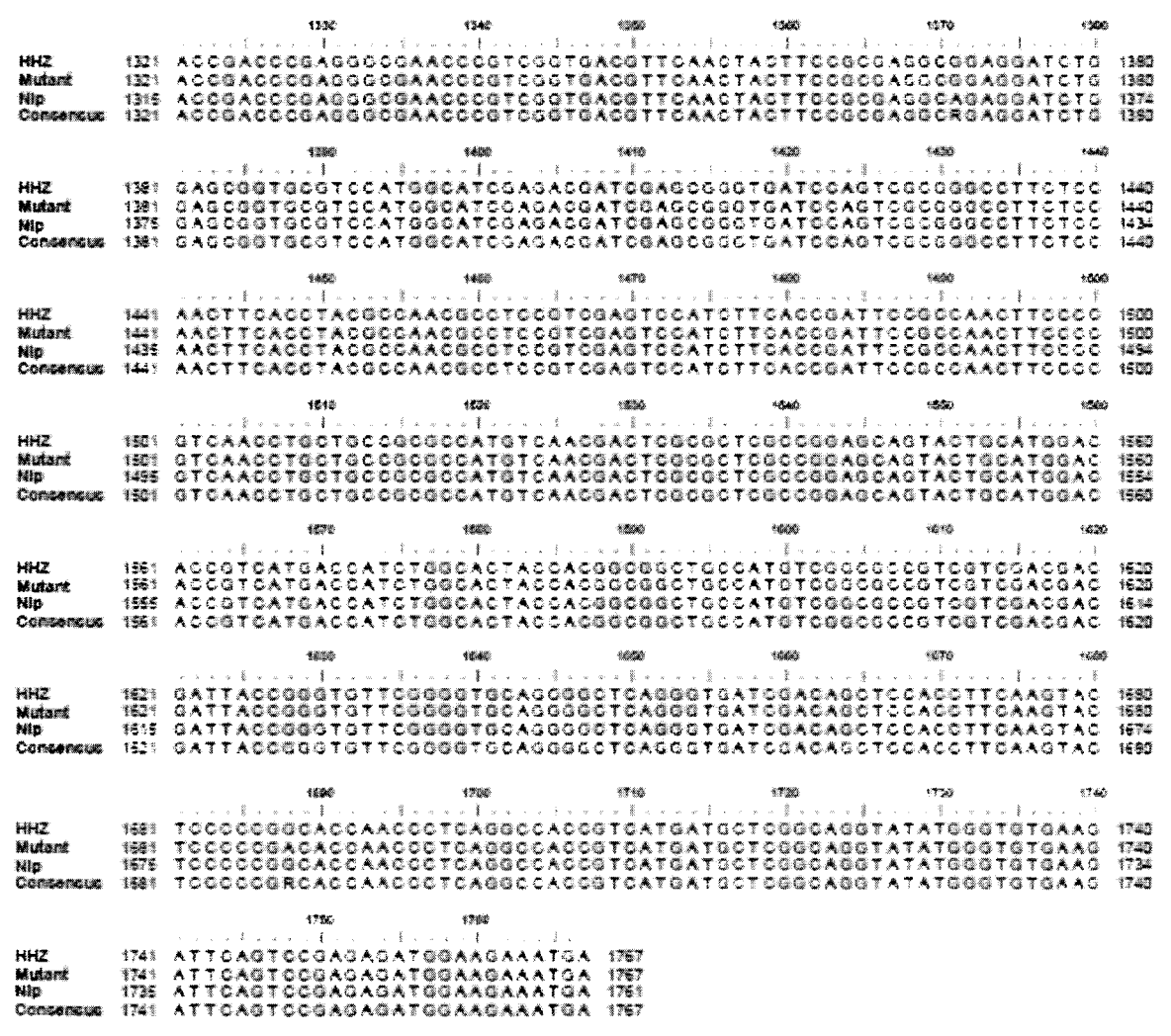

Particularly, also provided in the present disclosure is a male sterile mutant of rice, containing the mutant FL2 gene. The nucleotide sequence of the mutant male sterility gene is shown as SEQ ID NO: 7 and the amino acid sequence thereof is SEQ ID NO: 8. Compared with wild-type, in the male-sterile mutant, G is mutated into A at the 1688$^{th}$ nucleotide of the coding sequence of the mutant male sterility gene (FIG. 6A-C), which leads to a glycine (G) to Aspartic Acid (D) change at the 563rd amino acid in the corresponding encoded protein sequence. As known by the person skilled in the art, the nucleotide sequence of SEQ ID NO: 7 can be constructed into a plant expression vector to transform a plant and obtain a new transgenic male sterile mutant material.

Further provided in the present disclosure is the promoter of FL2 gene with a function of specific expression in anther, and the corresponding nucleotide sequence of the promoter is a nucleotide sequence 700 bp to 2500 bp upstream of ATG of the FL2 gene. More particularly, in rice, the nucleotide sequence of the promoter of OsFL gene is SEQ ID NO: 3 or SEQ ID NO: 9. The nucleotide sequence shown as SEQ ID NO: 3 and SEQ ID NO: 9 were ligated with the reporter gene GUS and transformed into plants respectively. The resulting transgenic plants were analyzed. Specifically, the roots, stems, leaves, and flowers were stained for GUS activity. It was found that the GUS gene driven by the promoter of OsFL2 gene is mostly expressed in rice anthers, particularly expressed highly specifically at the P7 stage of anther development. Therefore, the promoter of SEQ ID NO: 3 or SEQ ID NO:9 provided in the present disclosure is be an anther-specific promoter.

The anther-specific promoter provided in the present disclosure includes the nucleotide sequence of SEQ ID NO: 3 or SEQ ID NO: 9, a nucleotide sequence with at least 90% sequence similarity to the nucleotide sequence of SEQ ID NO:3 or SEQ ID NO: 9, or a sequential nucleotide fragment of at least 100 bp from the nucleotide sequence of SEQ ID NO: 3 or SEQ ID NO: 9, which may activate the expression of nucleotide sequences operably linked to the promoter in plant anther. An expression vector, a transgenic cell line, a host bacterium, and so on containing the nucleotide sequence described above also fall in the protection scope of the present disclosure. A primer pair for amplifying any one of the nucleotide sequences of the promoter of SEQ ID NO: 3 and SEQ ID NO: 9 also fall in the protection scope of the present disclosure.

The nucleotide sequence of the promoter provided in the present disclosure may be used to isolate corresponding nucleotide sequences from plants other than rice, particularly, by homology-based cloning from other monocotyledons. These corresponding nucleotide sequences may be isolated and identified by means of PCR, hybridization etc. based on the homology between these corresponding nucleotide sequences and the promoter of the present disclosure or the promoter. Therefore, the embodiments of present disclosure also comprise the corresponding fragments, which have sequence similarities to the promoter sequence of SEQ ID NO: 3 or SEQ ID NO: 9 (or fragments thereof) and may be isolated based on the similarities.

The term "promoter" used herein means a regulatory DNA region, commonly including TATA box guiding RNA polymerase II to initiate RNA synthesis at a proper transcriptional start site of a specific coding sequence. The promoter may also include other recognition sequences commonly located upstream of the TATA box, named as an upstream promoter element with a function of regulating transcriptional efficiency. As known to those skilled in the art, although the nucleotide sequence of the promoter region of the present disclosure has been identified, the isolation and identification of other regulatory element in upstream region of the TATA box of a specific promoter region identified in the present disclosure also falls in the scope of the present disclosure. Therefore, the promoter of the present disclosure may be generally further defined to include the upstream regulatory elements that regulate spatial and temporal expression patterns of the coding sequence. The promoter elements expressed in a target tissue (such as male reproductive organs) may be identified and isolated in the same way, and these promoter elements may be used together with a core promoter to examine the preferential expression in male-specific tissues. The core promoter means a minimal sequence for transcriptional onset, for example, a sequence known as the TATA box, which commonly exists in the promoter of gene encoding a protein. Therefore, alternatively, the upstream promoter of FL2 gene may be used in association with the core promoter of the FL2 gene or core promoters from other sources.

The core promoter may be one of the known core promoters, such as 35S or 1 9S promoter of Cauliflower Mosaic Virus (U.S. Pat. No. 5,352,605), Ubiquitin promoter (U.S. Pat. No. 5,510,474), IN2 core promoter (U.S. Pat. No. 5,364,780), or figwort mosaic virus promoter.

The function of the gene promoter may be analyzed by the following methods: the nucleotide sequence of the promoter is operably linked to reporter gene to form a transformable construct, then the construct is transformed into plants to obtain transgenic progeny, and the expression of reporter gene in the transgenic progeny is examined for the expression pattern of the promoter. Alternatively, the promoter sequence linked to a reporter gene is subcloned into an expression vector, and the function of the promoter or other regulatory regions thereof is detected through the transient expression experiment.

The selection of suitable expression vectors for testing the function of the promoter or regulatory regions thereof depends on the host and the method of introducing the expression vector into the host, and the method is well known to one of ordinary skill in the art. For a eukaryotic gene, the sequence that should be subcloned into the expression vector comprises a region controlling transcription initiation and regulation. These regions are operably linked to a reporter gene including GFP, UidA, GUS gene or luciferase. The expression vector with a putative regulatory region located in the genome may be transformed into a whole organ, such as pollen at specific stages, or callus to examine its functions.

Furthermore, the promoter of the present disclosure may be linked to heterogenous nucleotide sequences other than the FL2 gene for to drive their expression. The nucleotide sequence of the promoter of the present disclosure and fragment and variant thereof and the heterogenous nucleotide sequence may be assembled into an expression cassette for expressing in target plants, more particularly in male organs of the plant. The expression cassette has a proper restriction site for inserting the promoter and the heterogenous nucleotide sequence. The expression cassettes may be used to genetically manipulate any plant to obtain desired corresponding phenotype.

The FL2 gene promoter of the present disclosure, more particularly the FL2 gene promoter of rice, may be used to activate the expression of several heterogenous nucleotide sequences to make the transformed plant male sterile. Specifically, the heterogenous nucleotide sequence may encode enzymes accelerating carbohydrate degradation, carbohydrate modification enzyme, amylase, debranching enzyme, or pectinase, such as thea-amylase gene, auxin, rot B, cytotoxin gene, diphtheria toxin, DAM methylase, avidin, or heterogenous nucleotide sequences selected from a prokaryotic regulation control system. The heterogenous nucleotide sequence can also be dominant male sterility gene.

In some embodiments, the nucleic acid operably linked to the downstream of the promoter in the present disclosure may be operably linked to a structural gene, a regulatory gene, an antisense sequence of the structural gene, an antisense sequence of the regulator gene or micro RNA interfering with the expression of a particular endogenous gene.

More explicitly, the gene of SEQ ID NO: 1 and SEQ ID NO: 5 regulating plant fertility provided in the present disclosure may be constructed into the downstream of the promoter of SEQ ID NO: 3 and SEQ ID NO: 9 to drive the specific expression of the gene in anther, or may be used to construct an RNAi vector targeting the gene of SEQ ID NO: 1 driven by the promoter of SEQ ID NO: 3 or SEQ ID NO: 9 to silence the FL2 gene expression and to obtain the male sterile mutant of SEQ ID NO:1 gene.

The nucleotide sequence of the promoter of the present disclosure may be isolated from any plant, including but not limited to, *Brassica*, maize, wheat, sorghum, *Crambe* Linn, *Sinapis alba*, castor bean, sesame, cottonseed, linseed, soybean, *Arabidopsis, Phaseolus*, peanut, alfalfa, oat, rapeseed, barley, oat, rye, millet, dhurra, riticale, einkom, Spelt, emmer, flax, Gramma grass, Tripsacum, euchlaena Mexicana, *Festuca ovina*, Perennial wheatgrass, sugarcane, *Vaccinium oxycoccos*, papaya, banana, Safflower, oil palm, muskmelon, apple, cucumber, dendrobe, gladiolus, chrysanthemum, Liliaceae, cotton, eucalyptus, sunflower, *Brassica rapa*, beet, coffee, ornamental plant, conifer and so on. Preferably, the plant includes maize, soybean, Safflower, mustard leaf, wheat, mustard leaf, barley, rye, rice, cotton and sorghum.

The present disclosure also provides a construct comprising FL2 gene and/or the promoter of FL2 gene, which includes a so-called vector or an expression cassette. The promoter of the construct driving the linked nucleotide sequence to express in the plant may be a natural promoter or a substituted promoter. The promoter of the construct may be an inducible promoter. The nucleotide sequence of FL2 gene may be linked to an anther-specific promoter, preferably, which may drive the nucleotide sequence of FL2 gene to fully express in the early development of anther, for example specifically in P7 of anther development. Particularly, the useful promoter types include a constitutive viral promoter, such as 35S promoter of Cauliflower Mosaic Virus (CaMV), 19s promoter of Cauliflower Mosaic Virus (CaMV), 35S promoter of figwort mosaic virus, and ubiquitin promoter.

A tissue-specific promoter may be used to enhance the transcription and/or expression targeted a specific plant tissue. The promoter may express in both the target tissue and other plant tissues, or express mainly in the target tissue, or express lower in the target tissue than the other plant tissues, or express highly preferably in the target tissue. In one embodiment, the promoter prefers to express particularly in plant male tissues or plant female tissues. For the method of present disclosure, the promoter may not be limited to any specific promoter with male tissue preference, and many promoters of such type known by the person skilled in the art may be used.

The natural FL2 promoter described herein is an example of the useful promoters. Another type of such promoters comprise 5126 promoter, MS45 promoter, MS26 promoter, BS92-7promoter, SGB6 regulatory element and TA29 promoter and so on, which drive the linked gene to express in plant male tissues. The construct also comprises the promoter with gamete expression specificity. The promoters with gamete tissue expression specificity includes PG47 promoter and ZMI 3 promoter.

The construct described above may also comprise other components depending on the purpose and use of the vector construct. For example the construct may further comprise a selection marker gene, a targeting or regulatory sequence, a stabling sequence, a guiding sequence, or an intron. The expression cassette includes a target heterogenous nucleotide sequence with a transcriptional terminator and a translational terminator functioning in a plant at the 3' end thereof. The terminator may be the terminator of the gene of the present disclosure, or an exogenous terminator. More particularly, the above-mentioned terminator may be a termination region of nopaline synthase or octopine synthase.

If it is desired to target the expression product of the heterogenous nucleotide sequence to a specific organelle, such as plastid, amyloplast, endoplasmic reticulum or cell surface or extracellular secretion, the expression cassette may also comprise a nucleotide sequence that encodes a transit peptide. The transit peptide is known by the person skilled in the art and can be but not limited to a small subunit of Rubisco, a plant EPSP synthase, a maize Brittle-I chloroplast transit peptide etc.

In the process of preparing the expression cassette, multiple DNA fragments may be manipulated to provide a DNA sequence in a proper direction or in a correct reading frame. In order to reach this aim, DNA fragments may be linked together via an adapter or a linker, or other convenient multiple cloning sites through other operations etc.

Further, the construct provided in the present disclosure also includes a selection marker gene for selecting transformed cells or transformed tissues. The selection marker gene includes an antibiotic-resistance gene or an herbicide-resistance gene. The proper selection marker gene includes, but is not limited to a chloramphenicol resistant gene, a hygromycin resistant gene, a streptomycin resistant gene, a miramycin resistant gene, a sulfonamides resistant gene, a glyphosate resistant gene, a phosphinothricin resistant gene. The selection marker gene may be also a red fluorescent protein gene, a cyan fluorescent protein gene, a yellow fluorescent protein gene, a luciferase gene, a green fluorescent protein gene, and an anthocyanin biosynthetic gene etc.

The expression cassette or the vector provided in the present disclosure may be inserted into a plasmid, a cosmid, a yeast artificial chromosome, a bacteria artificial chromosome or any other vector suitable to be transformed into a host cell. Preferably the host cell is a bacteria cell especially the cell used to clone polynucleotide, maintain polynucleotide, or transform a plant cell, such as *Escherichia Coli, Agrobacterium tumefaciens* and Hair root soil bacteria. In the case of the host cell being a plant cell, the expression cassette or the vector may be inserted into a genome of the transformed plant cell, and the insertion may be either site-specific or random. Preferably, the insertion may be realized through homologous recombination. In addition, the expression cassette or the vector may be free from any chromosome. The expression cassette or the vector of the present disclosure can be in the nucleus, chloroplast, mitochondria and/or plastid of a plant cell. Preferably, the expression cassette or the vector may be inserted into a chromosome DNA in the plant cell nucleus.

The present disclosure also comprises the use of the FL2 gene disclosed in the present disclosure and the promoter thereof. In some embodiments of applications, the FL2 gene or the promoter thereof may be used to propagate and maintain the male sterile line obtained by mutating the FL2 gene or other genes related to fertility.

In details, the propagation and maintenance of the above-mentioned male sterile line involves using a male sterile mutant with a homozygous recessive nuclear gene as a transgenic acceptor and transformation of three tightly linked target genes into the male sterile mutant. The three tightly linked genes comprise a fertility restoration gene, a pollen inactivation gene, and a color/fluorescence-label screening gene. The fertility restoration gene may recover the fertility of the sterile transgenic acceptor. The pollen inactivation gene may inactivate any pollen containing the transformed exogenous gene. And the color/fluorescence-label screening gene may be used to sort the transgenic seeds from the non-transgenic seeds, and the sorted non-transgenic seeds may be used as a sterile line to produce hybrid seeds, while the sorted transgenic seeds may be used as a maintainer line to produce a sterile line continuously and steadily.

More explicitly, according to one embodiment of the present disclosure, rice recessive nuclear sterile fl2 (fl2 mutant may be used as a receptor, and 3 tightly linked genes are transformed into the sterile line, wherein a fertility restoration gene OsFL2 may recover fertility of the transformed acceptor, a pollen inactivation gene Zm-PA may inactivate pollen, and a fluorescence screening (color sorting) gene RFP(r) is used to sort transgenic seeds from non-transgenic seeds, and the sorted non-transgenic seeds may be used as a sterile line to produce hybrid seeds, and the sorted transgenic seeds may be used as a maintainer line to produce a sterile line continuously and steadily. This technology produces non-transgenic product and bypasses the bottleneck problem in the process of rice hybrid seed preparation that low resource utilization in the three-line method and unstable fertility of the sterile line in the two-line method.

An anther-specific promoter provided in the present disclosure may be used to drive the specific expression of an exogenous gene in anther to avoid the continuous expression of the exogenous gene in other tissues of the plant and any adverse effects caused by that. The anther-specific promoter may also be used in the functional analysis and identification of genes related to the plant pollen development, the establishment of the male sterile line and the restorer line, and pollen abortion experiment, and the biosafety problem caused by a plant transgene flow or pollen escape may be avoided, which is important to establish the male sterile line and the restorer line.

The present invention also provides a method of producing a plant, comprising:

(1) constructing an expression cassette provided herein,
(2) introducing the resulting expression cassette of step (1) into plant cells,
(3) regenerating transgenic plants from transformed plant cells, and screening through the transgenic plants, and
(4) optionally, propagating the plant of step (4) to obtain progenies.

The transgenic plant of the present disclosure is prepared by transformation methods known to those skilled in the art of a plant biotechnology. Any method may be used to transform a recombinant expression vector into the plant cell to generate the transgenic plant of the present disclosure. The transformation methods include a direct transformation method and an indirect transformation method. The proper direct transformation method includes DNA intake induced by polyethylene glycol, lipidosome-mediated transformation, introduction by particle gun, electroporation and microinjection and so on. In some embodiments of the present disclosure, the present disclosure uses transformation technology based on *Agrobacteria* (referring to Horsch R B et al (1985) Science 225: 1229; White F F, Vectors for Gene Transfer in Higher Plants, Transgenic plants, Volume 1, Engineering and Utilization, Academic Press, 1993, pp. 15-38; Jenes Bet al. Techniques for Gene Transfer, Transgenic plants, Volume 1, Engineering and Utilization, Academic Press, 1993, pp. 128-143, etc). *Agrobacterium* strains (such as *Agrobaterium twnefaciens* or *Agrobacterium rhizogenes*) contain a plasmid (Ti plasmid or Ri plasmid) with a T-DNA element. The plasmid with the T-DNA is transferred into plant after *Agrobacterium* transfection, with the T-DNA eventually integrated into the plant cell genome. T-DNA is located in the Ri-plasmid or the Ti-plasmid, or contained in a binary vector. An *Agrobacterium*-mediated transformation method is described in the examples. The *Agrobacterium*-mediated transformation method is most suitable for dicotyledons, but also suitable for monocotyledons. The way of transforming *Agrobacterium* into plants is described in the examples. Transformation may lead to both transient transformation and expression, and stable transformation and expression. Although the nucleotide sequence of the present disclosure may be inserted into various plants and various plant cell types, it is especially suitable for crop cells.

Compared with the prior art, the present disclosure has the following benefits: a rice anther development gene and the male sterile line generated by the mutation of the rice anther development gene are provided in the present disclosure. The male sterility is not influenced by environment and may be recovered by wild-type transgene. The rice anther development gene and the male sterile line generated by the mutation of the rice pollen development gene provide necessary components for constructing the third generation hybrid breeding system. The male sterile line generated by the mutation of the rice pollen development gene can be used to produce hybrid seeds, and is vital to improve the existing three-line and two-line methods.

EXAMPLES

The invention is now described with reference to the following Examples. The Examples are provided for the purpose of illustration only, and the invention is not limited to these Examples, but rather encompasses all variations which are evident as a result of the teachings herein.

Example 1: Screening for a Rice Male Sterile Mutant (Osfl2)

The seeds of the rice variety (*Oryza sativa* L. spp. *Indica*) Huanghuazhan (MO) were mutagenized by EMS (0.7%) for 12 hours to obtain the mutagenized population (M1). The seeds generated by the mutagenized plants from the M1 seeds were harvested and mixed to obtain a mutant library (M2). The plants from the M2 generation seed were screened to obtain male sterile plants at the seed maturation stage. The sterile plant was reproduced by cutting off rice stubbles, and pollen development in the reproduced plant was tested by I2-KI staining in reproductive period. A male sterile mutant showed no pollen and was named as Osfl2.

Example 2: Genetic Analysis of the Rice Male Sterile Mutant (Osfl2)

The sterile plant of the Osfl2 mutant was crossed with wild-type Huanghuazhan, and 80 F1 generation plants were all fertile. The F1 generation plants were self-fertilized to obtain 300 F2 plants, of which 78 plants manifested no pollen sterility and 222 plants showed complete fertility. The segregation ratio between the sterile plants and the fertile plants is very close to 1:3, which revealed the phenotype to be controlled by a recessive nuclear gene.

Example 3: Stability Analysis of the Rice Male Sterile Mutant (0412)

To confirm whether the sterility of the osfl2 mutant was influenced by environmental conditions such as light or temperature etc., the F2 generation plants obtained through crossing the sterile plant with wild-type Huanghuazhan were grown in Shenzhen, Sanya, Hunan, Beijing to further observe the sterility and the segregation ratio. In all areas, the segregation ratio between the sterile plants and the fertile plants is 1:3 (FIG. 1), and the reproduced plants from the sterile rice stub still manifested sterility, thus the sterility of the mutant was not influenced by environmental factors.

TABLE 1

The segregation ratio in the F2 generation plant obtained by self-fertilization of the F1 plants (the progeny of Osfl2 mutants and the wild type Huanghuazhan).

|  | Number of fertile plants | Number of sterile plants | χ2 (3:1) |
| --- | --- | --- | --- |
| Shenzhen | 88 | 31 | 0.034 |
| Sanya | 104 | 29 | 0.150 |
| Hunan | 65 | 21 | 0.000 |
| Beijing | 61 | 19 | 0.033 |

Example 4: Phenotypic Analysis of the Reproductive Organ of the Rice Male Sterile Mutant (osfl2)

Figure 2:
FIG. 2—depicts anther morphology of Huanghuazhan with mutant OsFL2 or wild-type OsFL2.
Figure 3:
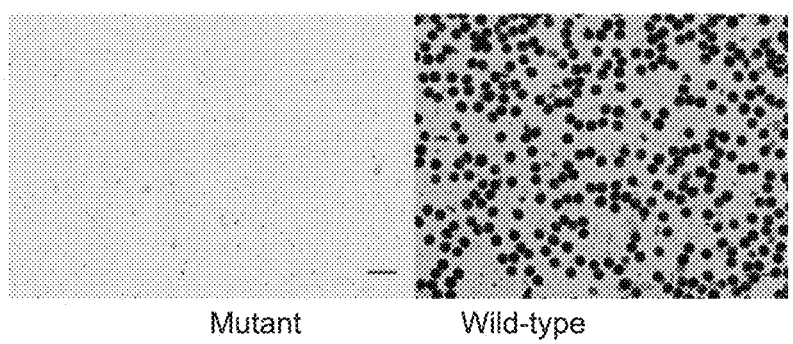
FIG. 3—depicts pollen dye-staining analysis of Huanghuazhan with mutant OsFL2 or wild-type OsFL2.
Figure 4:
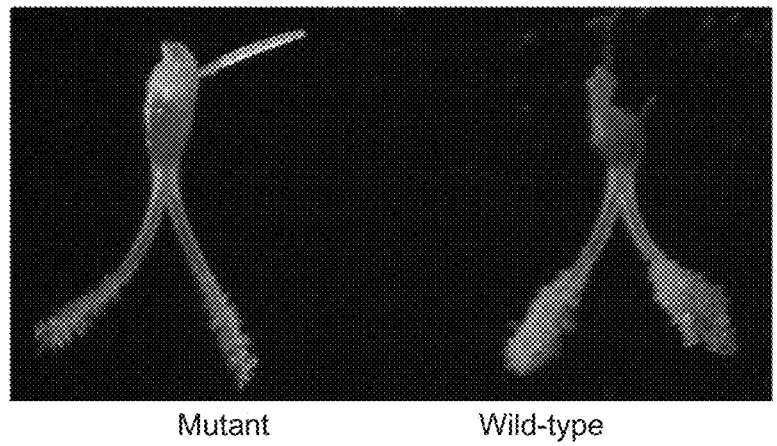
FIG. 4—depicts morphological comparison of female organs of Huanghuazhan with mutant OsFL2 and wild-type OsFL2.
Figure 5:
FIG. 5—depicts the exposed stigma of mutant plant, and an arrow indicates the exposed stigma.

Compared with the wild-type plant, the mutant plant grew and developed normally, blooming at the same stage. The size, morphology, opening size and opening time of lemma and glum of the mutant plant were not different from the wild-type plant (FIG. 1). But the anther of the mutant plant was white, thin, small, and indehiscent (FIG. 2), with no pollen. Further I2-KI staining was performed to detect if there is any pollen in the mutant plant, and it showed that the wild-type pollen stained normally while the mutant plant did not have pollen (see FIG. 3). The female organs of the mutant plant (including ovary, style, stigma) were all slightly bigger than the counterparts from the wild-type plant (FIG. 4). Exposure rate of stigma of the mutant plant was at least 89% (FIG. 5), while the stigmas of wild-type Huanghuazhan are rarely exposed. Sterile mutant plants were mixed with the fertile plant and sowed under a natural condition, so that the sterile mutant plant may be cross-pollinated by the fertile plant to recover fruiting ability. The statistical analysis of 100 mutant plants showed that by this means and the seed setting rate was increased to at least 40%. By contrast, under an artificial condition, the sterile mutant plant may be cross-pollinated from the fertile plant, and seed setting rate was increase to 70%-80%. Further the seed of the mutant plant developed normally without any defects.

Example 5: Gene Cloning of the Rice Male Sterile Mutant

Cloning of the mutant gene was based on the Mutmap method, which involves constructing F2 progenies by crossing the mutant with the wild-type parent, and mapping the gene by re-sequencing. The sterile plant was crossed with wild-type Huanghuazhan, then 30 sterile plants of F2 generation were selected for extraction of genomic DNA, and the genomic DNA was mixed equally for high-throughput genome sequencing to get 20 Gb sequence data amounting to 50×rice genome. The mutant gene may be Os10g38050 allele located on the 10th chromosome compared with the genomic sequence of wild-type Huanghuazhan. The full-length coding sequence of the gene of wild-type Huanghuazhan is 1767 bp, and the nucleotide sequence of the gene was shown as SEQ ID NO:1. The protein encoded by SEQ ID NO:1 contains 588 amino acids and the sequence of amino acids was shown as SEQ ID NO:2. In the sterile mutant, G was mutated into A at the 1688th nucleotide of the coding sequence of the gene (FIG. 6), and as a result, Glycine (G) was changed into Aspartic acid (D) at the 563$^{th}$ amino acid of the corresponding protein sequence encoded by the gene (FIG. 7). The latest SNP (Single Nucleotide Polymorphism) research tool HRM (High Resolution Melt) analysis was performed to further confirm that all non-pollen plants carried the homozygous mutation while the fertile plant carried a homozygous wild-type site or a heterozygous site. The offspring from self-pollination of the homozygous wild-type plant was all fertile, and the offspring from self-pollination of the heterozygous plant shows a segregation ratio at 1:3 between the sterile offspring and the fertile offspring. The cDNA coding sequence of the gene contains several sequence polymorphisms between O. Japonica rice Nipponbare and wild-type Huanghuazhan (FIG. 6). Compared with Huanghuazhan OsFL2, Nipponbare OsFL2 contains a 6-bp nucleotide deletion from the 59th to the 64th of the coding sequence, a G-to-T nucleotide substitution at the position 451, and a G-to-A nucleotide substitution at position 1371 of the coding sequence. As a result, two protein polymorphism were detected, a deletion containing the 20$^{th}$ and the 21$^{th}$ amino acids of the protein sequence, and a Alanine (A) to Serine (S) substitution at position 151 of the protein (FIG. 7). The nucleotide sequence of the Nipponbare gene was shown as SEQ ID NO:5, and the coding amino acid sequence thereof was SEQ ID NO:6. Further analysis showed that the gene does not show any polymorphism between indica rice variety 9311 and wild-type Huanghuazhan.

Figure 8:
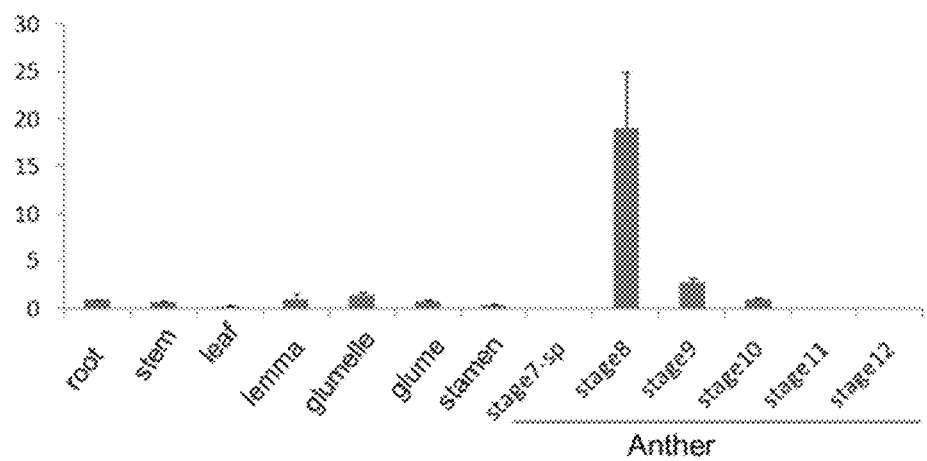
FIG. 8—Analysis of expression level of OsFL2 in different tissues and organs of rice.

Example 6: Expression Pattern Analysis of OsFL2 Gene in Different Organs of the Rice A pair of primers were designed based on the cDNA sequence of OsFL2, with the forward primer F1 5' GCCTCACCGTCCTCCTCTAC 3' (SEQ ID NO: 33) and the reverse primer R1 5' CGGGTCCGAGAACACCAC 3' (SEQ ID NO: 34). Meanwhile, primers for internal controls were designed against a rice gene Actin, with a forward primer 5' GCTATGTACGTCGCCATCCA 3' (SEQ ID NO: 35) and a reverse primer 5' GGACAGTGTGGCTGACACCAT 3' (SEQ ID NO: 36). Total RNA was extracted from Huanghuazhan rice and used as the template for the synthesis of the 1$^{st}$ strand cDNA. Real-time quantitative PCR was used to analyze OsFL2 gene expression profile in the root, stem, leaf, lemma, palea, glume, pistil and young anther at primordium differentiation stage (stage 6), young anther at early pollen mother cell meiotic stage (stage 7), tetrad formation stage (stage 8), early microspore stage (stage 9), middle and late microspore stage (stage 10), pollen maturing stage (stage 12), and the result as depicted in FIG. 8 showed that the OsFL2 gene had specific and high expression in young anther at pollen mother cell meiosis stage (stage 7). The expression of the OsFL2 gene began to decrease at tetrad formation stage (stage 8), while the expression of the OsFL2 gene was very low in the root, stem, leaf, seed and other anther developmental stage.

Figure 9:
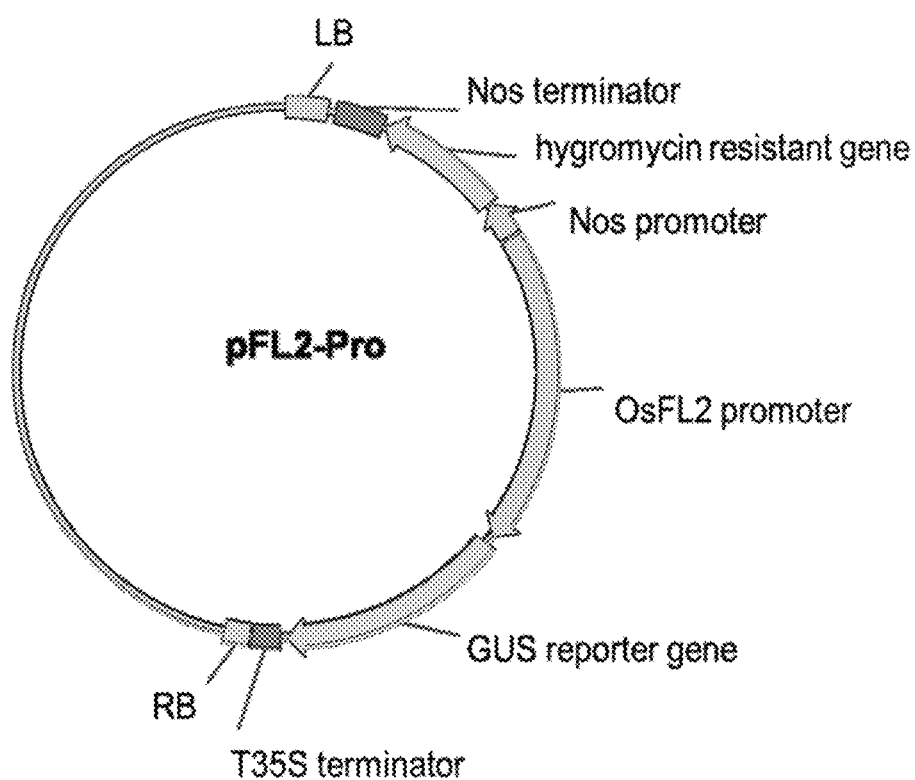
FIG. 9—Expression vector of the promoter of OsFL2 gene.
Figure 10:
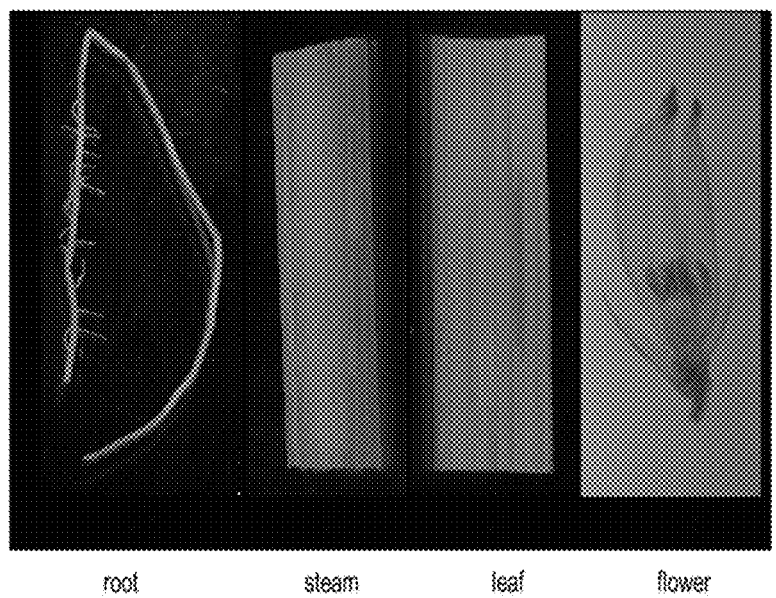
FIG. 10—depicts the promoter of OsFL2 gene activates GUS gene to express specifically in rice anther.
Figure 11:
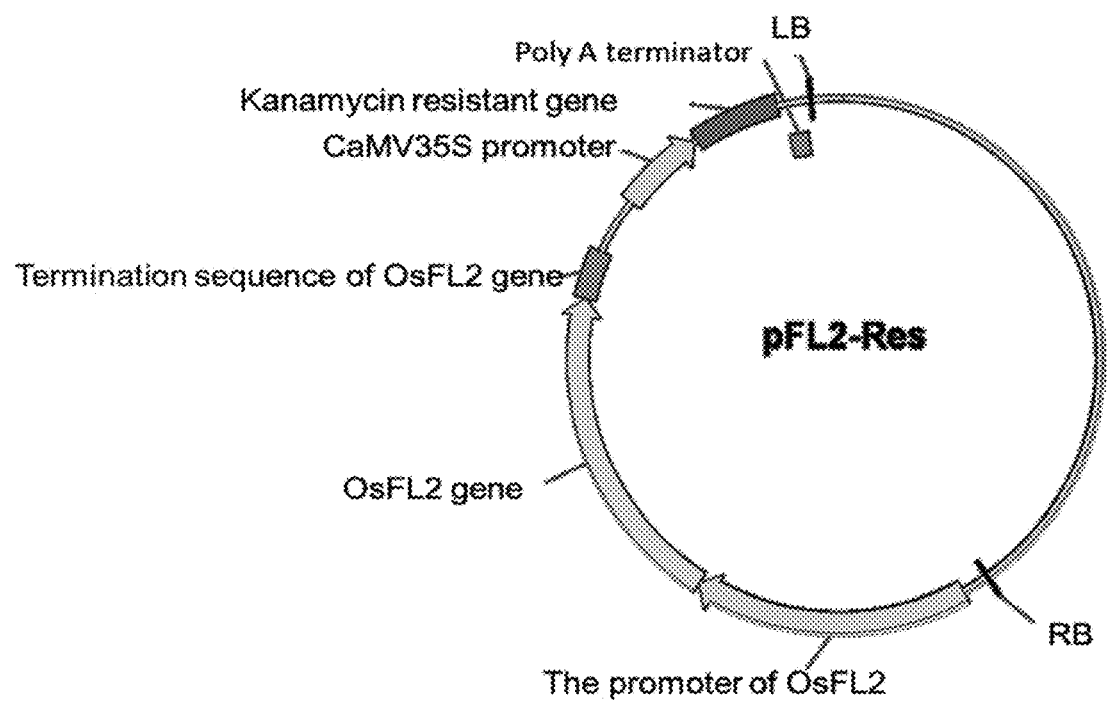
FIG. 11—depicts transgene complementation vector of the rice male sterile mutant (OsFL2).
Figure 12:
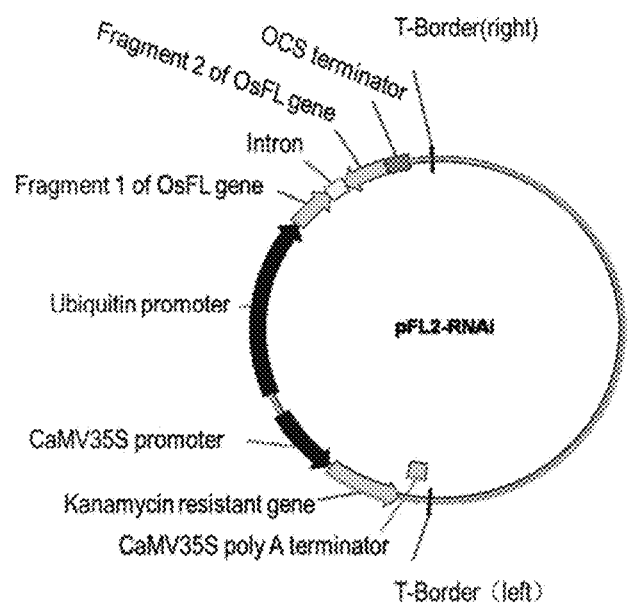
FIG. 12—depicts RNA interference vector of OsFL2 gene.

Example 7: Construction of OsFL2 Gene Expression Vector and Functional Analysis of the Gene Promoter The OsFL2 gene expression vector (FIG. 9) was constructed for the functional analysis of the gene promoter. First, the primer OsFL2-Pro-F (ggatccGGATTTCGAGGATCAAGCT, SEQ ID NO:37) and the primer OsFL2-Pro-R (gtcgacTTTCGCCGGGCAAATTCGC, SEQ ID NO:38) were used to amplify the 2520 bp promoter region upstream of OsFL2 gene (SEQ ID NO:3) from the wild type Huanghuazhan genomic DNA. The amplified product was digested by SalI and BamHI and ligated into a promoter detecting vector to obtain pOsFL2-pro vector (plasmid). The obtained pOsFL2-pro vector was transformed into wild-type rice callus by the *Agrobacterium*-mediated transformation method, and 12 transgenic rice plants were selected and regenerated. Expression pattern of OsFL2 promoter was analyzed by detecting the activity of p-galactosidase. GUS Staining in the root, stem, leaf and flower of the transgenic plants demonstrated that GUS gene driven by the promoter of OsFL2 gene was mostly expressed in anther of the rice (shown in FIG. I 0). In addition, functional analysis of the promoter shown as SEQ ID NO:9 linked to GUS showed that the staining result of SEQ ID NO:9 was consistent with the staining result of SEQ ID NO:3, and they were both an[o]]ther-specific promoters.

Example 8: Complementation Test of the Rice Male Sterile Mutant (Osf/2)

To confirm that the OsFL2 mutation was responsible for the male sterile phenotype in the mutant, a complementation vector containing the full-length wild type OsFL2 gene was constructed and transformed into plants to complement the Osjl2 phenotype. Specifically, the full-length genomic fragment from 2500 bp bases upstream of OsFL2 initiation codon ATG to approximate 497 bp bases downstream of OsFL2 termination codon TGA (SEQ ID NO:4), was amplified using the primer OsFL2-Res-F (gtttaaacGGATTTCGAGGATCAAGCT, SEQ ID NO:39) and the primer OsFL2-Res-R (ggatccACCCTGCATTTTTTATGCC, SEQ ID NO:40). The fragment was digested by PmeI and BamHI and ligated into a complementation vector to obtain pOsFL2-Res vector (plasmid). The obtained pOsFL2-Res vector was transformed into the callus induced from Huanghuazhan osfl2 mutant seeds by the *Agrobacterium*-mediated transformation method, and the transgenic plants were selected and regenerated. 8 positive transgenic plants were obtained and all of them showed restored fertility. This analysis further demonstrated OsFL2 gene was involved in pollen development regulation and the mutation in OsFL2 gene led to the non-pollen phenotype.

Example 9: Acquisition and Phenotypic Analysis of OsFL2 Gene RNAi Line

Figure 13:
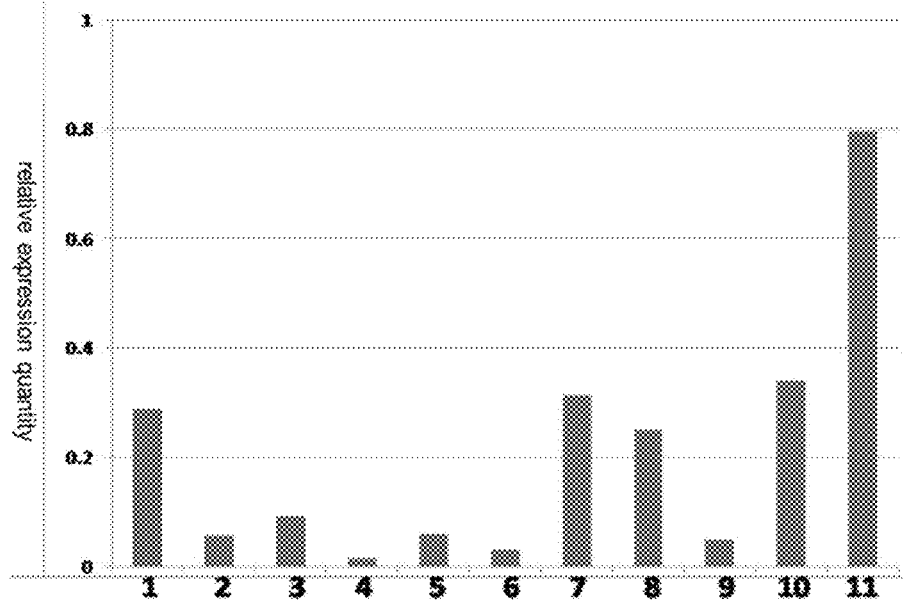
FIG. 13—depicts expression of OsFL2 gene in young panicle anther of transgenic plants with RNA interference vector, and 1-10 represent transgenic plants, 11 represents a wild-type plant.

To further confirm that disturbed expression of OsFL2 gene results in male sterility, an RNAi line to specifically knockout OsFL2 was constructed. Specifically, a 474 bp OsFL2 cDNA fragment was amplified using the primer OsFL2-Flag-F (GCGTCGCCGACAACCC, SEQ ID NO:41) and the primer OsFL2-Flag-R (TGGAGAAGGCCCGCGAC, SEQ ID NO:42). The amplified product was further amplified with two pairs of amplification primers to obtain a forward OsFL2 gene fragment 1 with a Kpnl site and a reverse OsFL2 gene fragment 2 with a BamHI site. The two fragments were digested, ligated, and incorporated into a pRNAi vector to obtain pOsFL2-RNAi. The obtained pOsFL2-RNAi was transformed into Nipponbare callus by the *Agrobacterium*-mediated transformation method, and 10 transgenic plants were selected and regenerated and the male fertility in 7 of the transgenic plants reduced significantly. Real-time quantitative PCR using the prime pair of example 6 based on OsFL2 and Actin cDNA was conducted to analyze expression level of OsFL2 gene in young anther at pollen mother cell meiosis stage and tetrad formation stage (P7) of the RNAi plants, and the result showed RNA expression level of OsFL2 gene of the transgenic sterile plants reduced significantly (FIG. 13). This analysis further demonstrated OsFL2 gene was involved in pollen development regulation and the mutation of OsFL2 gene led to non-pollen phenotype.

Example 10: Cross-Pollination Analysis of the OsFL2 Mutant Plant with the Restorer Line Huanghuazhan OsFL2 mutant plant may be cross-pollinated by several frequently-used restorer lines for the production of hybrid seeds. Hybrid seeds from some combinations showing obvious heterosis, demonstrating Huanghuazhan mutant is valuable in hybrid-breeding and can be used as a candidate material for the sterile line. Huanghuazhan OsFL2 mutant plant was crossed to several restorer lines, and that stigmas of the F2 generation sterile plant were still highly exposed (exposure rate of stigma was up to 60-88%) demonstrated a linkage inheritance existing in the mutant gene and a stigma exposure trait. High exposure of stigma was beneficial to cross-pollination and improved efficiency of hybrid seed production.

Figure 14:
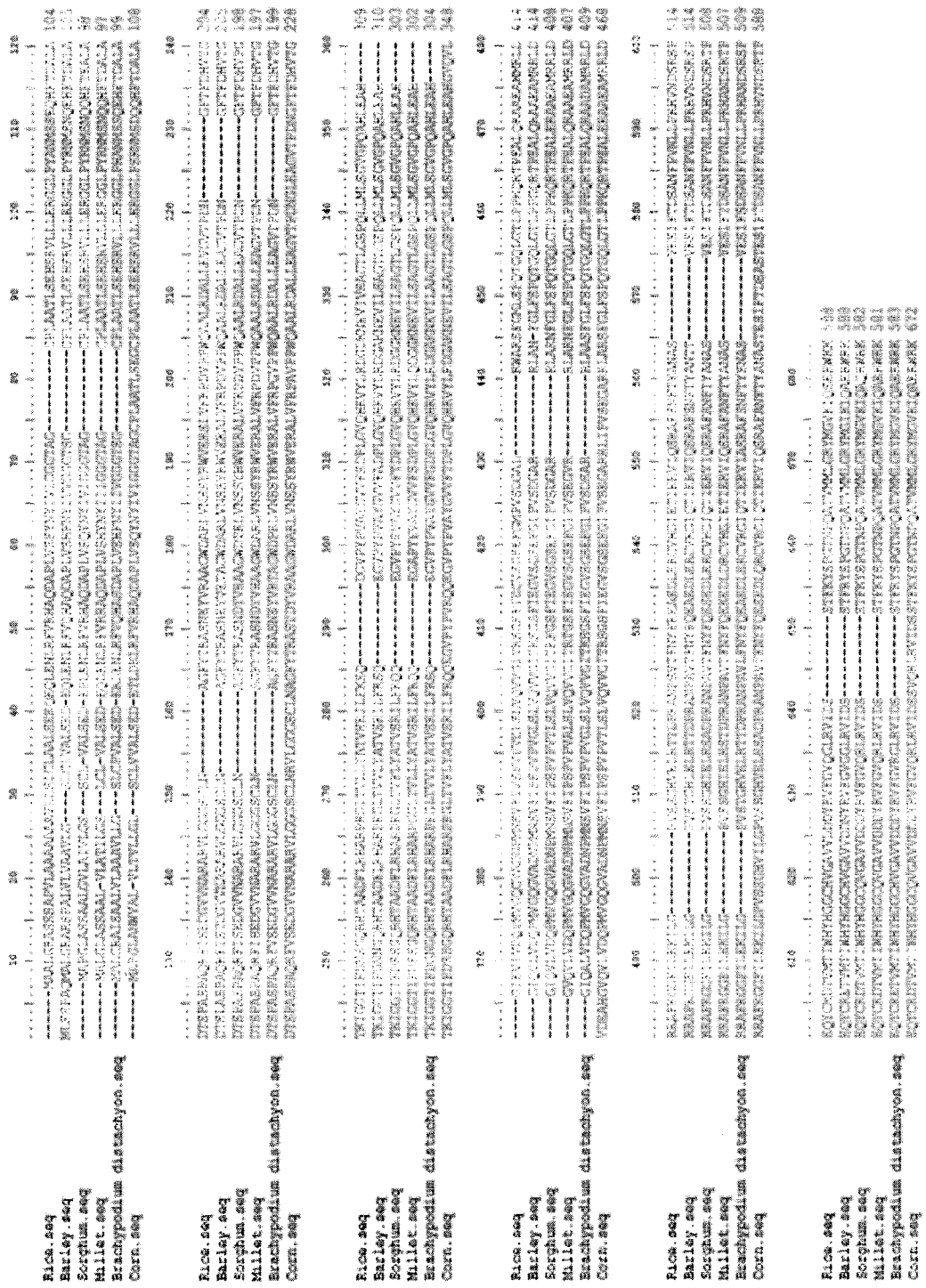
FIG. 14—Alignment of protein sequences encoded by rice OsFL2 gene (SEQ ID NO: 8) and its homologous genes of barley (SEQ ID NO: 12), sorghum (SEQ ID NO: 15), millet (SEQ ID NO: 20), Brachypodium distachyon (SEQ ID NO: 23) and maize (SEQ ID NO: 18), respectively.

Example 11 Alignment of the OsFL2 Protein with the Predicted Protein Homologues from Barley, Sorghum and Maize In NCBI database, using protein blast, the complete rice OsFL2 protein sequence was used as the query to search in the protein database for its protein homologues in the genomes of barley, sorghum, maize, millet and *Brachypodium distachyon*. The obtained protein sequences were aligned, and the result showed that they were highly homologous with each other (FIG. 14), indicating that the homologous protein has a conserved biological function and plays an important role in the development of male fertility of the plant.

Herein, the nucleotide sequence of the fertility gene of barley was shown as SEQ ID NO:10 or 11, and the amino acid sequence of the fertility gene of barley was shown as SEQ ID NO:12, the nucleotide sequence of the fertility gene of sorghum was shown as SEQ ID NO:13 or 14, and the amino acid sequence of the fertility gene of sorghum was shown as SEQ ID NO:15, the nucleotide sequence of the fertility gene ZmFL2 of maize was shown as SEQ ID NO:16 or 17, and the amino acid sequence of the fertility gene ZmFL2 of maize was shown as SEQ ID NO:18, the nucleotide sequence of the fertility gene of millet was shown as SEQ ID NO:19, and the amino acid sequence of the fertility gene of millet was shown as SEQ ID NO:20, the nucleotide sequence of the fertility gene of *Brachypodium distachyon* was shown as SEQ ID NO:21 or 22, and the amino acid sequence of the fertility gene of *Brachypodium distachyon* was shown as SEQ ID NO: 23.

Example 12: The Application of OsFL2 Gene in the Innovation of a New Hybrid Breeding Technique OsFL2 gene may be applied in new generation of hybrid breeding technique, and the core idea of the technique was: the recessive rice nuclear male sterile mutant was used as the transformation acceptor material, and three closely-linked genes were transformed into the sterile mutant. Therefore, a fertility-recovering gene can recover the fertility of the transformation acceptor, an pollen-inactivation gene can inactivate pollen containing the transgene, a color-label gene can be used for sorting of a transgenic seed from a non-transgenic seed, and the sorted non-transgenic seed was used as the sterile line, while the transgenic seed was used as the maintainer line. The maintainer line may pollinate the sterile line to propagate the sterile line, while the maintainer line can self-pollinate. As the technique utilizes biotechnology to produce a non-transgenic product, the bottleneck problem in the rice hybrid seed production is solved, especially the low resource utilization of three-line method and the instability of the sterile line of two-line method.

Based on the above-mentioned principle, the inventors used the OsFL2 gene of the rice to construct the expression vector pZN3. Before constructing the rice expression vector, the inventors firstly transformed each of the three expression cassettes, Zm-PA, OsFL2 and RFP, into the rice plant respectively and further verified the function of each expression cassette. The result indicated that each expression cassette can work well as initially designed when transformed into the rice alone.

Figure 15:
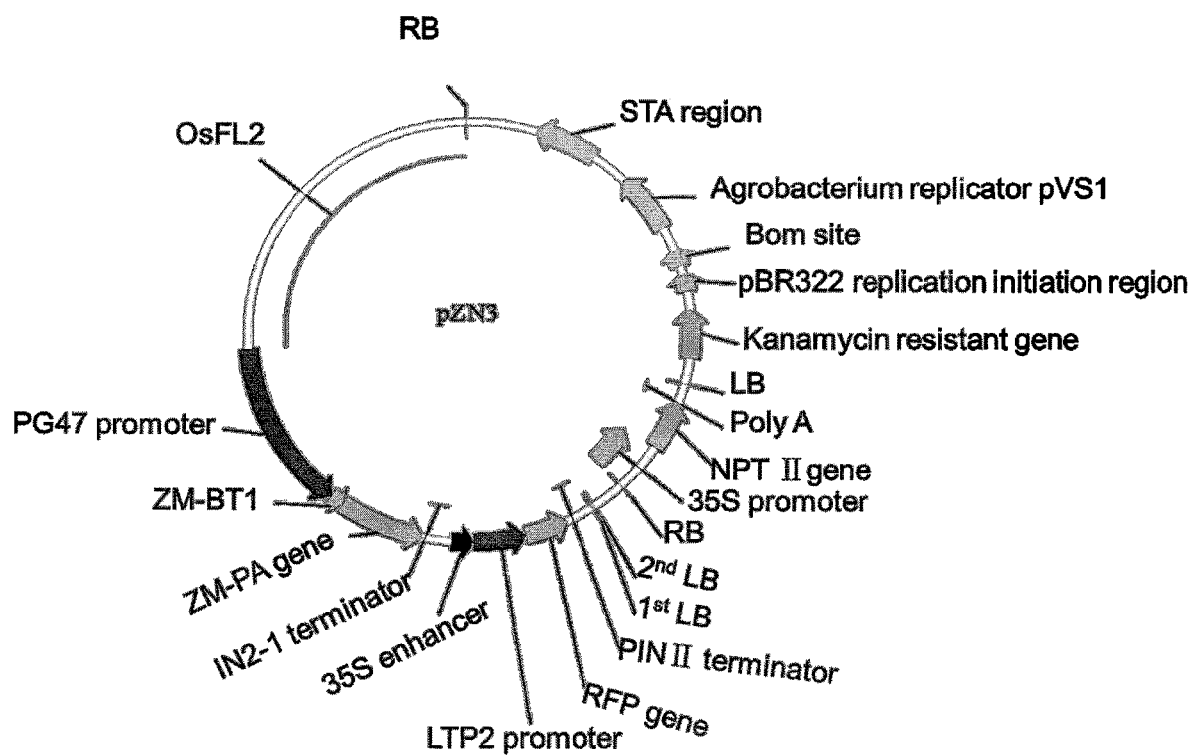
FIG. 15 depicts pZN3 vector.

Further, the inventor constructed pZN3 vector depicted in FIG. 15 by assembling the following DNA elements:

1) pCAMBIA2300 vector as the backbone;

2) expression cassette LTP2:RFP(r)-PINI1, an open reading frame of RFP(r) gene (SEQ ID NO:24) were linked between the promoter of LTP2 (SEQ ID NO:25) and the terminator of PINII (SEQ ID NO: 26) to recombine the expression cassette of RFP(r) (LTP2:RFP(r):PINI1), 3) OsFL2 expression cassette that comprises the full length of OsFL2 from the gene promoter to the gene terminator as SEQ ID NO:27. The complete nucleotide sequence between the promoter and the terminator of marker gene of OsFL2 gene was SEQ ID NO:4, and the promoter of OsFL2 gene was SEQ ID NO:3, the terminator of OsFL2 gene was SEQ ID NO:28, the genomic DNA sequence of OsFL2 gene was SEQ ID NO:27, the amino acid sequence of the protein encoded by the nucleotide sequence was SEQ ID NO: 2, 4) expression cassette of PG47:ZM-BT1:ZM-PA:IN2-1, the open reading frame of the pollen-inactivation gene ZM-PA (the nucleotide sequence was SEQ ID NO:29) was linked to the promoter of PG47 (the nucleotide sequence was SEQ ID NO:30), the downstream region of a transit peptide of ZM-BT1 (the nucleotide sequence was SEQ ID NO: 31), the upstream region of the terminator of IN2-1 (the nucleotide sequence was SEQ ID NO:32).

Rice transformation: plasmid pZN3 was transformed into Ag10 strain of *Agrobacterium* by electroporation, and the genetic transformation was carried out on the rice callus of Huanghuazhan homozygous for the recessive male sterile OsFL2 mutation through *Agrobacterium*-mediated transformation. 26 independent single-copy transgenic plants were obtained. The specific transformation acceptor material was obtained through the following process: Huanghuazhan seed homozygous for the OsFL2 recessive mutation was distinguished from the heterozygous seed by HRM (high resolution melting), and the callus of the homozygous Osfl2 mutant seed was induced and transformed.

Figure 16:
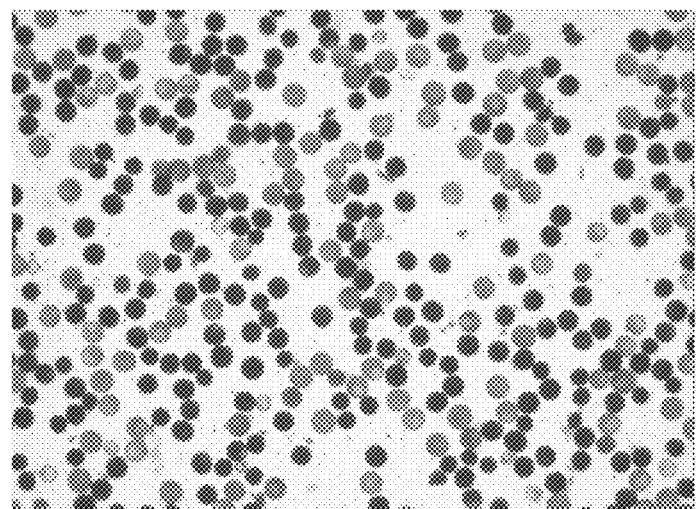
FIG. 16 shows fertile pollen grains and sterile pollen grains after dye-staining.

Examination of the pollen fertility of the transgenic rice plant: 26 obtained single-copy transgenic rice (with the homozygous OsFL2 recessive sterile site) were analyzed and it was found that there was no significant morphological difference between the transgenic plant and the non-transgenic plant, while the fertility was significantly different. Analysis of pollen stainability was carried out on the transgenic plant described above, using the wild-type rice as the control (FIG. 16). The adopted method included: drawing a single plant randomly from the transgenic rice and the wild-type rice as a control plant respectively in a flowering period, picking a flower respectively from either of the obtained single plant and getting an anther respectively from the obtained flowers, then placing the obtained anther respectively in the centre of a glass slide and adding a drop of 1% 12-KI solution, using a tweezer and a dissecting needle to release pollen, then the glass slide was covered with a cover slip. The sample was observed under a microscope to count the stained pollen number and the total pollen number. The pollen stained blue-black represented the fertile pollen while the pollen stained lightly represented aborted pollen (FIG. 16 depicts the fertile pollen grains and the sterile pollen grains after staining). Pollen stainability of the transgenic rice was analyzed, and the result showed that the stainable pollen of the control plant is about 98%-100% while the ratio between the normal pollen (stainable) and the aborted pollen (non-stainable) was approximate 1:1 in transgenic plants. The result indicated that the constructed maintainer line can produce equal amount of pollen grains with the exogenous gene and without the exogenous gene, i.e. the pZN3 construct made 50% of the pollen of the transgenic plant inactive. The result indicated that the vector provided in the present disclosure is able to inactivate the pollen as expected.

Figure 17:
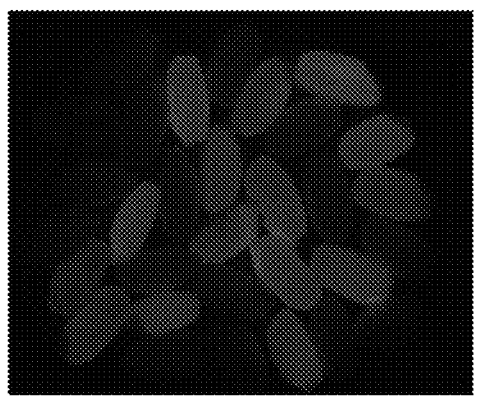
FIG. 17 depicts fluorescence segregation ratio analysis of seeds harvested from transgenic plants, and the segregation ratio of the seeds is 1:1.

Segregation analysis of fluorescent seeds and non-fluorescent seeds of the transgenic rice plant: the ratio of fluorescent segregation of the Tl generation seeds from 26 obtained single copy-transgenic rice (with the homozygous OsFL2 recessive sterile site) described above was analyzed, and the result indicated the segregation ratio of these seeds was 1:1 (FIG. 17), i.e. the segregation ratio between the fluorescent seed with the transgene and the non-fluorescent seed without the transgene was 1:1. The result also indicated the elements in the vector as a combination provided in the present disclosure expressed well and can be used toward creating and breeding the sterile line as well as the maintainer line. Then, OsFL2 gene can recover the fertility of the male sterile mutant acceptor, and the expression of Zm-PA gene and RFP gene can be used to inactivate pollen and for seed selection, respectively.

What is claimed is:

1. An expression vector comprising:
   a regulatory region sequence selected from SEQ ID NO: 3 and SEQ ID NO: 9; and
   a heterologous nucleotide sequence,
   wherein said regulatory region sequence is operably linked to the heterologous nucleotide sequence.

2. A plant cell comprising the expression vector of claim 1.

3. The expression vector of claim 1, wherein the vector further comprises a promoter operably linked to a nucleotide sequence encoding a selection marker, wherein the promoter is selected from the group consisting of Ubi promoter, CaMV35S promoter, Actin promoter and 5126 promoter.

4. A plant cell comprising the expression vector of claim 3.

5. The expression vector of claim 1, wherein the heterologous nucleotide sequence comprises SEQ ID NO:1 or 5.

6. A plant cell comprising the expression vector of claim 5.

7. A method for specifically expressing a heterologous nucleotide sequence in male tissue of a plant, comprising:
   introducing the expression vector of claim 1 into the plant; and
   expressing the heterologous nucleotide sequence in the male tissue of the plant.

8. The method of claim 7, wherein the heterologous nucleotide sequence comprises SEQ ID NO:1 or 5.

9. The method of claim 7, wherein the plant is a monocotyledon.

10. The method of claim 9, wherein the monocotyledon is a gramineous plant.

11. The method of claim 10, wherein the gramineous plant is rice, maize, sorghum, barley, millet or *Brachypodium distachyon*.

* * * * *

SEQUENCE LISTING

<160> NUMBER OF SEQ ID NOS: 42

<210> SEQ ID NO 1
<211> LENGTH: 1767
<212> TYPE: DNA
<213> ORGANISM: Oryza sativa

<400> SEQUENCE: 1

```
atggcagcac ttggccgcgc gagctcgtcg gcgccggtgc ttgccgccgc cgccgccgcc      60
gccgtgctcc tctcgctctg cctcgccgcg ctctcggaag agcaagagca actggagaac     120
ctgcggttcg tgcggcacgc gcaggacgcg ccgctggtgt cgagctacaa ctacatcgtc     180
atcggcggcg gcacggcggg gtgcccgctg gcggcgacgc tgtcggagca ctcgcgcgtg     240
ctgctgctgg agcgcggcgg cctgccgtac gccaacatgt cgagcgagca gcacttcacg     300
gacgcgctgg ccgacacgtc gccggcgtcg ccggcgcagc ggttcatctc ggaggacggc     360
gtggtgaacg cccgggcgcg ggtgctcggc ggcgggagct gcctcaacgc cgggttctac     420
acgcgggcga gcaacgagta cgtgcgcgcc gccgggtggg acgcgcggct ggtgaactcg     480
tcgtaccggt gggtggagcg ctcgctggtg ttccgcccg acgtgccgcc gtggcaggcg      540
gcgctccgcg acgcgctgct cgaggtcggc gtcacgcccg acaacggctt caccttcgac     600
cacgtcaccg gcaccaagat cggcggcacc atcttcgaca actccggcca gcgccacacc     660
gccgccgact tcctccgcca cgcccgcccc cgcggcctca ccgtcctcct ctacgccacc     720
gtctcccgta tcctcttcaa aagccaagac ggggtgccgt acccggtggc gtacggggtg     780
gtgttctcgg acccgctggg ggtgcagcac cgggtgtacc tccgcgacgg cgacaagaac     840
gaggtgatcg tgtcggcggg gacgctgggg agcccgcagc tgctgatgct gagcggcgtc     900
gggccgcagg cgcacctgga ggcgcacggc atcgaggtga tcgtggacca acccatggtc     960
gggcagggcg tcgccgacaa cccgatgaac tcggtgttca tcccgtcgcc ggtgccggtg    1020
gagctctccc tggtgcaggt cgtcggcatc acccgctccg gcagcttcat cgaggggtg    1080 agcgggtcgg agttcggcat gccggtgtcg gacggcgcgc tccggtgggc gcgcagcttc    1140
gggatgctgt cgccgcagac ggggcagctc ggcacgctgc cgccgaagca gaggacgccg    1200
gaggcgctgc agcgggcggc ggaggcgatg atgcggctgg acaggagggc gttccgggga    1260
ggcttcatcc tggagaagat cctcgggccg gtgtcctccg gccacgtcga gctgcgaacc    1320
accgacccga gggcgaaccc gtcggtgacg ttcaactact ccgcgaggc ggaggatctg     1380 gagcggtgcg tccatggcat cgagacgatc gagcgggtga tccagtcgcg ggccttctcc    1440
aacttcacct acgccaacgc ctccgtcgag tccatcttca ccgattccgc caacttcccc    1500
gtcaacctgc tgccgcgcca tgtcaacgac tcgcgctcgc cggagcagta ctgcatggac    1560
accgtcatga ccatctggca ctaccacggc ggctgccatg tcggcgccgt cgtcgacgac    1620
gattaccggg tgttcggggt gcaggggctc agggtgatcg acagctccac cttcaagtac    1680
tcccccggca ccaaccctca ggccaccgtc atgatgctcg gcaggtatat gggtgtgaag    1740
attcagtccg agagatggaa gaaatga                                        1767
```

<210> SEQ ID NO 2
<211> LENGTH: 588
<212> TYPE: PRT

-continued

<213> ORGANISM: Oryza sativa

<400> SEQUENCE: 2

```
Met Ala Ala Leu Gly Arg Ala Ser Ser Ala Pro Val Leu Ala Ala
1               5                   10                  15

Ala Ala Ala Ala Ala Val Leu Leu Ser Leu Cys Leu Ala Ala Leu Ser
            20                  25                  30

Glu Glu Gln Glu Gln Leu Glu Asn Leu Arg Phe Val Arg His Ala Gln
                35                  40                  45

Asp Ala Pro Leu Val Ser Ser Tyr Asn Tyr Ile Val Ile Gly Gly Gly
            50                  55                  60

Thr Ala Gly Cys Pro Leu Ala Ala Thr Leu Ser Glu His Ser Arg Val
65                  70                  75                  80

Leu Leu Leu Glu Arg Gly Gly Leu Pro Tyr Ala Asn Met Ser Ser Glu
                85                  90                  95

Gln His Phe Thr Asp Ala Leu Ala Asp Thr Ser Pro Ala Ser Pro Ala
                100                 105                 110

Gln Arg Phe Ile Ser Glu Asp Gly Val Val Asn Ala Arg Ala Arg Val
                115                 120                 125

Leu Gly Gly Gly Ser Cys Leu Asn Ala Gly Phe Tyr Thr Arg Ala Ser
            130                 135                 140

Asn Glu Tyr Val Arg Ala Ala Gly Trp Asp Ala Arg Leu Val Asn Ser
145                 150                 155                 160

Ser Tyr Arg Trp Val Glu Arg Ser Leu Val Phe Arg Pro Asp Val Pro
                165                 170                 175

Pro Trp Gln Ala Ala Leu Arg Asp Ala Leu Leu Glu Val Gly Val Thr
                180                 185                 190

Pro Asp Asn Gly Phe Thr Phe Asp His Val Thr Gly Thr Lys Ile Gly
                195                 200                 205

Gly Thr Ile Phe Asp Asn Ser Gly Gln Arg His Thr Ala Ala Asp Phe
            210                 215                 220

Leu Arg His Ala Arg Pro Arg Gly Leu Thr Val Leu Leu Tyr Ala Thr
225                 230                 235                 240

Val Ser Arg Ile Leu Phe Lys Ser Gln Asp Gly Val Pro Tyr Pro Val
                245                 250                 255

Ala Tyr Gly Val Val Phe Ser Asp Pro Leu Gly Val Gln His Arg Val
                260                 265                 270

Tyr Leu Arg Asp Gly Asp Lys Asn Glu Val Ile Val Ser Ala Gly Thr
            275                 280                 285

Leu Gly Ser Pro Gln Leu Leu Met Leu Ser Gly Val Gly Pro Gln Ala
            290                 295                 300

His Leu Glu Ala His Gly Ile Glu Val Ile Val Asp Gln Pro Met Val
305                 310                 315                 320

Gly Gln Gly Val Ala Asp Asn Pro Met Asn Ser Val Phe Ile Pro Ser
                325                 330                 335

Pro Val Pro Val Glu Leu Ser Leu Val Gln Val Val Gly Ile Thr Arg
                340                 345                 350

Ser Gly Ser Phe Ile Glu Gly Val Ser Gly Ser Glu Phe Gly Met Pro
            355                 360                 365

Val Ser Asp Gly Ala Leu Arg Trp Ala Arg Ser Phe Gly Met Leu Ser
            370                 375                 380

Pro Gln Thr Gly Gln Leu Gly Thr Leu Pro Pro Lys Gln Arg Thr Pro
385                 390                 395                 400
```

```
Glu Ala Leu Gln Arg Ala Ala Glu Ala Met Met Arg Leu Asp Arg Arg
            405                 410                 415

Ala Phe Arg Gly Gly Phe Ile Leu Glu Lys Ile Leu Gly Pro Val Ser
            420                 425                 430

Ser Gly His Val Glu Leu Arg Thr Thr Asp Pro Arg Ala Asn Pro Ser
            435                 440                 445

Val Thr Phe Asn Tyr Phe Arg Glu Ala Glu Asp Leu Glu Arg Cys Val
450                 455                 460

His Gly Ile Glu Thr Ile Glu Arg Val Ile Gln Ser Arg Ala Phe Ser
465                 470                 475                 480

Asn Phe Thr Tyr Ala Asn Ala Ser Val Glu Ser Ile Phe Thr Asp Ser
            485                 490                 495

Ala Asn Phe Pro Val Asn Leu Leu Pro Arg His Val Asn Asp Ser Arg
            500                 505                 510

Ser Pro Glu Gln Tyr Cys Met Asp Thr Val Met Thr Ile Trp His Tyr
            515                 520                 525

His Gly Gly Cys His Val Gly Ala Val Val Asp Asp Asp Tyr Arg Val
            530                 535                 540

Phe Gly Val Gln Gly Leu Arg Val Ile Asp Ser Ser Thr Phe Lys Tyr
545                 550                 555                 560

Ser Pro Gly Thr Asn Pro Gln Ala Thr Val Met Met Leu Gly Arg Tyr
            565                 570                 575

Met Gly Val Lys Ile Gln Ser Glu Arg Trp Lys Lys
            580                 585
```

<210> SEQ ID NO 3
<211> LENGTH: 2520
<212> TYPE: DNA
<213> ORGANISM: Oryza sativa

<400> SEQUENCE: 3

```
ggatttcgag gatcaagctc cagatctcga gcaaggcaag ccacctttga acatcttgag      60
cctatatttg aaatttaatt atgttgcttg aaaaatatta tgcattgata ggaccgcact     120
taatctgttg acccgtctgc aaggcagatt ggcggaccta cctaatttgt tgcatttgat     180
ccttcctttg ttaattgtta tatcatgtcc ccttgtaacc atctagttgc gtctcgatat     240
tcgtgcaccc tgtgcgagta tcgacggacg ccttcaaact aaaatctga ataacaactt      300
gggtaaaact tgggttttac aaaagacttg gaaaacccga cacctgggtc ggtgcttgcg     360
aactaaatga atttccaaaa ccgcggaccg ggaacgtac cgggtgtacg gtttcccgct      420
cttgcactta aggaccgttt ccttggaatt tcatctaaac ataagacaag tacgaccaca     480
tgggtggaat gggacacccc tggctgagta actagcttat caggggagcc ttgatgccga     540
gagacatgtg gattcgccgg ggtggtgtcg gggaggaccc ctgggcttcc tggcacagca     600
tggtctggga cctaacctgt tgttggtctg gacccctct cgtcagcata tggtaaacct      660
gtgtcggctt tcgaaatgcc ttgtcatgaa agcttggagg tctcccgacg tggctgatcc     720
ccacgggctg ggtgatccgg ttagtaatg tcgtgtgggt aaagtgtacc ccctctgcag      780
aggttaacaa actgtttgaa cagccgtgcc cacggtcatg gcggatgtg aggtgattcc      840
tagtgtagtt tgtttgact actgcttgtg aaattgctgt tgtggaaagg ggttcgatgt      900
ttgaaaaatc tgcagctgat aggatcagct aggcccgggt ggccgtttga agttgttgg      960
cccgggtggc cgttgaaaag ccgttggccg ggtgccaacc ttgattcatt tctaaagact    1020
gatacattgc acatactccg accggacgag acgcactgtc tcatccgtgt cgttgagaag    1080
```

```
cactcactta gttgttttta gaaaagagtt caaataaaat caattgcaaa acaacagtc     1140 ttttcttgaa gcctgcatta acacttatt tcccatggct tgctgagtac tcctgtactc     1200
acccttgctc tatataaata atccccccc agttgctgaa gaagatgaag cggaacctgc     1260
tgatgaggag ttcttccagg agcaagccgg ctacgatgag ttttagggtt tcggcctagt    1320
tcccaagtca cgcctgtgtt gtttggtcca agtcctggct tccgtttccc ttttgtaatg    1380
cagttgtgag ctcgggatct gtccgcagcc caacataact gtacctctac tctataataa    1440
agagacctct attgctgtga tattccgtct tcctgcgata ccagcactgt ttcctgggac    1500
tggtatcgat taacaggtta atttggagcg tcacgggcta attccggtcg gtactagttc    1560
ggggcgtgac aaaaacacaa aaaaagaaa ccaaccgtct taaaacttac aactttacca    1620
ttcggcaata caactgcaat gggccaagaa gttaatttaa agttaagagc aaattcattt    1680
ggaccacctt ttgttacaga tgcttcactt tggaccacat accacccatc tctcttctcg    1740
agcatgaaca atctcgatta cattggctcc tactcatcaa taaactctca catatatatg    1800
taaaaccatt catcggtata tgacaagtta tatatggata aaagagttga ggatgatcca    1860
aaatgtcaca aaggtaagaa taataaccgg tataaagtga aacatcgat aaacatcgct    1920 aataaaagtt cgtctatagt aaaatttact ctaaaattaa atcacctaat attttaatat    1980 tttttttgtac aaaatgaccg tttcaatggg gctttatcag atttagttga gatgcataca    2040
tggtaagcac cgtcataatc ttgcccaaga gctgacccaa ctcattaaaa ttacgcttct    2100
tttacgactt aataaatcaa gaagaaacca ttgaaatcca gcctgccccg actgtctcgt    2160
aacagaaaaa taactaagca acgactaaat tatgatttta aaatggcaaa aatatcaaag    2220
cacgttcgaa acaatcgcaa gattggcaag taaactctcc tgcttgcttg ctcacaacca    2280
catcagatca ttgatcaatg tttcatcagc tcatcacttc tgcatgcatg ttatattctt    2340
ctcagggctc ctccacaatt tacaaagctg ctcgaagatc ttctttgcag tgcaaagcaa    2400
tctgcaagat tattcaagac atctactctt gatctaccat tgagctaact ccggatatat    2460
aaacagaccg aacgtttcgt cccaggggaa tgtgaaagtt agcgaatttg cccggcgaaa    2520
```

<210> SEQ ID NO 4
<211> LENGTH: 5040
<212> TYPE: DNA
<213> ORGANISM: Oryza sativa

<400> SEQUENCE: 4

```
ggatttcgag gatcaagctc cagatctcga gcaaggcaag ccacctttga acatcttgag      60
cctatatttg aaatttaatt atgttgcttg aaaaatatta tgcattgata ggaccgcact     120
taatctgttg acccgtctgc aaggcagatt ggcggaccta cctaatttgt tgcatttgat     180
ccttcctttg ttaattgtta tatcatgtcc ccttgtaacc atctagttgc gtctcgatat     240
tcgtgcaccc tgtgcgagta tcgacggacg ccttcaaact taaaatctga ataacaactt     300
gggtaaaact tgggttttac aaaagacttg gaaaacccga cacctgggtc ggtgcttgcg    360
aactaaatga atttccaaaa ccgcggaccg gggaacgtac cgggtgtacg gtttcccgct    420
cttgcactta aggaccgttt ccttggaatt tcatctaaac ataagacaag tacgaccaca    480
tgggtggaat gggacacccc tggctgagta actagcttat caggggagcc ttgatgccga    540
gagacatgtg gattcgccgg ggtggtgtcg gggaggaccc ctgggcttcc tggcacagca    600
tggtctggga cctaacctgt tgttggtctg ggaccccctct cgtcagcata tggtaaacct    660
```

```
gtgtcggctt tcgaaatgcc ttgtcatgaa agcttggagg tctcccgacg tggctgatcc      720
ccacgggctg ggtgatccgg gttagtaatg tcgtgtgggt aaagtgtacc ccctctgcag      780
aggttaacaa actgtttgaa cagccgtgcc cacggtcatg ggcggatgtg aggtgattcc      840
tagtgtagtt ttgtttgact actgcttgtg aaattgctgt tgtggaaagg ggttcgatgt      900
ttgaaaaatc tgcagctgat aggatcagct aggcccgggt ggccgtttga aagttgttgg      960
cccgggtggc cgttgaaaag ccgttggccg ggtgccaacc ttgattcatt tctaaagact     1020
gatacattgc acatactccg accggacgag acgcactgtc tcatccgtgt cgttgagaag     1080
cactcactta gttgttttta gaaaagagtt caaataaaat caattgcaaa acaacagtc      1140 ttttcttgaa gcctgcatta aacacttatt tcccatggct tgctgagtac tcctgtactc     1200
acccttgctc tatataaata atccccccc agttgctgaa gaagatgaag cggaacctgc      1260
tgatgaggag ttcttccagg agcaagccgg ctacgatgag ttttagggtt tcggcctagt     1320
tcccaagtca cgcctgtgtt gtttggtcca agtcctggct tccgtttccc ttttgtaatg     1380
cagttgtgag ctcgggatct gtccgcagcc caacataact gtacctctac tctataataa     1440
agagacctct attgctgtga tattccgtct cctgcgata ccagcactgt ttcctgggac      1500
tggtatcgat taacaggtta atttggagcg tcacgggcta attccggtcg gtactagttc     1560
ggggcgtgac aaaaacacaa aaaaaagaaa ccaaccgtct taaaacttac aactttacca    1620
ttcggcaata caactgcaat gggccaagaa gttaatttaa agttaagagc aaattcattt     1680
ggaccacctt tgttacaga tgcttcactt tggaccacat accacccatc tctcttctcg      1740
agcatgaaca atctcgatta cattggctcc tactcatcaa taaactctca catatatatg     1800
taaaaccatt catcggtata tgacaagtta tatatggata aaagagttga ggatgatcca     1860
aaatgtcaca aaggtaagaa taataaccgg tataaagtga gaacatcgat aaacatcgct     1920
aataaaagtt cgtctatagt aaaatttact ctaaaattaa atcacctaat attttaatat     1980 tttttttgtac aaatggaccg tttcaatggg gctttatcag atttagttga gatgcataca    2040
tggtaagcac cgtcataatc ttgcccaaga gctgacccaa ctcattaaaa ttacgcttct     2100
tttacgactt aataaatcaa gaagaaacca ttgaaatcca gcctgccccg actgtctcgt     2160
aacagaaaaa taactaagca acgactaaat tatgatttta aaatggcaaa aatatcaaag     2220
cacgttcgaa acaatcgcaa gattggcaag taaactctcc tgcttgcttg ctcacaacca     2280
catcagatca ttgatcaatg tttcatcagc tcatcacttc tgcatgcatg ttatattctt     2340
ctcagggctc ctccacaatt tacaaagctg ctcgaagatc ttctttgcag tgcaaagcaa     2400
tctgcaagat tattcaagac atctactctt gatctaccat tgagctaact ccggatatat     2460
aaacagaccg aacgtttcgt cccaggggaa tgtgaaagtt agcgaatttg cccggcgaaa     2520
atggcagcac ttggccgcgc gagctcgtcg gcgccggtgc ttgccgccgc cgccgccgcc     2580
gccgtgctcc tctcgctctg cctcgccgcg ctctcggaag agcaaggtgc gtaaacgttg     2640
cgttgtatct ttgcgttgat gcgtgttgcg tcgtcgtcgt gttcatggcg tgcgatggcg     2700
ttgtgcagag caactggaga acctgcggtt cgtgcggcac gcgcaggacg cgccgctggt     2760
gtcgagctac aactacatcg tcatcggcgg cggcacggcg gggtgcccgc tggcggcgac     2820
gctgtcggag cactcgcgcg tgctgctgct ggagcgcggc ggcctgccgt acgccaacat     2880
gtcgagcgag cagcacttca cggacgcgct ggccgacacg tcgccggcgt cgccggcgca     2940
gcggttcatc tcggaggacg gcgtggtgaa cgcccgggcg cgggtgctcg gcggcggag      3000 ctgcctcaac gccgggttct acacgcgggc gagcaacgag tacgtgcgcg ccgccgggtg     3060
```

```
ggacgcgcgg ctggtgaact cgtcgtaccg gtgggtggag cgctcgctgg tgttccgccc    3120
cgacgtgccg ccgtggcagg cggcgctccg cgacgcgctg ctcgaggtcg gcgtcacgcc    3180
cgacaacggc ttcaccttcg accacgtcac cggcaccaag atcggcggca ccatcttcga    3240
caactccggc agcgccaca ccgccgccga cttcctccgc cacgcccgcc ccgcggcct     3300 caccgtcctc ctctacgcca ccgtctcccg tatcctcttc aaaagccaag gtacacagct    3360
acgatgaaaa tggaaaatgt gctgtgcgcc gaagaagctt gacctcacga cggcgagctt    3420
ttgccatggc gtgcagacgg ggtgccgtac ccggtggcgt acggggtggt gttctcggac    3480
ccgctggggg tgcagcaccg ggtgtacctc cgcgacggcg acaagaacga ggtgatcgtg    3540
tcggcgggga cgctggggag cccgcagctg ctgatgctga gcggcgtcgg gccgcaggcg    3600
cacctggagg cgcacggcat cgaggtgatc gtggaccaac ccatggtcgg gcagggcgtc    3660
gccgacaacc cgatgaactc ggtgttcatc ccgtcgccgg tgccggtgga gctctccctg    3720
gtgcaggtcg tcggcatcac ccgctccggc agcttcatcg aggggtgag cgggtcggag     3780 ttcggcatgc cggtgtcgga cggcgcgctc cggtgggcgc gcagcttcgg gatgctgtcg    3840
ccgcagacgg ggcagctcgg cacgctgccg ccgaagcaga ggacgccgga ggcgctgcag    3900
cgggcggcgg aggcgatgat gcggctggac aggagggcgt tccggggagg cttcatcctg    3960
gagaagatcc tcgggccggt gtcctccggc cacgtcgagc tgcgaaccac cgacccgagg    4020
gcgaacccgt cggtgacgtt caactacttc cgcgaggcgg aggatctgga gcggtgcgtc    4080
catggcatcg agacgatcga gcgggtgatc cagtcgcggg ccttctccaa cttcacctac    4140
gccaacgcct ccgtcgagtc catcttcacc gattccgcca acttccccgt caacctgctg    4200
ccgcgccatg tcaacgactc gcgctcgccg gagcagtact gcatggacac cgtcatgacc    4260
atctggcact accacggcgg ctgccatgtc ggcgccgtcg tcgacgacga ttaccgggtg    4320
ttcggggtgc aggggctcag ggtgatcgac agctccacct tcaagtactc ccccggcacc    4380
aaccctcagg ccaccgtcat gatgctcggc aggtaactgg catcattta gctcatgaaa    4440 gtgcattgcc atgagtaaca acacactaac agtatagttt tcaatatgga cactgggcag    4500
gtatatgggt gtgaagattc agtccgagag atggaagaaa tgatgaacaa agataatttt    4560
cgtttcagga gcaaaaaaat gcatgtaatt caaggaaaag aaaatgttca actgtctta    4620 gagtttagag tagattttat ttgcacccac ttaattttta ctcttctcta gacataggtt    4680
cagtatctgc ttgttgatta tgtaaccttg aagaagcatt gcaaaaacaa agcggaaact    4740
tatgttacca agggcatgac gaagaaataa atggattaga tttcattgac acttagaaaa    4800
tggaaccagc aaatcaaggc tgaaaataat tacactagaa acttatttta atggctttac    4860
atgtcgctac atacttaaat caatcaaagt tgctaccaaa gccatgttcc ctaaacagag    4920
ggttccgggc tctcaaacat tcttaatctt ctatacattg ataaaaagta tacataaaaa    4980
gaaaacctat taagatggaa atgttgaatt ctcttaagaa aggcataaaa aatgcagggt    5040
```

<210> SEQ ID NO 5
<211> LENGTH: 1761
<212> TYPE: DNA
<213> ORGANISM: Oryza sativa
<400> SEQUENCE: 5

```
atggcagcac ttggccgcgc gagctcgtcg gcgccggtgc ttgccgccgc cgccgccgtg      60
ctcctctcgc tctgcctcgc cgcgctctcg gaagagcaag agcaactgga gaacctgcgg     120
```

-continued

| | |
|---|---|
| ttcgtgcggc acgcgcagga cgcgccgctg gtgtcgagct acaactacat cgtcatcggc | 180 |
| ggcggcacgg cggggtgccc gctggcggcg acgctgtcgg agcactcgcg cgtgctgctg | 240 |
| ctggagcgcg gcggcctgcc gtacgccaac atgtcgagcg agcagcactt cacggacgcg | 300 |
| ctggccgaca cgtcgccggc gtcgccgacg cagcggttca tctcggagga cggcgtggtg | 360 |
| aacgcccggg cgcgggtgct cggcggcggg agctgcctca cgccgggtt ctacacgcgg | 420 |
| gcgagcaacg agtacgtgcg cgcctccggg tgggacgcgc ggctggtgaa ctcgtcgtac | 480 |
| cggtgggtgg agcgctcgct ggtgttccgc cccgacgtgc cgccgtggca ggcggcgctc | 540 |
| cgcgacgcgc tgctcgaggt cggcgtcacg cccgacaacg gcttcacctt cgaccacgtc | 600 |
| accggcacca agatcggcgg caccatcttc gacaactccg gccagcgcca caccgccgcc | 660 |
| gacttcctcc gccacgcccg ccccgcggc ctcaccgtcc tcctctacgc caccgtctcc | 720 |
| cgtatcctct tcaaaagcca agacggggtg ccgtacccgg tggcgtacgg ggtggtgttc | 780 |
| tcggacccgc tggggtgca gcaccggtg tacctccgcg acggcgacaa gaacgaggtg | 840 |
| atcgtgtcgg cggggacgct ggggagcccg cagctgctga tgctgagcgg cgtcgggccg | 900 |
| caggcgcacc tggaggcgca cggcatcgag gtgatcgtgg accaacccat ggtcgggcag | 960 |
| ggcgtcgccg acaacccgat gaactcggtg ttcatcccgt cgccggtgcc ggtggagctc | 1020 |
| tccctggtgc aggtcgtcgg catcacccgc tccggcagct tcatcgaggg ggtgagcggg | 1080 |
| tcggagttcg gcatgccggt gtcggacggc gcgctccggt gggcgcgcag cttcgggatg | 1140 |
| ctgtcgccgc agacggggca gctcggcacg ctgccgccga agcagaggac gccggaggcg | 1200 |
| ctgcagcggg cggcggaggc gatgatgcgg ctggacagga gggcgttccg gggaggcttc | 1260 |
| atcctggaga agatcctcgg gccggtgtcc tccggccacg tcgagctgcg aaccaccgac | 1320 |
| ccgagggcga accgtcggt gacgttcaac tacttccgcg aggcagagga tctgagcgg | 1380 |
| tgcgtccatg gcatcgagac gatcgagcgg gtgatccagt cgcgggcctt ctccaacttc | 1440 |
| acctacgcca acgcctccgt cgagtccatc ttcaccgatt ccgccaactt ccccgtcaac | 1500 |
| ctgctgccgc gccatgtcaa cgactcgcgc tcgccggagc agtactgcat ggacaccgtc | 1560 |
| atgaccatct ggcactacca cggcggctgc catgtcggcg ccgtcgtcga cgacgattac | 1620 |
| cgggtgttcg gggtgcaggg gctcagggtg atcgacagct ccaccttcaa gtactccccc | 1680 |
| ggcaccaacc ctcaggccac cgtcatgatg ctcggcaggt atatgggtgt gaagattcag | 1740 |
| tccgagagat ggaagaaatg a | 1761 |

<210> SEQ ID NO 6
<211> LENGTH: 586
<212> TYPE: PRT
<213> ORGANISM: Oryza sativa

<400> SEQUENCE: 6

Met Ala Ala Leu Gly Arg Ala Ser Ser Ser Ala Pro Val Leu Ala Ala
1               5                   10                  15

Ala Ala Ala Val Leu Leu Ser Leu Cys Leu Ala Ala Leu Ser Glu Glu
            20                  25                  30

Gln Glu Gln Leu Glu Asn Leu Arg Phe Val Arg His Ala Gln Asp Ala
        35                  40                  45

Pro Leu Val Ser Ser Tyr Asn Tyr Ile Val Ile Gly Gly Gly Thr Ala
    50                  55                  60

Gly Cys Pro Leu Ala Ala Thr Leu Ser Glu His Ser Arg Val Leu Leu
65                  70                  75                  80

-continued

```
Leu Glu Arg Gly Gly Leu Pro Tyr Ala Asn Met Ser Glu Gln His
             85                  90                  95

Phe Thr Asp Ala Leu Ala Asp Thr Ser Pro Ala Ser Pro Ala Gln Arg
            100                 105                 110

Phe Ile Ser Glu Asp Gly Val Val Asn Ala Arg Ala Arg Val Leu Gly
            115                 120                 125

Gly Gly Ser Cys Leu Asn Ala Gly Phe Tyr Thr Arg Ala Ser Asn Glu
            130                 135                 140

Tyr Val Arg Ala Ser Gly Trp Asp Ala Arg Leu Val Asn Ser Ser Tyr
145                 150                 155                 160

Arg Trp Val Glu Arg Ser Leu Val Phe Arg Pro Asp Val Pro Pro Trp
                165                 170                 175

Gln Ala Ala Leu Arg Asp Ala Leu Leu Glu Val Gly Val Thr Pro Asp
            180                 185                 190

Asn Gly Phe Thr Phe Asp His Val Thr Gly Thr Lys Ile Gly Gly Thr
            195                 200                 205

Ile Phe Asp Asn Ser Gly Gln Arg His Thr Ala Ala Asp Phe Leu Arg
            210                 215                 220

His Ala Arg Pro Arg Gly Leu Thr Val Leu Leu Tyr Ala Thr Val Ser
225                 230                 235                 240

Arg Ile Leu Phe Lys Ser Gln Asp Gly Val Pro Tyr Pro Val Ala Tyr
                245                 250                 255

Gly Val Val Phe Ser Asp Pro Leu Gly Val Gln His Arg Val Tyr Leu
            260                 265                 270

Arg Asp Gly Asp Lys Asn Glu Val Ile Val Ser Ala Gly Thr Leu Gly
            275                 280                 285

Ser Pro Gln Leu Leu Met Leu Ser Gly Val Gly Pro Gln Ala His Leu
            290                 295                 300

Glu Ala His Gly Ile Glu Val Ile Val Asp Gln Pro Met Val Gly Gln
305                 310                 315                 320

Gly Val Ala Asp Asn Pro Met Asn Ser Val Phe Ile Pro Ser Pro Val
                325                 330                 335

Pro Val Glu Leu Ser Leu Val Gln Val Val Gly Ile Thr Arg Ser Gly
            340                 345                 350

Ser Phe Ile Glu Gly Val Ser Gly Ser Glu Phe Gly Met Pro Val Ser
            355                 360                 365

Asp Gly Ala Leu Arg Trp Ala Arg Ser Phe Gly Met Leu Ser Pro Gln
            370                 375                 380

Thr Gly Gln Leu Gly Thr Leu Pro Pro Lys Gln Arg Thr Pro Glu Ala
385                 390                 395                 400

Leu Gln Arg Ala Ala Glu Ala Met Met Arg Leu Asp Arg Arg Ala Phe
                405                 410                 415

Arg Gly Gly Phe Ile Leu Glu Lys Ile Leu Gly Pro Val Ser Ser Gly
            420                 425                 430

His Val Glu Leu Arg Thr Thr Asp Pro Arg Ala Asn Pro Ser Val Thr
            435                 440                 445

Phe Asn Tyr Phe Arg Glu Ala Glu Asp Leu Glu Arg Cys Val His Gly
            450                 455                 460

Ile Glu Thr Ile Glu Arg Val Ile Gln Ser Arg Ala Phe Ser Asn Phe
465                 470                 475                 480

Thr Tyr Ala Asn Ala Ser Val Glu Ser Ile Phe Thr Asp Ser Ala Asn
                485                 490                 495

Phe Pro Val Asn Leu Leu Pro Arg His Val Asn Asp Ser Arg Ser Pro
```

|   |   | 500 |   |   |   | 505 |   |   |   | 510 |   |
|---|---|---|---|---|---|---|---|---|---|---|---|

Glu Gln Tyr Cys Met Asp Thr Val Met Thr Ile Trp His Tyr His Gly
                515                 520                 525

Gly Cys His Val Gly Ala Val Val Asp Asp Asp Tyr Arg Val Phe Gly
        530                 535                 540

Val Gln Gly Leu Arg Val Ile Asp Ser Ser Thr Phe Lys Tyr Ser Pro
545                 550                 555                 560

Gly Thr Asn Pro Gln Ala Thr Val Met Met Leu Gly Arg Tyr Met Gly
                565                 570                 575

Val Lys Ile Gln Ser Glu Arg Trp Lys Lys
                580                 585

<210> SEQ ID NO 7
<211> LENGTH: 1767
<212> TYPE: DNA
<213> ORGANISM: Oryza sativa

<400> SEQUENCE: 7

| atggcagcac | ttggccgcgc | gagctcgtcg | gcgccggtgc | ttgccgccgc | cgccgccgcc | 60 |
|---|---|---|---|---|---|---|
| gccgtgctcc | tctcgctctg | cctcgccgcg | ctctcggaag | agcaagagca | actggagaac | 120 |
| ctgcggttcg | tgcggcacgc | gcaggacgcg | ccgctggtgt | cgagctacaa | ctacatcgtc | 180 |
| atcggcggcg | gcacggcggg | gtgcccgctg | cggcgacgc | tgtcggagca | ctcgcgcgtg | 240 |
| ctgctgctgg | agcgcggcgg | cctgccgtac | gccaacatgt | cgagcgagca | gcacttcacg | 300 |
| gacgcgctgg | ccgacacgtc | gccggcgtcg | cggcgcagc | ggttcatctc | ggaggacggc | 360 |
| gtggtgaacg | cccgggcgcg | ggtgctcggc | ggcgggagct | gcctcaacgc | cgggttctac | 420 |
| acgcgggcga | gcaacgagta | cgtgcgcgcc | gccgggtggg | acgcgcggct | ggtgaactcg | 480 |
| tcgtaccggt | gggtggagcg | ctcgctggtg | ttccgccccg | acgtgccgcc | gtggcaggcg | 540 |
| gcgctccgcg | acgcgctgct | cgaggtcggc | gtcacgcccg | acaacggctt | caccttcgac | 600 |
| cacgtcaccg | gcaccaagat | cggcggcacc | atcttcgaca | actccggcca | gccacacc | 660 |
| gccgccgact | cctccgcca | cgcccgcccc | cgcggcctca | ccgtcctcct | ctacgccacc | 720 |
| gtctcccgta | tcctcttcaa | aagccaagac | ggggtgccgt | accggtggc | gtacggggtg | 780 |
| gtgttctcgg | accgctgggg | ggtgcagcac | cgggtgtacc | tccgcgacgg | cgacaagaac | 840 |
| gaggtgatcg | tgtcggcggg | gacgctgggg | agcccgcagc | tgctgatgct | gagcggcgtc | 900 |
| gggccgcagg | cgcacctgga | ggcgcacggc | atcgaggtga | tcgtggacca | acccatggtc | 960 |
| gggcagggcg | tcgccgacaa | cccgatgaac | tcggtgttca | tccgtcgcc | ggtgccggtg | 1020 |
| gagctctccc | tggtgcaggt | cgtcggcatc | acccgctccg | gcagcttcat | cgaggggtg | 1080 |
| agcgggtcg | agttcggcat | gccggtgtcg | acggcgcgc | tccggtgggc | gcgcagcttc | 1140 |
| gggatgctgt | cgccgcagac | ggggcagctc | ggcacgctgc | cgccgaagca | gaggacgccg | 1200 |
| gaggcgctgc | agcgggcggc | ggaggcgatg | atgcggctgg | acaggagggc | gttccggggga | 1260 |
| ggcttcatcc | tggagaagat | cctcgggccg | gtgtcctccg | ccacgtcga | gctgcgaacc | 1320 |
| accgacccga | gggcgaaccc | gtcggtgacg | ttcaactact | ccgcgaggc | ggaggatctg | 1380 |
| gagcggtgcg | tccatggcat | cgagacgatc | gagcgggtga | tccagtcgcg | ggccttctcc | 1440 |
| aacttcacct | acgccaacgc | ctccgtcgag | tccatcttca | ccgattccgc | caacttcccc | 1500 |
| gtcaacctgc | tgccgcgcca | tgtcaacgac | tcgcgctcgc | cggagcagta | ctgcatggac | 1560 |
| accgtcatga | ccatctggca | ctaccacggc | ggctgccatg | tcggcgccgt | cgtcgacgac | 1620 |

```
gattaccggg tgttcggggt gcaggggctc aggtgatcg acagctccac cttcaagtac    1680
tcccccgaca ccaaccctca ggccaccgtc atgatgctcg caggtatat gggtgtgaag    1740 attcagtccg agagatggaa gaaatga                                        1767
```

<210> SEQ ID NO 8
<211> LENGTH: 588
<212> TYPE: PRT
<213> ORGANISM: Oryza sativa

<400> SEQUENCE: 8

```
Met Ala Ala Leu Gly Arg Ala Ser Ser Ser Ala Pro Val Leu Ala Ala
1               5                   10                  15

Ala Ala Ala Ala Val Leu Leu Ser Leu Cys Leu Ala Ala Leu Ser
            20                  25                  30

Glu Glu Gln Glu Gln Leu Glu Asn Leu Arg Phe Val Arg His Ala Gln
        35                  40                  45

Asp Ala Pro Leu Val Ser Ser Tyr Asn Tyr Ile Val Ile Gly Gly Gly
    50                  55                  60

Thr Ala Gly Cys Pro Leu Ala Ala Thr Leu Ser Glu His Ser Arg Val
65                  70                  75                  80

Leu Leu Leu Glu Arg Gly Gly Leu Pro Tyr Ala Asn Met Ser Ser Glu
                85                  90                  95

Gln His Phe Thr Asp Ala Leu Ala Asp Thr Ser Pro Ala Ser Pro Ala
            100                 105                 110

Gln Arg Phe Ile Ser Glu Asp Gly Val Val Asn Ala Arg Ala Arg Val
        115                 120                 125

Leu Gly Gly Gly Ser Cys Leu Asn Ala Gly Phe Tyr Thr Arg Ala Ser
    130                 135                 140

Asn Glu Tyr Val Arg Ala Ala Gly Trp Asp Ala Arg Leu Val Asn Ser
145                 150                 155                 160

Ser Tyr Arg Trp Val Glu Arg Ser Leu Val Phe Arg Pro Asp Val Pro
                165                 170                 175

Pro Trp Gln Ala Ala Leu Arg Asp Ala Leu Leu Glu Val Gly Val Thr
            180                 185                 190

Pro Asp Asn Gly Phe Thr Phe Asp His Val Thr Gly Thr Lys Ile Gly
        195                 200                 205

Gly Thr Ile Phe Asp Asn Ser Gly Gln Arg His Thr Ala Ala Asp Phe
    210                 215                 220

Leu Arg His Ala Arg Pro Arg Gly Leu Thr Val Leu Leu Tyr Ala Thr
225                 230                 235                 240

Val Ser Arg Ile Leu Phe Lys Ser Gln Asp Gly Val Pro Tyr Pro Val
                245                 250                 255

Ala Tyr Gly Val Val Phe Ser Asp Pro Leu Gly Val Gln His Arg Val
            260                 265                 270

Tyr Leu Arg Asp Gly Asp Lys Asn Glu Val Ile Val Ser Ala Gly Thr
        275                 280                 285

Leu Gly Ser Pro Gln Leu Leu Met Leu Ser Gly Val Gly Pro Gln Ala
    290                 295                 300

His Leu Glu Ala His Gly Ile Glu Val Ile Val Asp Gln Pro Met Val
305                 310                 315                 320

Gly Gln Gly Val Ala Asp Asn Pro Met Asn Ser Val Phe Ile Pro Ser
                325                 330                 335

Pro Val Pro Val Glu Leu Ser Leu Val Gln Val Val Gly Ile Thr Arg
            340                 345                 350
```

Ser Gly Ser Phe Ile Glu Gly Val Ser Gly Glu Phe Gly Met Pro
        355                 360                 365

Val Ser Asp Gly Ala Leu Arg Trp Ala Arg Ser Phe Gly Met Leu Ser
    370                 375                 380

Pro Gln Thr Gly Gln Leu Gly Thr Leu Pro Pro Lys Gln Arg Thr Pro
385                 390                 395                 400

Glu Ala Leu Gln Arg Ala Ala Glu Ala Met Met Arg Leu Asp Arg Arg
                405                 410                 415

Ala Phe Arg Gly Gly Phe Ile Leu Glu Lys Ile Leu Gly Pro Val Ser
            420                 425                 430

Ser Gly His Val Glu Leu Arg Thr Thr Asp Pro Arg Ala Asn Pro Ser
        435                 440                 445

Val Thr Phe Asn Tyr Phe Arg Glu Ala Glu Asp Leu Glu Arg Cys Val
    450                 455                 460

His Gly Ile Glu Thr Ile Glu Arg Val Ile Gln Ser Arg Ala Phe Ser
465                 470                 475                 480

Asn Phe Thr Tyr Ala Asn Ala Ser Val Glu Ser Ile Phe Thr Asp Ser
                485                 490                 495

Ala Asn Phe Pro Val Asn Leu Leu Pro Arg His Val Asn Asp Ser Arg
            500                 505                 510

Ser Pro Glu Gln Tyr Cys Met Asp Thr Val Met Thr Ile Trp His Tyr
        515                 520                 525

His Gly Gly Cys His Val Gly Ala Val Asp Asp Asp Tyr Arg Val
    530                 535                 540

Phe Gly Val Gln Gly Leu Arg Val Ile Asp Ser Ser Thr Phe Lys Tyr
545                 550                 555                 560

Ser Pro Asp Thr Asn Pro Gln Ala Thr Val Met Met Leu Gly Arg Tyr
                565                 570                 575

Met Gly Val Lys Ile Gln Ser Glu Arg Trp Lys Lys
            580                 585

<210> SEQ ID NO 9
<211> LENGTH: 949
<212> TYPE: DNA
<213> ORGANISM: Oryza sativa

<400> SEQUENCE: 9
aaaacacaaa aaaagaaac caaccgtctt aaaacttaca actttaccat tcggcaatac    60
aactgcaatg ggccaagaag ttaatttaaa gttaagagca aattcatttg gaccaccttt   120
tgttacagat gcttcacttt ggaccacata ccacccatct ctcttctcga gcatgaacaa   180
tctcgattac attggctcct actcatcaat aaactctcac atatatatgt aaaaccattc   240
atcggtatat gacaagttat atatggataa agagttgag gatgatccaa aatgtcacaa    300
aggtaagaat aataaccggt ataaagtgag aacatcgata acatcgcta ataaagttc    360 gtctatagta aaatttactc taaaattaaa tcacctaata ttttaatatt tttttgtaca   420
aatggaccgt tcaatgggg ctttatcaga tttagttgag atgcatacat ggtaagcacc    480
gtcataatct tgcccaagag ctgacccaac tcattaaaat tacgcttctt ttacgactta   540
ataaatcaag aagaaaccat tgaaatccag cctgccccga ctgtctcgta acagaaaaat   600
aactaagcaa cgactaaatt atgattttaa aatggcaaaa atatcaaagc acgttcgaaa   660
caatcgcaag attggcaagt aaactctcct gcttgcttgc tcacaaccac atcagatcat   720
tgatcaatgt ttcatcagct catcacttct gcatgcatgt tatattcttc tcagggctcc   780

```
tccacaattt acaaagctgc tcgaagatct tctttgcagt gcaaagcaat ctgcaagatt      840
attcaagaca tctactcttg atctaccatt gagctaactc cggatatata aacagaccga      900
acgtttcgtc ccaggggaat gtgaaagtta gcgaatttgc ccggcgaaa                 949
```

<210> SEQ ID NO 10
<211> LENGTH: 2285
<212> TYPE: DNA
<213> ORGANISM: Hordeum vulgare

<400> SEQUENCE: 10

```
acgatgaacc aagcaggccc ttagaaaaaa tatagtgcac gcgcaaaagc gtctcaagat       60
tggccagtaa accctcgcat ttgatatact ccttccgtct aaaaacaaag ctcatcactt      120
ttgcatttcg caaccaatgc actgcatttg atataaccat tccctttcta tagtaacaca      180
attttatggg ctcctcgcgg ctgttctttg cactgtaatt atttaacaca tctaccctcg      240 atctaccgc ttgctaactc caggtttata aaccaagcga acttttcgcg tccctgaagc       300
gtaaaggatg ctgagctcgc cggcgcaaat ggcacttggc cgcgcgagat cgccggcgct      360
ggtgctagtc gccgccgtcc ttggctcgct ctgcatcgtc gcactctcgg aggatggtgc      420
gtatgctcac ctgcatggtt tttctgggg gtttggacat cggctacgtg cgtgtgtgtt       480
ctgtcatgat cgttggacat tgtgatgacc aaaatggtgt gccgtgcgtg tgtgcagagc      540
aactggagaa cctgcggttc gtgcagcacg cgcaggacgc gccgctggtg tcgcacttca      600
actacatcgt ggtcggcggc ggcacgtccg ggtgcccgct ggcggcgacg ctgtcggagc      660
actcgcgggt gctcctgctg gagcgcgggg gcctccccta ccgcaacatg tcgaaccagg      720
agcacttcac ggacgcgctg gccgacacgt cgctggcgtc ccggcgcag cggttcatct       780 cgacggacgg cgtggtgaac gcgcgggcgc gggtgctggg cggcgggagc tgcctcaacg      840
ccgggttcta cacgcgggcc agcaacgagt acgtgcgcac ggccgggtgg acgccaggc       900 tggtgaactc gtcgtaccgg tgggtggagc gcgcgctggt gttccggccc gacgtgccgc      960
cgtggcaggc cgcgctccgg gacgcgctgc tggaggccgg cgtcaccccg gataacggat     1020
tcaccttcga ccacgtgacg gggaccaaga tcggcggcac catcttcgac aacaacgggc     1080
agcggcacac cgccgccgac ttcctccggc acgcccggcc gcgggggctc accgtggtgc     1140
tctacgccac ggtgtcgcgg atcctgttca ggagccagga gggggtgccg tacccggtgg     1200
cgtacggggt ggtgttcgcg gacccgctgg gggtgcagca ccgggtgtac ctccgggacg     1260
gggccaagaa cgaggtgatc ctgtcggcgg ggacgctggg gagcccgcag ctgctgatgc     1320
tgagcggcgt cggcccgcag gcgcacctgg aggcgcacgg catccaggtg ctggtggacc     1380
agcccatggt cggcagggc gtggccgaca accccatgaa ctcggtcttc atccgtcgc       1440 ccgtgcccgt ggggctctcc ctggtgcagg tggtcgggat caccaagtcc ggcagcttca     1500
tcgagggcgt gagcggctcc gagttcggca tccggtgtc ggacggcgcc cgccgcctcg      1560
ccaacttcgg cctcttctcg ccccagaccg ggcagctcgg cacgctgccg ccgggccaga     1620
ggacgccgga ggcgctgcag cgggcggcgg aggcgatgag gcggctggac cggcgggcgt     1680 tccgggggcgg cttcatcctg gagaagatcc tgggccggt gtcgacgggg cacatcgagc     1740
tgcgcaccac cgaccgcgc gccaacccgg ccgtcacctt caactacttc caggaggcgg     1800
aggacctgga gcggtgcgtg cggggggatcc agaccatcga gcgggtgatc cagtcgcgcg     1860
cattctccaa cttcacctac gccaacacca ccgtcgagtc catcttcacc gactcggcca     1920
```

| | |
|---|---|
| acttccccgt caaccttctg ccgcggcacg tcaacgactc ccgctcgccg gagcagtact | 1980 |
| gcagggagac cgtcatgacc atctggcact accacggcgg ctgccacgtc ggagccgtcg | 2040 |
| tcgacgacaa ctaccgggtg ttcggggtgg gggggctcag ggtcatcgac agctccacct | 2100 |
| tcaggtactc ccccggcacc aacccgcagg ccaccgtcat gatgctcggc aggtaaacac | 2160 |
| cagacccttg caattatact gatctgaatg aatgaactcg actaacacga acgttataaa | 2220 |
| tctggtatgt acaggtatat gggcataaag attcaggccg agagatggag gaaatgatat | 2280 |
| ttcag | 2285 |

<210> SEQ ID NO 11
<211> LENGTH: 1767
<212> TYPE: DNA
<213> ORGANISM: Hordeum vulgare

<400> SEQUENCE: 11

| | |
|---|---|
| atgctgagct cgccggcgca aatggcactt ggccgcgcga gatcgccggc gctggtgcta | 60 |
| gtcgccgccg tccttggctc gctctgcatc gtcgcactct cggaggatga gcaactggag | 120 |
| aacctgcggt tcgtgcagca cgcgcaggac gcgccgctgg tgtcgcactt caactacatc | 180 |
| gtggtcggcg gcgcacgtc cgggtgcccg ctggcggcga cgctgtcgga gcactcgcgg | 240 |
| gtgctcctgc tggagcgcgg gggcctcccc taccgcaaca tgtcgaacca ggagcacttc | 300 |
| acggacgcgc tggccgacac gtcgctggcg tccccgcgc agcggttcat ctcgacggac | 360 |
| ggcgtggtga acgcgcgggc gcgggtgctg ggcggcggga gctgcctcaa cgccgggttc | 420 |
| tacacgcggg ccagcaacga gtacgtgcgc acggccgggt gggacgccag gctggtgaac | 480 |
| tcgtcgtacc ggtgggtgga gcgcgcgctg tgttccggc ccgacgtgcc gccgtggcag | 540 |
| gccgcgctcc gggacgcgct gctggaggcc ggcgtcaccc cggacaacgg attcaccttc | 600 |
| gaccacgtga cggggaccaa gatcggcggc accatcttcg acaacaacgg gcagcggcac | 660 |
| accgccgccg acttcctccg gcacgcccgg ccgcggggc tcaccgtggt gctctacgcc | 720 |
| acggtgtcgc ggatcctgtt caggagccag gaggggtgc cgtacccggt ggcgtacggg | 780 |
| gtggtgttcg cggacccgct gggggtgcag caccgggtgt acctccggga cggggccaag | 840 |
| aacgaggtga tcctgtcggc ggggacgctg gggagcccgc agctgctgat gctgagcggc | 900 |
| gtcggcccgc aggcgcacct ggaggcgcac ggcatccagg tgctggtgga ccagcccatg | 960 |
| gtcgggcagg gcgtggccga caaccccatg aactcggtct tcatcccgtc gcccgtgccc | 1020 |
| gtggggctct ccctggtgca ggtggtcggg atcaccaagt ccggcagctt catcgagggc | 1080 |
| gtgagcggct ccgagttcgg catcccggtg tcggacggcg cccgccgcct cgccaacttc | 1140 |
| ggcctcttct cgccccagac cgggcagctc ggcacgctgc cgccgggcca ggagacgccg | 1200 |
| gaggcgctgc agcgggcggc ggaggcgatg aggcggctgg accggcgggc gttccggggc | 1260 |
| ggcttcatcc tggagaagat cctggggccg gtgtcgacgg gcacatcga gctgcgcacc | 1320 |
| accgacccgc gcgccaaccc ggccgtcacc ttcaactact ccaggaggc ggaggacctg | 1380 |
| gagcggtgcg tgcggggat ccagaccatc gagcgggtga tccagtcgcg cgcattctcc | 1440 |
| aacttcacct acgccaacac caccgtcgag tccatcttca ccgactcggc caacttcccc | 1500 |
| gtcaacctgc tgccgcggca cgtcaacgac tcccgctcgc cggagcagta ctgcagggag | 1560 |
| accgtcatga ccatctggca ctaccacggc ggctgccacg tcggagccgt cgtcgacgac | 1620 |
| aactaccggg tgttcggggt ggggggctc agggtcatcg acagctccac cttcaggtac | 1680 |
| tcccccggca ccaacccgca ggccaccgtc atgatgctcg gcaggtatat gggcataaag | 1740 | attcaggccg agagatggag gaaatga                                    1767

<210> SEQ ID NO 12
<211> LENGTH: 588
<212> TYPE: PRT
<213> ORGANISM: Hordeum vulgare

<400> SEQUENCE: 12

Met Leu Ser Ser Pro Ala Gln Met Ala Leu Gly Arg Ala Arg Ser Pro
1               5                   10                  15

Ala Leu Val Leu Val Ala Ala Val Leu Gly Ser Leu Cys Ile Val Ala
            20                  25                  30

Leu Ser Glu Asp Glu Gln Leu Glu Asn Leu Arg Phe Val Gln His Ala
        35                  40                  45

Gln Asp Ala Pro Leu Val Ser His Phe Asn Tyr Ile Val Val Gly Gly
    50                  55                  60

Gly Thr Ser Gly Cys Pro Leu Ala Ala Thr Leu Ser Glu His Ser Arg
65                  70                  75                  80

Val Leu Leu Glu Arg Gly Gly Leu Pro Tyr Arg Asn Met Ser Asn
                85                  90                  95

Gln Glu His Phe Thr Asp Ala Leu Ala Asp Thr Ser Leu Ala Ser Pro
            100                 105                 110

Ala Gln Arg Phe Ile Ser Thr Asp Gly Val Val Asn Ala Arg Ala Arg
        115                 120                 125

Val Leu Gly Gly Gly Ser Cys Leu Asn Ala Gly Phe Tyr Thr Arg Ala
    130                 135                 140

Ser Asn Glu Tyr Val Arg Thr Ala Gly Trp Asp Ala Arg Leu Val Asn
145                 150                 155                 160

Ser Ser Tyr Arg Trp Val Glu Arg Ala Leu Val Phe Arg Pro Asp Val
                165                 170                 175

Pro Pro Trp Gln Ala Ala Leu Arg Asp Ala Leu Leu Glu Ala Gly Val
            180                 185                 190

Thr Pro Asp Asn Gly Phe Thr Phe Asp His Val Thr Gly Thr Lys Ile
        195                 200                 205

Gly Gly Thr Ile Phe Asp Asn Asn Gly Gln Arg His Thr Ala Ala Asp
    210                 215                 220

Phe Leu Arg His Ala Arg Pro Arg Gly Leu Thr Val Val Leu Tyr Ala
225                 230                 235                 240

Thr Val Ser Arg Ile Leu Phe Arg Ser Gln Glu Gly Val Pro Tyr Pro
                245                 250                 255

Val Ala Tyr Gly Val Val Phe Ala Asp Pro Leu Gly Val Gln His Arg
            260                 265                 270

Val Tyr Leu Arg Asp Gly Ala Lys Asn Glu Val Ile Leu Ser Ala Gly
        275                 280                 285

Thr Leu Gly Ser Pro Gln Leu Leu Met Leu Ser Gly Val Gly Pro Gln
    290                 295                 300

Ala His Leu Glu Ala His Gly Ile Gln Val Leu Val Asp Gln Pro Met
305                 310                 315                 320

Val Gly Gln Gly Val Ala Asp Asn Pro Met Asn Ser Val Phe Ile Pro
                325                 330                 335

Ser Pro Val Pro Val Gly Leu Ser Leu Val Gln Val Gly Ile Thr
            340                 345                 350

Lys Ser Gly Ser Phe Ile Glu Gly Val Ser Gly Ser Glu Phe Gly Ile
        355                 360                 365

Pro Val Ser Asp Gly Ala Arg Arg Leu Ala Asn Phe Gly Leu Phe Ser
    370                 375                 380

Pro Gln Thr Gly Gln Leu Gly Thr Leu Pro Pro Gly Gln Arg Thr Pro
385                 390                 395                 400

Glu Ala Leu Gln Arg Ala Ala Glu Ala Met Arg Arg Leu Asp Arg Arg
                405                 410                 415

Ala Phe Arg Gly Gly Phe Ile Leu Glu Lys Ile Leu Gly Pro Val Ser
            420                 425                 430

Thr Gly His Ile Glu Leu Arg Thr Thr Asp Pro Arg Ala Asn Pro Ala
        435                 440                 445

Val Thr Phe Asn Tyr Phe Gln Glu Ala Glu Asp Leu Glu Arg Cys Val
    450                 455                 460

Arg Gly Ile Gln Thr Ile Glu Arg Val Ile Gln Ser Arg Ala Phe Ser
465                 470                 475                 480

Asn Phe Thr Tyr Ala Asn Thr Thr Val Glu Ser Ile Phe Thr Asp Ser
                485                 490                 495

Ala Asn Phe Pro Val Asn Leu Leu Pro Arg His Val Asn Asp Ser Arg
            500                 505                 510

Ser Pro Glu Gln Tyr Cys Arg Glu Thr Val Met Thr Ile Trp His Tyr
        515                 520                 525

His Gly Gly Cys His Val Gly Ala Val Val Asp Asp Asn Tyr Arg Val
    530                 535                 540

Phe Gly Val Gly Gly Leu Arg Val Ile Asp Ser Ser Thr Phe Arg Tyr
545                 550                 555                 560

Ser Pro Gly Thr Asn Pro Gln Ala Thr Val Met Met Leu Gly Arg Tyr
                565                 570                 575

Met Gly Ile Lys Ile Gln Ala Glu Arg Trp Arg Lys
            580                 585

<210> SEQ ID NO 13
<211> LENGTH: 1964
<212> TYPE: DNA
<213> ORGANISM: Sorghum bicolor

<400> SEQUENCE: 13
atggcgcctg ggcttgcgag ctcggccgcg ctggggggttt tggccatcgt tcttggctcc      60
tcgtgcctcg tcgcgctctc ggaggatggt cgtgccgtg ccggactgca tgccgtgaat       120
atggtcatgc gttttttgttt tcttttggat tttctgcact tctgcaaacg tctgaatcgg     180
tgcatggtca tatgtatgtg cagagccact ggagaacctg cggttcgttc gccacgcgca     240
ggacgcgccg ctggtgtcgc aatacaacta catcgtcatc ggcggcggca cggcgggctg     300
cccgctggcg cgacgctgt cggagcactc ccgcgtgctg ctcctggagc gcggaggcct      360 ccccctaccgc aacatgtcca accagcagca cttcacggag cgctggcgg acacgtcccc    420 ggcgtcgccc gcgcagcggt tcatctccga ggacggcgtg gtgaacgcgc gggcgcgggt    480
gctgggcggc gggagctgcc tcaacgccgg cttctacacg cgggccagca cgactacgt    540 gcgcgccgcc gggtgggaca cccgcctcgt caactcctcg taccactggg tggagcgcgc    600
gctcgtgttc cgcccggacg tgcccccatg gcaggccgcg ctccgcgacg cgctgctgga   660
ggccggcgtc accccgaca acggcttcac cttcgaccac gtcccgggca ccaagatcgg    720
cggcaccatc ttcgacagca gcgggcagcg gcacaccgcc gccgacttcc tccgccacgc   780 gcggccccagg ggcctcaccg tgttcctcta cgctaccgtc tcgaggatcc tcttcaggca   840

```
gcaagagggc gtgccgtacc cggtggcgta cggcgtggtg ttcacggacc cgctgggcgt    900
gcagcaccgg gtgtacctcc gcgacggcgg caagaacgag gtgatcctgt ccgcggggac    960
gctggggagc ccgcagctgc tgatgctgag cggcgtcgga ccgcaggcgc acctggaggc    1020
gcacggcatc caggtgctgg tcgaccagcc catggtcggg cagggcgtgg ccgacaaccc    1080
catgaactcg gtgttcatcc cgtcgccggt gcccgtcacg ctctcgctcg tgcaggtcgt    1140
cgggatcacc cggttcggca gcttcatcga gggcgtcagc ggctccgagt tcggcatccc    1200
cgtctccgac ggcgcccgcc gcctagctcg caacttcggc ctcttctctc tcaggtgtg    1260 gtcggtcggt ccggtcggtg cttcgttcca tactgacagc aacatagccg ccggaaatga    1320
aatgtactga ctactgacgg atcatcttgc ggcagaccgg gcagctgggc acgctgccgc    1380
cgaagcagag aaccccggag gctctggagc gggcggcgga ggcgatgcgg cggctggaca    1440
ggcgggcgtt ccggggcggc ttcatcctgg agaagatcct gggcccggtg tcgtcggggc    1500
acatcgagct gcggtccgcc gacccgcgcg cgaacccggc ggtgacgttc aactacttcc    1560
aggagtcgga ggacctggag cggtgcgtgc acggcatcca gacgatcgag cgggtgatcc    1620
agtcccgggc cttcgccaac ttcacctacg ccaacgcgtc cgtggagtcc atcttcaccg    1680
actccgccaa cttccccgtc aacctcctgc cgcggcacgt caacgactcc cggacgcccg    1740
agcagtactg cagggacacc gtcatgacca tctggcacta ccacggcgga tgccaggtcg    1800
gcgccgtcgt cgacgacgat taccgggtgt tcggcgtgca gcggctcagg gtgatcgaca    1860
gctccacgtt caagtactcc ccggggacca acccgcaggc caccgtcatg atgctcggaa    1920
ggtatatggg ggtgaaaatt caggcccaga gatggaggaa atga                     1964

<210> SEQ ID NO 14
<211> LENGTH: 1749
<212> TYPE: DNA
<213> ORGANISM: Sorghum bicolor

<400> SEQUENCE: 14
atggcgcctg ggcttgcgag ctcggccgcg ctgggggttt tggccatcgt tcttggctcc    60
tcgtgcctcg tcgcgctctc ggaggatgag ccactggaga acctgcggtt cgttcgccac    120
gcgcaggacg cgccgctggt gtcgcaatac aactacatcg tcatcggcgg cggcacggcg    180
ggctgcccgc tggcggcgac gctgtcggag cactcccgcg tgctgctcct ggagcgcgga    240
ggcctcccct accgcaacat gtccaaccag cagcacttca cggaggcgct ggcggacacg    300
tccccggcgt cgcccgcgca gcggttcatc tccgaggacg gcgtggtgaa cgcgcgggcg    360
cgggtgctgg gcgcgggag ctgcctcaac gccggcttct acacgcgggc cagcaacgac    420
tacgtgcgcg ccgccgggtg ggacaccgc ctcgtcaact cctcgtacca ctgggtggag    480
cgcgcgctcg tgttccgccc ggacgtgccc ccatggcagg ccgcgctccg cgacgcgctg    540
ctggaggccg cgtcacccc cgacaacggc ttcaccttcg accacgtccc gggcaccaag    600
atcggcggca ccatcttcga cagcagcggg cagcggcaca ccgccgccga cttcctccgc    660
cacgcgcggc ccaggggcct caccgtgttc ctctacgcta ccgtctcgag gatcctcttc    720
aggcagcaag agggcgtgcc gtaccgcgtg cgtacggcg tggtgttcac ggacccgctg    780
ggcgtgcagc accgggtgta cctccgcgac ggcggcaaga acgaggtgat cctgtccgcg    840 ggacgctgg ggagcccgca gctgctgatg ctgagcggcg tcggaccgca ggcgcacctg    900
gaggcgcacg gcatccaggt gctggtcgac cagcccatgg tcgggcaggg cgtggccgac    960
aaccccatga actcggtgtt catcccgtcg ccggtgcccg tcacgctctc gctcgtgcag    1020
```

-continued

```
gtcgtcggga tcacccggtt cggcagcttc atcgagggcg tcagcggctc cgagttcggc    1080
atccccgtct ccgacggcgc ccgccgccta gctcgcaact tcggcctctt ctctcctcag    1140
accgggcagc tgggcacgct gccgccgaag cagagaaccc cggaggctct ggagcgggcg    1200
gcggaggcga tgcggcggct ggacaggcgg gcgttccggg gcggcttcat cctggagaag    1260
atcctgggcc cggtgtcgtc ggggcacatc gagctgcggt ccgccgaccc gcgcgcgaac    1320
ccggcggtga cgttcaacta cttccaggag tcggaggacc tggagcggtg cgtgcacggc    1380
atccagacga tcgagcgggt gatccagtcc cgggccttcg ccaacttcac ctacgccaac    1440
gcgtccgtgg agtccatctt caccgactcc gccaacttcc ccgtcaacct cctgccgcgg    1500
cacgtcaacg actcccggac gcccgagcag tactgcaggg acaccgtcat gaccatctgg    1560
cactaccacg gcggatgcca ggtcggcgcc gtcgtcgacg acgattaccg ggtgttcggc    1620
gtgcagcggc tcagggtgat cgacagctcc acgttcaagt actccccggg gaccaacccg    1680
caggccaccg tcatgatgct cggaaggtat atgggggtga aaattcaggc ccagagatgg    1740
aggaaatga                                                            1749
```

<210> SEQ ID NO 15
<211> LENGTH: 582
<212> TYPE: PRT
<213> ORGANISM: Sorghum bicolor

<400> SEQUENCE: 15

```
Met Ala Pro Gly Leu Ala Ser Ser Ala Ala Leu Gly Val Leu Ala Ile
1               5                   10                  15

Val Leu Gly Ser Ser Cys Leu Val Ala Leu Ser Glu Asp Glu Pro Leu
            20                  25                  30

Glu Asn Leu Arg Phe Val Arg His Ala Gln Asp Ala Pro Leu Val Ser
        35                  40                  45

Gln Tyr Asn Tyr Ile Val Ile Gly Gly Thr Ala Gly Cys Pro Leu
    50                  55                  60

Ala Ala Thr Leu Ser Glu His Ser Arg Val Leu Leu Leu Glu Arg Gly
65                  70                  75                  80

Gly Leu Pro Tyr Arg Asn Met Ser Asn Gln Gln His Phe Thr Glu Ala
                85                  90                  95

Leu Ala Asp Thr Ser Pro Ala Ser Pro Ala Gln Arg Phe Ile Ser Glu
            100                 105                 110

Asp Gly Val Val Asn Ala Arg Ala Arg Val Leu Gly Gly Ser Cys
        115                 120                 125

Leu Asn Ala Gly Phe Tyr Thr Arg Ala Ser Asn Asp Tyr Val Arg Ala
    130                 135                 140

Ala Gly Trp Asp Thr Arg Leu Val Asn Ser Ser Tyr His Trp Val Glu
145                 150                 155                 160

Arg Ala Leu Val Phe Arg Pro Asp Val Pro Pro Trp Gln Ala Ala Leu
                165                 170                 175

Arg Asp Ala Leu Leu Glu Ala Gly Val Thr Pro Asp Asn Gly Phe Thr
            180                 185                 190

Phe Asp His Val Pro Gly Thr Lys Ile Gly Gly Thr Ile Phe Asp Ser
        195                 200                 205

Ser Gly Gln Arg His Thr Ala Ala Asp Phe Leu Arg His Ala Arg Pro
    210                 215                 220

Arg Gly Leu Thr Val Phe Leu Tyr Ala Thr Val Ser Arg Ile Leu Phe
225                 230                 235                 240
```

Arg Gln Gln Glu Gly Val Pro Tyr Pro Val Ala Tyr Gly Val Val Phe
                245                 250                 255

Thr Asp Pro Leu Gly Val Gln His Arg Val Tyr Leu Arg Asp Gly Gly
            260                 265                 270

Lys Asn Glu Val Ile Leu Ser Ala Gly Thr Leu Gly Ser Pro Gln Leu
        275                 280                 285

Leu Met Leu Ser Gly Val Gly Pro Gln Ala His Leu Glu Ala His Gly
    290                 295                 300

Ile Gln Val Leu Val Asp Gln Pro Met Val Gly Gln Gly Val Ala Asp
305                 310                 315                 320

Asn Pro Met Asn Ser Val Phe Ile Pro Ser Pro Val Pro Val Thr Leu
                325                 330                 335

Ser Leu Val Gln Val Val Gly Ile Thr Arg Phe Gly Ser Phe Ile Glu
            340                 345                 350

Gly Val Ser Gly Ser Glu Phe Gly Ile Pro Val Ser Asp Gly Ala Arg
        355                 360                 365

Arg Leu Ala Arg Asn Phe Gly Leu Phe Ser Pro Gln Thr Gly Gln Leu
    370                 375                 380

Gly Thr Leu Pro Pro Lys Gln Arg Thr Pro Glu Ala Leu Glu Arg Ala
385                 390                 395                 400

Ala Glu Ala Met Arg Arg Leu Asp Arg Arg Ala Phe Arg Gly Gly Phe
                405                 410                 415

Ile Leu Glu Lys Ile Leu Gly Pro Val Ser Ser Gly His Ile Glu Leu
            420                 425                 430

Arg Ser Ala Asp Pro Arg Ala Asn Pro Ala Val Thr Phe Asn Tyr Phe
        435                 440                 445

Gln Glu Ser Glu Asp Leu Glu Arg Cys Val His Gly Ile Gln Thr Ile
    450                 455                 460

Glu Arg Val Ile Gln Ser Arg Ala Phe Ala Asn Phe Thr Tyr Ala Asn
465                 470                 475                 480

Ala Ser Val Glu Ser Ile Phe Thr Asp Ser Ala Asn Phe Pro Val Asn
                485                 490                 495

Leu Leu Pro Arg His Val Asn Asp Ser Arg Thr Pro Glu Gln Tyr Cys
            500                 505                 510

Arg Asp Thr Val Met Thr Ile Trp His Tyr His Gly Gly Cys Gln Val
        515                 520                 525

Gly Ala Val Val Asp Asp Tyr Arg Val Phe Gly Val Gln Arg Leu
    530                 535                 540

Arg Val Ile Asp Ser Ser Thr Phe Lys Tyr Ser Pro Gly Thr Asn Pro
545                 550                 555                 560

Gln Ala Thr Val Met Met Leu Gly Arg Tyr Met Gly Val Lys Ile Gln
                565                 570                 575

Ala Gln Arg Trp Arg Lys
            580

<210> SEQ ID NO 16
<211> LENGTH: 2585
<212> TYPE: DNA
<213> ORGANISM: Zea mays

<400> SEQUENCE: 16
ctcacagcaa attcgtctca cgcatattcg tcatccagct ccgttaaaa tgcgtgctca      60 ttatccctca agcatgcata tactatatat gatgcagatc atatatgacc tttatacaat    120

```
tatcaccacc tcgattcctc gcggcacatc tttgcaccgc agaacgaccg tgcagtattt    180
tatacaaaca tctactctcg atctacccat gagctaactc caatatata agcgagccga    240 acttttctcc tatctgagca ctgctgctgc tgaaaatggc gcctgggctt gcgaactggg    300
tcgcgctggt tctgaccgtc ctccttggtc tctcgtgcct cgtcgtcgcg ctctcggagg    360
atggtttgtg ccggacttgt cacgcgctct ttggtatttc tgcagttctg caaacgtgtg    420
aattggcatg gacatgtgca gaaacactgg acaagctgcg gttcgtgcgc cacgcacagg    480
acgcgcccct ggtgtcgcag tacaactaca tcgtgatcgg cggcggcacg gcggggtgcc    540
cgctggcggc gacgctgtcg gagcactcgc gcgtgctgct cctggagcgc ggggcctcc    600 cgtcccgcaa catgtccgac cagcagcact tcacggacgc gctggcggac acgtccccgg    660
cgtcgcccgc gcagcggttc gtgtccgagg acggcgtggt gaacgcgcgg gcccgggtgc    720
tgggcggggg cagctgcctc aacgccgggt tctacacgcg ggccagcacc gactacgtgc    780
gcgccgccgg ctgggacgcc cgcctcgtca actcgtccta ccgctgggtg gagcgcgcgc    840
tcgtgttccg ccccgccgtg cccccgtggc aggccgcgcc ccgcgacgcg ctgctcgagg    900
ccggcgtcac gcccgacaac ggcttcacct tcgaccacgt cacgggcacc aagatcgggg    960
gcaccatctt cgacagcagc ggccagcgcc acccgccgc cgacttcctc cgccacgcgc    1020
gccccagggg gctcaccgtg ttcctctacg ctaccgtctc caggatcctc ttcagacagc    1080
aaggtacgta cgtgcgtgca cggcttccgc attttttttt cgacagtgcg ggctggcacg    1140
atcgcgctct gaagcggaga atcgtgcgct gtcgacagag ggcgtgccgt accggtggc    1200 gtacggtgtg gtgttcacgg acccgctcgg ggtgcagcac cgggtgtacc tccgggacgg    1260
cgccaagaac gaggtgatcc tgtcggcggg gacgctgggg agcccgcagc tgctgatgct    1320
gagcggcgtc ggcccgcagg cgcacctgga ggcgcacggc gtccaggtgc tggtggacca    1380
gcccatggtc gggcagggcg tggctgacaa cccgatgaac tcggtgttca tcccgtcgcc    1440
ggtgcccgtc acgctgtcgc tcgtgcaggt cgtcgggatc acccggtccg gcagcttcat    1500
cgagggcgtg agcggctccg agttcggcat ccccgtctcc gagggcgccc gtcgcctggc    1560
tcgcagcttc ggcctcttct ctccgcagac ggggcagctg gcacgttgc cgccgaagca    1620 gagaacccca gaggccctgg agcgcgcggc ggaggcgatg cggcggctgg acaggcgggc    1680
gttccggggc ggattcatcc tggagaagat cctgggcccc gtctcctcgg ccacgtcga    1740 gctgcggtcc gccgacccgc gcgcgaaccc ggcggtgacg ttcaactact ccaggagtc    1800 ggaggacctg cagcggtgcg tgcgcggcat ccagacgatc gagcgcgtga tccagtcccg    1860
ggccttcgcc aacttcacct acgccaacgc ttccacggag tccatcttca ccgactccgc    1920
caacttcccc gtcaacctcc tgccgcggca cgtcaacgac tcccggacgc ccgagcagta    1980
ctgcagggac accgtcatga ccatctggca ttaccacggc gggtgccagg tcggcgccgt    2040 cgtgacgac gattaccggg tgttcggcgt gcagcgactg agggtgatcg acagctccac    2100
gttcaagtac tccccggca ccaacccgca ggccaccgtc atgatgctcg aaggtatat    2160 gggtgtgaaa attcaggccg agagatggag gaaatgatcg agatttcaag tttcagcatg    2220
gtctagggac taggcctcta gctgtgataa tgaatatcaa tcaacacatc tgtaactggg    2280
taactgctct agcctctaga gtaggtttta ttttctcta gatatttttt taatctcctc    2340
tagacatact cctagcttcc gcatgttgtt ggttccattt caccacaccc ctagatgcat    2400
tgttcagcat ttcgcgggaa taatgagaat tatgctgaaa aggcatgatc gctcctcctg    2460
cctattctac agaaaattaa ataaagaacc gccatttcat caaataaacc aaaggccgtg    2520
```

|  |  |
|---|---|
| ttctgtggat tggaagggat cgaggaagat taaatcgttt ctatttaatt ttcccttaat | 2580 |
| tttaa | 2585 |

<210> SEQ ID NO 17
<211> LENGTH: 2242
<212> TYPE: DNA
<213> ORGANISM: Zea mays

<400> SEQUENCE: 17

|  |  |
|---|---|
| atggcgcctg ggcttgcgaa ctgggtcgcg ctggttcgcg ctggttctga ccgtcctcct | 60 |
| tggtctctcg tgcctcgtcg tcgcgctctc ggaggatggt ttgtgatggt ttgtgccgga | 120 |
| cttgtcacgc gctctttggt atttctgcag ttctgcaaac gtgtgaattg catgaattg | 180 |
| gcatggacat gtgcagaaac actggacaag ctgcggttcg tgcgccacgc acaggacgcg | 240 |
| cccctacgcg cccctggtgt cgcagtacaa ctacatcgtg atcggcggcg gcacggcggg | 300 |
| gtgcccgctg gcgccgctg gcggcgacgc tgtcggagca ctcgcgcgtg ctgctcctgg | 360 |
| agcgcggggg cctcccgtcc cgcaacgtcc cgcaacatgt ccgaccagca gcacttcacg | 420 |
| gacgcgctgg cggacacgtc cccggcgtcg cccgccgtcg cccgcgcagc ggttcgtgtc | 480 |
| cgaggacggc gtggtgaacg cgcgggcccg ggtgctgggc gggggtgggc ggggggcagct | 540 |
| gcctcaacgc cggggttctac acgcgggcca gcaccgacta cgtgcgcgcc gccgggcgcc | 600 |
| gccggctggg acgcccgcct cgtcaactcg tcctaccgct gggtggagcg cgcgctcgtg | 660 |
| ttccgtcgtg ttccgccccg ccgtgccccc gtggcaggcc gcgctccgcg acgcgctgct | 720 |
| cgaggccggc gtcacccggc gtcacgcccg acaacggctt caccttcgac cacgtcacgg | 780 |
| gcaccaagat cggggggcacc atcttgcacc atcttcgaca gcagcggcca gcgccacacc | 840 |
| gccgccgact tcctccgcca cgcgcgcccc aggggggcccc aggggggctca ccgtgttcct | 900 |
| ctacgctacc gtctccagga tcctcttcag acagcaaggt acgtaaaggt acgtacgtgc | 960 |
| gtgcacggct tccgcatttt ttttttcgaca gtgcgggctg gcacgatcgc gctctatcgc | 1020 |
| gctctgaagc ggagaatcgt gcgctgtcga cagagggcgt gccgtacccg gtggcgtacg | 1080 |
| gtgtggtacg gtgtggtgtt cacggacccg ctcggggtgc agcaccgggt gtacctccgg | 1140 |
| gacggcgcca agaaccgcca agaacgaggt gatcctgtcg gcggggacgc tggggagccc | 1200 |
| gcagctgctg atgctgagcg gcgtcgagcg gcgtcggccc gcaggcgcac ctggaggcgc | 1260 |
| acggcgtcca ggtgctggtg gaccagccca tggtcgccca tggtcgggca gggcgtggct | 1320 |
| gacaacccga tgaactcggt gttcatcccg tcgccggtgc ccgtcggtgc ccgtcacgct | 1380 |
| gtcgctcgtg caggtcgtcg ggatcacccg gtccggcagc ttcatcgagg gcgtgcgagg | 1440 |
| gcgtgagcgc ctccgagttc ggcatccccg tctccgaggg cgcccgtcgc ctggctcgca | 1500 |
| gcttctcgca gcttcggcct cttctctccg cagacggggc agctgggcac gttgccgccg | 1560 |
| aagcagagaa ccccagagaa ccccagaggc cctggagcgc gcggcggagg cgatgcggcg | 1620 |
| gctggacagg cgggcgttcc ggggcgttcc ggggcggatt catcctggag aagatcctgg | 1680 |
| gccccgtctc ctcgggccac gtcgagctgc ggtccgctgc ggtccgccga cccgcgcgcg | 1740 |
| aacccggcgg tgacgttcaa ctacttccag gagtcggagg acctgggagg acctgcagcg | 1800 |
| gtgcgtgcgc ggcatccaga cgatcgagcg cgtgatccag tcccgggcct cgccggcct | 1860 |
| tcgccaactt cacctacgcc aacgcttcca cggagtccat cttcaccgac tccgccaact | 1920 |
| tcccccaact tccccgtcaa cctcctgccg cggcacgtca acgactcccg gacgcccgag | 1980 |

```
cagtactgca gggacctgca gggacaccgt catgaccatc tggcattacc acggcgggtg   2040
ccaggtcggc gccgtcgtgg acgaccgtgg acgacgatta ccgggtgttc ggcgtgcagc   2100
gactgagggt gatcgacagc tccacgttca agtacgttca agtactcccc cggcaccaac   2160
ccgcaggcca ccgtcatgat gctcggaagg tatatgggtg tgaaagggtg tgaaaattca   2220
ggccgagaga tggaggaaat ga                                           2242

<210> SEQ ID NO 18
<211> LENGTH: 672
<212> TYPE: PRT
<213> ORGANISM: Zea mays

<400> SEQUENCE: 18
```

Met Ala Pro Gly Leu Ala Asn Trp Val Ala Leu Val Leu Thr Val Leu
1               5                   10                  15

Leu Gly Leu Ser Cys Leu Val Val Ala Leu Ser Glu Asp Glu Thr Leu
            20                  25                  30

Asp Lys Leu Arg Phe Val Arg His Ala Gln Asp Ala Pro Leu Val Ser
        35                  40                  45

Gln Tyr Asn Tyr Ile Val Ile Gly Gly Gly Thr Ala Gly Cys Pro Leu
    50                  55                  60

Ala Ala Thr Leu Ser Glu Gly Cys Pro Leu Ala Ala Thr Leu Ser Glu
65                  70                  75                  80

His Ser Arg Val Leu Leu Glu Arg Gly Gly Leu Pro Ser Arg Asn
                85                  90                  95

Met Ser Asp Gln Gln His Phe Thr Asp Ala Leu Ala Asp Thr Ser Pro
            100                 105                 110

Ala Ser Pro Ala Gln Arg Phe Val Ser Glu Asp Gly Val Val Asn Ala
        115                 120                 125

Arg Ala Arg Val Leu Gly Gly Gly Ser Cys Leu Asn Arg Val Leu Gly
130                 135                 140

Gly Gly Ser Cys Leu Asn Ala Gly Phe Tyr Thr Arg Ala Ser Thr Asp
145                 150                 155                 160

Tyr Val Arg Ala Ala Gly Trp Asp Ala Arg Leu Val Asn Ser Ser Tyr
                165                 170                 175

Arg Trp Val Glu Arg Ala Leu Val Phe Arg Pro Ala Val Pro Pro Trp
            180                 185                 190

Gln Ala Ala Leu Arg Asp Ala Leu Leu Glu Ala Gly Val Thr Pro Asp
        195                 200                 205

Asn Gly Leu Glu Ala Gly Val Thr Pro Asp Asn Gly Phe Thr Phe Asp
    210                 215                 220

His Val Thr Gly Thr Lys Ile Gly Gly Thr Ile Phe Asp Ser Ser Gly
225                 230                 235                 240

Gln Arg His Thr Ala Ala Asp Phe Leu Arg His Ala Arg Pro Arg Gly
                245                 250                 255

Leu Thr Val Phe Leu Tyr Ala Thr Val Ser Arg Ile Leu Phe Arg Gln
            260                 265                 270

Gln Glu Gly Val Pro Tyr Pro Val Arg Gln Gln Glu Gly Val Pro Tyr
        275                 280                 285

Pro Val Ala Tyr Gly Val Phe Thr Asp Pro Leu Gly Val Gln His
    290                 295                 300

Arg Val Tyr Leu Arg Asp Gly Ala Lys Asn Glu Val Ile Leu Ser Ala
305                 310                 315                 320

Gly Thr Leu Gly Ser Pro Gln Leu Leu Met Leu Ser Gly Val Gly Pro

```
             325                 330                 335
    Gln Ala His Leu Glu Ala His Gly Val Gln Val Leu Val Asp Glu Ala
            340                 345                 350
    His Gly Val Gln Val Leu Val Asp Gln Pro Met Val Gly Gln Gly Val
            355                 360                 365
    Ala Asp Asn Pro Met Asn Ser Val Phe Ile Pro Ser Pro Val Pro Val
            370                 375                 380
    Thr Leu Ser Leu Val Gln Val Val Gly Ile Thr Arg Ser Gly Ser Phe
    385                 390                 395                 400
    Ile Glu Gly Val Ser Gly Ser Glu Phe Gly Ile Pro Val Ser Glu Gly
                        405                 410                 415
    Ala Arg Arg Leu Ile Pro Val Ser Glu Gly Ala Arg Arg Leu Ala Arg
                420                 425                 430
    Ser Phe Gly Leu Phe Ser Pro Gln Thr Gly Gln Leu Gly Thr Leu Pro
                435                 440                 445
    Pro Lys Gln Arg Thr Pro Glu Ala Leu Glu Arg Ala Ala Glu Ala Met
            450                 455                 460
    Arg Arg Leu Asp Arg Arg Ala Phe Arg Gly Gly Phe Ile Leu Glu Lys
    465                 470                 475                 480
    Ile Leu Gly Pro Val Ser Ser Gly His Val Ile Leu Gly Pro Val Ser
                        485                 490                 495
    Ser Gly His Val Glu Leu Arg Ser Ala Asp Pro Arg Ala Asn Pro Ala
                    500                 505                 510
    Val Thr Phe Asn Tyr Phe Gln Glu Ser Glu Asp Leu Gln Arg Cys Val
                515                 520                 525
    Arg Gly Ile Gln Thr Ile Glu Arg Val Ile Gln Ser Arg Ala Phe Ala
                530                 535                 540
    Asn Phe Thr Tyr Ala Asn Ala Ser Thr Glu Ser Ile Phe Thr Asp Ser
    545                 550                 555                 560
    Ala Ser Thr Glu Ser Ile Phe Thr Asp Ser Ala Asn Phe Pro Val Asn
                        565                 570                 575
    Leu Leu Pro Arg His Val Asn Asp Ser Arg Thr Pro Glu Gln Tyr Cys
                    580                 585                 590
    Arg Asp Thr Val Met Thr Ile Trp His Tyr His Gly Gly Cys Gln Val
                595                 600                 605
    Gly Ala Val Val Asp Asp Tyr Arg Val Phe Gly Val Gln Arg Leu
                610                 615                 620
    Arg Val Ile Asp Ser Ser Val Gln Arg Leu Arg Val Ile Asp Ser Ser
    625                 630                 635                 640
    Thr Phe Lys Tyr Ser Pro Gly Thr Asn Pro Gln Ala Thr Val Met Met
                        645                 650                 655
    Leu Gly Arg Tyr Met Gly Val Lys Ile Gln Ala Glu Arg Trp Arg Lys
                    660                 665                 670

<210> SEQ ID NO 19
<211> LENGTH: 1959
<212> TYPE: DNA
<213> ORGANISM: Setaria italica

<400> SEQUENCE: 19
tttgccggcg aaaatggcgc tggggcttgc gagctcggcg gcgctggttc tagccaccat    60
cctgggctcc ttgtgcctcg tcgcactctc agaggatgag caactcgaga acctgcggtt   120
cgtgcggcgc gcacaggacg cgcccctggt gtcgcactac aactacatca tcatcggcgg   180
```

| | | |
|---|---|---|
| cggcacggcg ggttgcccac tggcggcgac gctgtcggag cactcccgcg tgctgctcct | 240 | |
| ggagcgcggt ggcctcccct accgcaacat gtccaaccag cagcacttca cggacgcgct | 300 | |
| ggcggacacg tccccggcgt cgccggcgca gcggttcatc tccgaggacg cgtggtgaa | 360 | |
| cgcccgggcg cgggtgctgg gcggtggcag ctgcctcaac gccgggttct acacgcgcgc | 420 | |
| cagcaacgac tacgtgcacg ccgccgggtg ggacgcgcgc ctcgtcaact cgtcctaccg | 480 | |
| ctgggtggag cgcgcgctgg tgttccgccc cgacgttccg ccgtggcagg cggcgctccg | 540 | |
| cgacgcgctg ctcgaggccg cgtcacgcc cgacaacggg ttcaccttcg accacgtcac | 600 | |
| ggggaccaag atcgggggca ccatcttcga cagcagcggg cagcggcaca ccgccgccga | 660 | |
| cttcctccgc cacgcgcgcc ccgggggcct caccgtgctc ctctacgcca ccgtctcgag | 720 | |
| gatcctcttc aggcagcagg aggggcgcc gtaccggtg gcgtacgcg tggtgttcag | 780 | |
| cgacccgctg ggggtgcagc accgggtgta cctccaggac ggcggcaaga acgaggtgat | 840 | |
| cctatcggcg gggacgctgg ggagcccgca gctgctgatg ctgagcggcg tcgggccgca | 900 | |
| ggcgcacctg gaggcgcacg cgtccaggt gctagtggac cagcccatgg tcgggcaggg | 960 | |
| cgtggccgac aatcccatga actcggtgtt catcccgtcg cccgtgcccg tcgcgctctc | 1020 | |
| gctcgtgcag gtcgtgggga tcacccgcac cggcagcttc atcgagggcg tcagcggctc | 1080 | |
| cgagttcggc atcccagtct ccgagggcgt ccgccgcctc gctcgcaact tcggcctctt | 1140 | |
| ctctcctcag accgggcagc tcggcacgct gccgccgaag cagaggacgc cggaggcgct | 1200 | |
| gcagcgcgcg gcggaggcga tgcggcggct ggacaggcgg gcgttccggg gcggcttcat | 1260 | |
| cctggagaag atcctggggc ccgtgtcgtc gggccacatc gagctgcgct ccaccgaccc | 1320 | |
| gcgcgcgaac ccggcggtga cgttcaacta cttccaggag aaggaggacc tggaccggtg | 1380 | |
| cgtgcatggc atcgagacga tcgagcgggt catccagtcc cgggccttcg ccaatttcac | 1440 | |
| ctacgccaac gcctccgtcg agtccatctt caccgactcc gccaacttcc ccgtcaacct | 1500 | |
| gctgccgcgc cacgccaacg actcccggac gccgagcag tactgcaggg acaccgtcat | 1560 | |
| gaccatctgg cactaccacg gcggctgcca ggtcggcgcc gtcgtcgacg atgactaccg | 1620 | |
| ggtgttcggc gtgcagcggc tcagggtcat cgacagctcc accttcaagt actccccagg | 1680 | |
| caccaacccg caggccaccg tcatgatgct cggaaggtat atgggtgtga aaatccaggc | 1740 | |
| agagagatgg aggaaatgat caagaagagc aaatgatttc tgtatcgggg tacctgacta | 1800 | |
| tctgctttag agtagtttta ttttattttt ctctttactc ttctctagag atagttctag | 1860 | |
| tttccggttg ttgattccaa atccttcaca cccttgagat gcatagctca gcatttcgca | 1920 | |
| agaacagtga aaaattatgc tgcattggca tgatggaaa | 1959 | |

<210> SEQ ID NO 20
<211> LENGTH: 581
<212> TYPE: PRT
<213> ORGANISM: Setaria italica

<400> SEQUENCE: 20

Met Ala Leu Gly Leu Ala Ser Ser Ala Ala Leu Val Leu Ala Thr Ile
1               5                   10                  15

Leu Gly Ser Leu Cys Leu Val Ala Leu Ser Glu Asp Glu Gln Leu Glu
            20                  25                  30

Asn Leu Arg Phe Val Arg Arg Ala Gln Asp Ala Pro Leu Val Ser His
        35                  40                  45

Tyr Asn Tyr Ile Ile Ile Gly Gly Gly Thr Ala Gly Cys Pro Leu Ala
    50                  55                  60

-continued

```
Ala Thr Leu Ser Glu His Ser Arg Val Leu Leu Glu Arg Gly Gly
 65                  70                  75                  80

Leu Pro Tyr Arg Asn Met Ser Asn Gln Gln His Phe Thr Asp Ala Leu
                 85                  90                  95

Ala Asp Thr Ser Pro Ala Ser Pro Ala Gln Arg Phe Ile Ser Glu Asp
            100                 105                 110

Gly Val Val Asn Ala Arg Ala Arg Val Leu Gly Gly Gly Ser Cys Leu
        115                 120                 125

Asn Ala Gly Phe Tyr Thr Arg Ala Ser Asn Asp Tyr Val His Ala Ala
    130                 135                 140

Gly Trp Asp Ala Arg Leu Val Asn Ser Ser Tyr Arg Trp Val Glu Arg
145                 150                 155                 160

Ala Leu Val Phe Arg Pro Asp Val Pro Pro Trp Gln Ala Ala Leu Arg
                165                 170                 175

Asp Ala Leu Leu Glu Ala Gly Val Thr Pro Asp Asn Gly Phe Thr Phe
            180                 185                 190

Asp His Val Thr Gly Thr Lys Ile Gly Gly Thr Ile Phe Asp Ser Ser
        195                 200                 205

Gly Gln Arg His Thr Ala Ala Asp Phe Leu Arg His Ala Arg Pro Gly
    210                 215                 220

Gly Leu Thr Val Leu Leu Tyr Ala Thr Val Ser Arg Ile Leu Phe Arg
225                 230                 235                 240

Gln Gln Glu Gly Ala Pro Tyr Pro Val Ala Tyr Gly Val Val Phe Ser
                245                 250                 255

Asp Pro Leu Gly Val Gln His Arg Val Tyr Leu Gln Asp Gly Gly Lys
            260                 265                 270

Asn Glu Val Ile Leu Ser Ala Gly Thr Leu Gly Ser Pro Gln Leu Leu
        275                 280                 285

Met Leu Ser Gly Val Gly Pro Gln Ala His Leu Glu Ala His Gly Val
    290                 295                 300

Gln Val Leu Val Asp Gln Pro Met Val Gly Gln Gly Val Ala Asp Asn
305                 310                 315                 320

Pro Met Asn Ser Val Phe Ile Pro Ser Pro Val Pro Ala Leu Ser
                325                 330                 335

Leu Val Gln Val Val Gly Ile Thr Arg Thr Gly Ser Phe Ile Glu Gly
            340                 345                 350

Val Ser Gly Ser Glu Phe Gly Ile Pro Val Ser Glu Gly Val Arg Arg
        355                 360                 365

Leu Ala Arg Asn Phe Gly Leu Phe Ser Pro Gln Thr Gly Gln Leu Gly
    370                 375                 380

Thr Leu Pro Pro Lys Gln Arg Thr Pro Glu Ala Leu Gln Arg Ala Ala
385                 390                 395                 400

Glu Ala Met Arg Arg Leu Asp Arg Arg Ala Phe Arg Gly Gly Phe Ile
                405                 410                 415

Leu Glu Lys Ile Leu Gly Pro Val Ser Ser Gly His Ile Glu Leu Arg
            420                 425                 430

Ser Thr Asp Pro Arg Ala Asn Pro Ala Val Thr Phe Asn Tyr Phe Gln
        435                 440                 445

Glu Lys Glu Asp Leu Asp Arg Cys Val His Gly Ile Glu Thr Ile Glu
    450                 455                 460

Arg Val Ile Gln Ser Arg Ala Phe Ala Asn Phe Thr Tyr Ala Asn Ala
465                 470                 475                 480
```

```
Ser Val Glu Ser Ile Phe Thr Asp Ser Ala Asn Phe Pro Val Asn Leu
            485                 490                 495

Leu Pro Arg His Ala Asn Asp Ser Arg Thr Pro Glu Gln Tyr Cys Arg
        500                 505                 510

Asp Thr Val Met Thr Ile Trp His Tyr His Gly Gly Cys Gln Val Gly
        515                 520                 525

Ala Val Val Asp Asp Asp Tyr Arg Val Phe Gly Val Gln Arg Leu Arg
        530                 535                 540

Val Ile Asp Ser Ser Thr Phe Lys Tyr Ser Pro Gly Thr Asn Pro Gln
545                 550                 555                 560

Ala Thr Val Met Met Leu Gly Arg Tyr Met Gly Val Lys Ile Gln Ala
            565                 570                 575

Glu Arg Trp Arg Lys
            580

<210> SEQ ID NO 21
<211> LENGTH: 2000
<212> TYPE: DNA
<213> ORGANISM: Brachypodium distachyon

<400> SEQUENCE: 21
```

| | | | | | |
|---|---|---|---|---|---|
| atggcacttt | gccgcgcgat | ctcggcggcg | ctggtgctcg | ccgccgccgt | cttactcggc | 60 |
| tcgctctgcc | ccgtcgccct | ctcggaggac | ggtgcgtaca | tatattctgc | cttccgtgtt | 120 |
| tcttaagttg | tcacgactca | cgattaacgt | gtctcattcg | tgcgtgcaga | gcgactggag | 180 |
| aacctgcggt | tcgtgcagca | cgcatcggac | gcgccgctgg | tgtcgcactt | caactacatc | 240 |
| atcgtgggcg | ggggcacgtc | ggggtgcccg | ctggcggcga | cgctgtcgga | gcactcgcgg | 300 |
| gtgctcctcc | tggagcgggg | cgggctgccg | cacgccaaca | tgtcgagcca | ggagcacttc | 360 |
| acggacgcgc | tggcggacac | gtccccggcg | tccccggcgc | agcggttcgt | ttcggaagac | 420 |
| ggggtggtga | acgcccgcgc | cagggtgctt | ggcggaggga | gctgcctcaa | cgcgggcttc | 480 |
| tacacgcgcg | ccagcaacga | gtacgtgcgc | accgccgggt | gggaccccag | gctggtgaac | 540 |
| tcgtcctacc | gctgggtgga | gcgcgcgctc | gtgttccggc | caggcgtgcc | gccgtggcag | 600 |
| gcggctctgc | gggacgcgct | gctcgaggcc | ggcgtcacgc | cggataacgg | cttcacgttt | 660 |
| gatcatgtca | cggggaccaa | gatcggggc | accatcttcg | acggcaacgg | ccagcggcac | 720 |
| acggccgccg | acttcctacg | gcacgccagg | cccaggggcc | tcaccgtcgt | gctctacgcc | 780 |
| accgtgtcac | ggatcctctt | cagaagccaa | ggtactcttt | catgatccta | atttcatgtc | 840 |
| gaactacgca | gaaagaagta | agaacgactt | attttgtgc | cgtgacacta | ctgtagaggg | 900 |
| cgttccgtac | ccggtggcgt | acggggtggt | gttcggggac | ccgctggggg | tgcagcaccg | 960 |
| ggtgtacctc | cgtgacgggg | ccaagaacga | ggtgatcctg | gcggccggga | cgctggggag | 1020 |
| cccgcagctg | ctgatgctga | gcggcgtggg | cccgcaggcg | cacctggagg | cccacggcat | 1080 |
| ccaggccctg | gtcgaccagc | ccatggtcgg | gcagggcgtc | gccgacaacc | ccatgaactc | 1140 |
| ggtgttcatc | ccgtcgccgg | tgcccgtggg | cctctcccctg | gtgcaggtcg | tcggcatcac | 1200 |
| caagtccggc | agcttcatcg | agggcgtcag | cggctcggag | ttcggcatcc | cggtctccga | 1260 |
| cagcgcccgc | gcctcgccg | ccagcttcgg | cctcttctct | cctcagaccg | gcagctcgg | 1320 |
| cacgctgccg | cccaagcaga | ggacgcccga | ggcgctgcag | cgcgcggcgg | acgccatgcg | 1380 |
| gcggctcgac | cggcgcgcgt | tccggggcgg | cttcatcctg | gagaagatcc | tcgggccggt | 1440 |
| ctccacgggg | cacgtcgagc | tccggaccac | ggacccgagg | gccaacccgg | cggtgctgtt | 1500 |

| | |
|---|---:|
| caactacttc caggaggcgg aggacctgga gcggtgcgtg cggggatcc agacgatcga | 1560 |
| gcgtgtgatc gcgtcgcgtg ccttttcgaa cttcacctac tccaacgcct ccgtggagtc | 1620 |
| catcttcagc gactcggcga acttccccgt gaacctgctg ccgcggcacg ccaacgactc | 1680 |
| caggtcgccc gagcagtact gcagggagac cgtcatgacc atctggcact accacggcgg | 1740 |
| ctgccatgtc ggcgccgtcg tcgacgacga ttaccgggtg tttggggtaa gggggctcag | 1800 |
| ggtcatcgac agctccacct tcaggtactc ccccggcacc aacccgcagg ccaccgtcat | 1860 |
| gatgctcggc aggtaaactc gtcgaagtct gaaatgatta gttgtgttga tctgaatgac | 1920 |
| cttgagtaaa aacactagtg ttctgaatct gcacaggtat atgggagtga agattcaggc | 1980 |
| cgagagatgg aggaagtgat | 2000 |

<210> SEQ ID NO 22
<211> LENGTH: 1752
<212> TYPE: DNA
<213> ORGANISM: Brachypodium distachyon

<400> SEQUENCE: 22

| | |
|---|---:|
| atggcacttt gccgcgcgat ctcggcggcg ctggtgctcg ccgccgccgt cttactcggc | 60 |
| tcgctctgcc ccgtcgccct ctcggaggac gagcgactgg agaacctgcg gttcgtgcag | 120 |
| cacgcatcgg acgcgccgct ggtgtcgcac ttcaactaca tcatcgtggg cgggggcacg | 180 |
| tcggggtgcc cgctggcggc gacgctgtcg gagcactcgc gggtgctcct cctggagcgg | 240 |
| ggcgggctgc cgcacgccaa catgtcgagc caggagcact tcacggacgc gctggcggac | 300 |
| acgtccccgg cgtccccggc gcagcggttc gtttcggaag acggggtggt gaacgcccgc | 360 |
| gccagggtgc ttggcggagg gagctgcctc aacgcgggct tctacacgcg cgccagcaac | 420 |
| gagtacgtgc gcaccgccgg gtgggacccc aggctggtga actcgtccta ccgctgggtg | 480 |
| gagcgcgcgc tcgtgttccg gccaggcgtg ccgccgtggc aggcggctct gcgggacgcg | 540 |
| ctgctcgagg ccggcgtcac gccggataac ggcttcacgt ttgatcatgt cacggggacc | 600 |
| aagatcgggg gcaccatctt cgacggcaac ggccagcggc acacggccgc cgacttccta | 660 |
| cggcacgcca ggcccagggg cctcaccgtc gtgctctacg ccaccgtgtc acggatcctc | 720 |
| ttcagaagcc aagagggcgt tccgtacccg gtggcgtacg gggtggtgtt cggggacccg | 780 |
| ctggggtgc agcaccgggt gtacctccgt gacgggccca agaacgaggt gatcctggcg | 840 |
| gccgggacgc tggggagccc gcagctgctg atgctgagcg gcgtgggccc gcaggcgcac | 900 |
| ctggaggccc acggcatcca ggccctggtc gaccagccca tggtcgggca gggcgtcgcc | 960 |
| gacaacccca tgaactcggt gttcatcccg tcgccggtgc ccgtgggcct ctccctggtg | 1020 |
| caggtcgtcg gcatcaccaa gtccggcagc ttcatcgagg gcgtcagcgg ctcggagttc | 1080 |
| ggcatcccgg tctccgacag cgcccgccgc ctcgccgcca gcttcggcct cttctctcct | 1140 |
| cagaccgggc agctcggcac gctgccgccc aagcagagga cgcccgaggc gctgcagcgc | 1200 |
| gcggcggacg ccatgcggcg gctcgaccgg cgcgcgttcc ggggcggctt catcctggag | 1260 |
| aagatcctcg gccggtctc acggggcac gtcgagctcc ggaccacgga cccgagggcc | 1320 |
| aacccggcg tgctgttcaa ctacttccag gaggcggagg acctggagcg gtgcgtgcgg | 1380 |
| gggatccaga cgatcgagcg tgtgatcgcg tcgcgtgcct tttcgaactt cacctactcc | 1440 |
| aacgcctccg tggagtccat cttcagcgac tcggcgaact tccccgtgaa cctgctgccg | 1500 |
| cggcacgcca acgactccag gtcgcccgag cagtactgca gggagaccgt catgaccatc | 1560 |
| tggcactacc acggcggctg ccatgtcggc gccgtcgtcg acgacgatta ccgggtgttt | 1620 |

```
gggtaaggg ggctcagggt catcgacagc tccaccttca ggtactcccc cggcaccaac    1680
ccgcaggcca ccgtcatgat gctcggcagg tatatgggag tgaagattca ggccgagaga    1740
tggaggaagt ga                                                         1752
```

<210> SEQ ID NO 23
<211> LENGTH: 583
<212> TYPE: PRT
<213> ORGANISM: Brachypodium distachyon

<400> SEQUENCE: 23

```
Met Ala Leu Cys Arg Ala Ile Ser Ala Leu Val Leu Ala Ala Ala
1               5                   10                  15

Val Leu Leu Gly Ser Leu Cys Pro Val Ala Leu Ser Glu Asp Glu Arg
            20                  25                  30

Leu Glu Asn Leu Arg Phe Val Gln His Ala Ser Asp Ala Pro Leu Val
        35                  40                  45

Ser His Phe Asn Tyr Ile Ile Val Gly Gly Thr Ser Gly Cys Pro
    50                  55                  60

Leu Ala Ala Thr Leu Ser Glu His Ser Arg Val Leu Leu Leu Glu Arg
65                  70                  75                  80

Gly Gly Leu Pro His Ala Asn Met Ser Ser Gln Glu His Phe Thr Asp
                85                  90                  95

Ala Leu Ala Asp Thr Ser Pro Ala Ser Pro Ala Gln Arg Phe Val Ser
            100                 105                 110

Glu Asp Gly Val Val Asn Ala Arg Ala Arg Val Leu Gly Gly Gly Ser
        115                 120                 125

Cys Leu Asn Ala Gly Phe Tyr Thr Arg Ala Ser Asn Glu Tyr Val Arg
    130                 135                 140

Thr Ala Gly Trp Asp Pro Arg Leu Val Asn Ser Ser Tyr Arg Trp Val
145                 150                 155                 160

Glu Arg Ala Leu Val Phe Arg Pro Gly Val Pro Pro Trp Gln Ala Ala
                165                 170                 175

Leu Arg Asp Ala Leu Leu Glu Ala Gly Val Thr Pro Asp Asn Gly Phe
            180                 185                 190

Thr Phe Asp His Val Thr Gly Thr Lys Ile Gly Gly Thr Ile Phe Asp
        195                 200                 205

Gly Asn Gly Gln Arg His Thr Ala Ala Asp Phe Leu Arg His Ala Arg
    210                 215                 220

Pro Arg Gly Leu Thr Val Val Leu Tyr Ala Thr Val Ser Arg Ile Leu
225                 230                 235                 240

Phe Arg Ser Gln Glu Gly Val Pro Tyr Pro Val Ala Tyr Gly Val Val
                245                 250                 255

Phe Gly Asp Pro Leu Gly Val Gln His Arg Val Tyr Leu Arg Asp Gly
            260                 265                 270

Ala Lys Asn Glu Val Ile Leu Ala Ala Gly Thr Leu Gly Ser Pro Gln
        275                 280                 285

Leu Leu Met Leu Ser Gly Val Gly Pro Gln Ala His Leu Glu Ala His
    290                 295                 300

Gly Ile Gln Ala Leu Val Asp Gln Pro Met Val Gly Gln Gly Val Ala
305                 310                 315                 320

Asp Asn Pro Met Asn Ser Val Phe Ile Pro Ser Pro Val Pro Val Gly
                325                 330                 335

Leu Ser Leu Val Gln Val Val Gly Ile Thr Lys Ser Gly Ser Phe Ile
```

```
            340                 345                 350
Glu Gly Val Ser Gly Ser Glu Phe Gly Ile Pro Val Ser Asp Ser Ala
            355                 360                 365
Arg Arg Leu Ala Ala Ser Phe Gly Leu Phe Ser Pro Gln Thr Gly Gln
        370                 375                 380
Leu Gly Thr Leu Pro Pro Lys Gln Arg Thr Pro Glu Ala Leu Gln Arg
385                 390                 395                 400
Ala Ala Asp Ala Met Arg Arg Leu Asp Arg Arg Ala Phe Arg Gly Gly
                405                 410                 415
Phe Ile Leu Glu Lys Ile Leu Gly Pro Val Ser Thr Gly His Val Glu
            420                 425                 430
Leu Arg Thr Thr Asp Pro Arg Ala Asn Pro Ala Val Leu Phe Asn Tyr
        435                 440                 445
Phe Gln Glu Ala Glu Asp Leu Glu Arg Cys Val Arg Gly Ile Gln Thr
    450                 455                 460
Ile Glu Arg Val Ile Ala Ser Arg Ala Phe Ser Asn Phe Thr Tyr Ser
465                 470                 475                 480
Asn Ala Ser Val Glu Ser Ile Phe Ser Asp Ser Ala Asn Phe Pro Val
                485                 490                 495
Asn Leu Leu Pro Arg His Ala Asn Asp Ser Arg Ser Pro Glu Gln Tyr
            500                 505                 510
Cys Arg Glu Thr Val Met Thr Ile Trp His Tyr His Gly Gly Cys His
        515                 520                 525
Val Gly Ala Val Val Asp Asp Asp Tyr Arg Val Phe Gly Val Arg Gly
    530                 535                 540
Leu Arg Val Ile Asp Ser Ser Thr Phe Arg Tyr Ser Pro Gly Thr Asn
545                 550                 555                 560
Pro Gln Ala Thr Val Met Met Leu Gly Arg Tyr Met Gly Val Lys Ile
                565                 570                 575
Gln Ala Glu Arg Trp Arg Lys
            580

<210> SEQ ID NO 24
<211> LENGTH: 678
<212> TYPE: DNA
<213> ORGANISM: artificial
<220> FEATURE:
<223> OTHER INFORMATION: synthetic

<400> SEQUENCE: 24
atggcctcct ccgagaacgt gatcaccgag ttcatgcgct tcaaggtgcg catggagggc      60
accgtgaacg ccacgagtt cgagatcgag ggcgagggcg agggccgccc ctacgagggc     120
cacaacaccg tgaagctgaa ggtgaccaag ggcggccccc tgcccttcgc ctgggacatc     180 ctgtccccc agttccagta cggctccaag gtgtacgtga agcaccccgc cgacatcccc     240
gactacaaga gctgtccctt ccccgagggc ttcaagtggg agcgcgtgat gaacttcgag     300
gacggcggcg tggccaccgt gacccaggac tcctccctgc aggacggctg cttcatctac     360
aaggtgaagt tcatcggcgt gaacttcccc tccgacggcc ccgtgatgca gaagaagacc     420
atgggctggg aggcctccac cgagcgcctg taccccgcg acggcgtgct gaagggcgag     480
acccacaagg ccctgaagct gaaggacggc ggccactacc tggtggagtt caagtccatc     540
tacatggcca agaagcccgt gcagctgccc ggctactact acgtgacgc caagctggac     600 atcacctccc acaacgagga ctacaccatc gtggagcagt acgagcgcac cgagggccgc     660
```

| | |
|---|---|
| caccacctgt tcctgtag | 678 |

<210> SEQ ID NO 25
<211> LENGTH: 812
<212> TYPE: DNA
<213> ORGANISM: Hordeum vulgare
<400> SEQUENCE: 25

| | |
|---|---|
| aaccgtctct tcgtgagaat aaccgtggcc taaaaataag ccgatgagga taaataaaat | 60 |
| gtggtggtac agtacttcaa gaggtttact catcaagagg atgcttttcc gatgagctct | 120 |
| agtagtacat cggacctcac atacctccat tgtggtgaaa tattttgtgc tcatttagtg | 180 |
| atgggtaaat tttgtttatg tcactctagg ttttgacatt tcagttttgc cactcttagg | 240 |
| ttttgacaaa taatttccat tccgcggcaa aagcaaaaca attttatttt acttttacca | 300 |
| ctcttagctt tcacaatgta tcacaaatgc cactctagaa attctgttta tgccacagaa | 360 |
| tgtgaaaaaa aacactcact tatttgaagc caaggtgttc atggcatgga aatgtgacat | 420 |
| aaagtaacgt tcgtgtataa gaaaaaattg tactcctcgt aacaagagac ggaaacatca | 480 |
| tgagacaatc gcgtttggaa ggctttgcat cacctttgga tgatgcgcat gaatggagtc | 540 |
| gtctgcttgc tagccttcgc ctaccgccca ctgagtccgg gcggcaacta ccatcggcga | 600 |
| acgacccagc tgacctctac cgaccggact tgaatgcgct accttcgtca gcgacgatgg | 660 |
| ccgcgtacgc tggcgacgtg ccccgcatg catggcggca catggcgagc tcagaccgtg | 720 |
| cgtggctggc tacaaatacg taccccgtga gtgccctagc tagaaactta cacctgcaac | 780 |
| tgcgagagcg agcgtgtgag tgtagccgag ta | 812 |

<210> SEQ ID NO 26
<211> LENGTH: 349
<212> TYPE: DNA
<213> ORGANISM: Solanum tuberosum
<400> SEQUENCE: 26

| | |
|---|---|
| ttcgaacgcg taggtaccac atggttaacc tagacttgtc catcttctgg attggccaac | 60 |
| ttaattaatg tatgaaataa aaggatgcac acatagtgac atgctaatca ctataatgtg | 120 |
| ggcatcaaag ttgtgtgtta tgtgtaatta ctagttatct gaataaaaga gaaagagatc | 180 |
| atccatatt cttatcctaa atgaatgtca cgtgtctta taattctttg atgaaccaga | 240 |
| tgcatttcat taaccaaatc catatacata taaatattaa tcatatataa ttaatatcaa | 300 |
| ttgggttagc aaaacaaatc tagtctaggt gtgttttgcg aatgcggcc | 349 |

<210> SEQ ID NO 27
<211> LENGTH: 2023
<212> TYPE: DNA
<213> ORGANISM: Oryza sativa Indica
<400> SEQUENCE: 27

| | |
|---|---|
| atggcagcac ttggccgcgc gagctcgtcg gcgccggtgc ttgccgccgc cgccgccgcc | 60 |
| gccgtgctcc tctcgctctg cctcgccgcg ctctcggaag agcaaggtgc gtaaacgttg | 120 |
| cgttgtatct ttgcgttgat gcgtgttgcg tcgtcgtcgt gttcatggcg tgcgatggcg | 180 |
| ttgtgcagag caactggaga acctgcggtt cgtgcggcac gcgcaggacg cgccgctggt | 240 |
| gtcgagctac aactacatcg tcatcggcgg cggcacggcg gggtgcccgc tggcggcgac | 300 |
| gctgtcggag cactcgcgcg tgctgctgct ggagcgcggc ggcctgccgt acgccaacat | 360 |
| gtcgagcgag cagcacttca cggacgcgct ggccgacacg tcgccggcgt cgccggcgca | 420 |

-continued

```
gcggttcatc tcggaggacg gcgtggtgaa cgcccgggcg cgggtgctcg gcggcgggag      480
ctgcctcaac gccgggttct acacgcgggc gagcaacgag tacgtgcgcg ccgccgggtg      540
ggacgcgcgg ctggtgaact cgtcgtaccg gtgggtggag cgctcgctgg tgttccgccc      600
cgacgtgccg ccgtggcagg cggcgctccg cgacgcgctg ctcgaggtcg cgtcacgcc       660 cgacaacggc ttcaccttcg accacgtcac cggcaccaag atcggcggca ccatcttcga      720
caactccggc cagcgccaca ccgccgccga cttcctccgc cacgcccgcc ccgcggcct       780 caccgtcctc ctctacgcca ccgtctcccg tatcctcttc aaaagccaag gtacacagct      840
acgatgaaaa tggaaaatgt gctgtgcgcc gaagaagctt gacctcacga cggcgagctt      900
ttgccatggc gtgcagacgg ggtgccgtac ccggtggcgt acggggtggt gttctcggac      960
ccgctggggg tgcagcaccg ggtgtacctc gcgacggcg acaagaacga ggtgatcgtg      1020
tcggcgggga cgctggggag cccgcagctg ctgatgctga gcggcgtcgg gccgcaggcg      1080
cacctggagg cgcacggcat cgaggtgatc gtggaccaac ccatggtcgg gcagggcgtc      1140
gccgacaacc cgatgaactc ggtgttcatc ccgtcgccgg tgccggtgga gctctccctg      1200
gtgcaggtcg tcggcatcac ccgctccggc agcttcatcg agggggtgag cgggtcggag      1260
ttcggcatgc cggtgtcgga cggcgcgctc cggtgggcgc gcagcttcgg gatgctgtcg      1320
ccgcagacgg ggcagctcgg cacgctgccg ccgaagcaga ggacgccgga ggcgctgcag      1380
cgggcggcgg aggcgatgat gcggctggac aggagggcgt tccggggagg cttcatcctg      1440
gagaagatcc tcgggccggt gtcctccggc cacgtcgagc tgcgaaccac cgacccgagg      1500
gcgaacccgt cggtgacgtt caactacttc cgcgaggcgg aggatctgga gcggtgcgtc      1560
catggcatcg agacgatcga gcgggtgatc cagtcgcggg ccttctccaa cttcacctac      1620
gccaacgcct ccgtcgagtc catcttcacc gattccgcca acttccccgt caacctgctg      1680
ccgcgccatg tcaacgactc gcgctcgccg gagcagtact gcatggacac cgtcatgacc      1740
atctggcact accacggcgg ctgccatgtc ggcgccgtcg tcgacgacga ttaccgggtg      1800
ttcggggtgc aggggctcag ggtgatcgac agctccacct tcaagtactc ccccggcacc      1860
aaccctcagg ccaccgtcat gatgctcggc aggtaactgg catcatttta gctcatgaaa      1920
gtgcattgcc atgagtaaca acacactaac agtatagttt tcaatatgga cactgggcag      1980
gtatatgggt gtgaagattc agtccgagag atggaagaaa tga                       2023
```

<210> SEQ ID NO 28
<211> LENGTH: 497
<212> TYPE: DNA
<213> ORGANISM: Oryza sativa Indica

<400> SEQUENCE: 28

```
tgaacaaaag ataatttcgt ttcaggagca aaaaaatgca tgtaattcaa ggaaaagaaa       60
atgttcaact gtctttagag tttagagtag atttttatttg cacccactta atttttactc     120
ttctctagac ataggttcag tatctgcttg ttgattatgt aaccttgaag aagcattgca     180
aaaacaaagc ggaaacttat gttaccaagg gcatgacgaa gaaataaatg gattagattt     240
cattgacact tagaaaatgg aaccagcaaa tcaaggctga aaataattac actagaaact     300
tattttaatg gctttacatg tcgctacata cttaaatcaa tcaaagttgc taccaaagcc     360
atgttcccta acagagggt tccgggctct caaacattct taatcttcta tacattgata     420
aaaagtatac ataaaaagaa aacctattaa gatggaaatg ttgaattctc ttaagaaagg     480
```

| | |
|---|---|
| cataaaaaat gcagggt | 497 |

<210> SEQ ID NO 29
<211> LENGTH: 1488
<212> TYPE: DNA
<213> ORGANISM: Zea mays

<400> SEQUENCE: 29

| | |
|---|---|
| atggcggcga caatggcagt gacgacgatg gtgacgagga gcaaggagag ctggtcgtca | 60 |
| ttgcaggtcc cggcggtggc attcccttgg aagccacgag gtggcaagac cggcggcctc | 120 |
| gagttccctc gccgggcgat gttcgccagc gtcggcctca acgtgtgccc gggcgtcccg | 180 |
| gcggggcgcg acccgcggga gcccgatccc aaggtcgtcc gggcggcctg cggcctggtc | 240 |
| caggcacaag tcctcttcca ggggtttaac tgggagtcgt gcaagcagca gggaggctgg | 300 |
| tacaacaggc tcaaggccca ggtcgacgac atcgccaagg ccggcgtcac gcacgtctgg | 360 |
| ctgcctccac cctcgcactc cgtctcgcca caaggctaca tgccaggccg cctatacgac | 420 |
| ctggacgcgt ccaagtacgg cacggcggcg gagctcaagt ccctgatagc ggcgttccac | 480 |
| ggcaggggcg tgcagtgcgt ggcggacatc gtcatcaacc accggtgcgc ggaaaagaag | 540 |
| gacgcgcgcg gcgtgtactg catcttcgag ggcgggactc ccgacgaccg cctggactgg | 600 |
| ggccccggga tgatctgcag cgacgacacg cagtactcgg acgggacggg gcaccgcgac | 660 |
| acgggcgagg ggttcgcggc ggcgcccgac atcgaccacc tcaacccgcg cgtgcagcgg | 720 |
| gagctctccg cctggctcaa ctggctcagg tccgacgccg tggggttcga cggctggcgc | 780 |
| ctcgacttcg ccaagggcta ctcgccgccc gtcgccagaa tgtacgtgga gcacgggg | 840 |
| ccgccgagct cgtcgtcgc ggagatatgg aactcgctga gctacagcgg ggacggcaag | 900 |
| ccggcgccca accaggacca gtgccggcag gagctgctgg actggacgcg ggccgtcggc | 960 |
| gggcccgcca tggcgttcga cttccccacc aagggcctgc tgcaggcggg cgtgcagggg | 1020 |
| gagctgtggc ggctgcgcga cagctccggc aacgcggccg gcctgatcgg gtgggcgccc | 1080 |
| gagaaggccg tcaccttcgt cgacaaccat gacaccgggt cgacgcagaa gctctggccg | 1140 |
| ttcccatccg acaaggtcat gcagggctac gcctacatcc tcacccatcc aggagtcccc | 1200 |
| tgcattttct acgaccacat gttcgactgg aacctgaagc aggagatatc cacgctgtct | 1260 |
| gccatcaggg cgcggaacgg catccgcgcc gggagcaagc tgcggatcct cgtggcggac | 1320 |
| gcggacgcgt acgtggccgt cgtcgacgag aaggtcatgg tgaagatcgg gacaaggtac | 1380 |
| ggcgtgagca gcgtggtccc gtcggatttc caccggcgg cgcacggcaa ggactactgc | 1440 |
| gtctgggaga agcgagcct ccgcgtcccg gcggggcgcc acctctag | 1488 |

<210> SEQ ID NO 30
<211> LENGTH: 2737
<212> TYPE: DNA
<213> ORGANISM: Zea mays

<400> SEQUENCE: 30

| | |
|---|---|
| tgcaccggac actgtctggt ggcataccag acagtccggt gtgccagatc agggcaccct | 60 |
| tcggttcctt tgctcctttg cttttgaacc ctaactttga tcgttattg gtttgtgttg | 120 |
| aacctttatg cacctgtgga atatataatc tagaacaaac tagttagtcc aatcatttgt | 180 |
| gttgggcatt caaccaccaa aattattat aggaaaaggt taaacctat ttcccttca | 240 |
| atctcccct ttttggtgat tgatgccaac acaaaccaaa gaaatatat aagtgcagaa | 300 |
| ttgaactagt ttgcataagg taagtgcata ggttacttag aattaaatca atttatactt | 360 |

```
ttacttgata tgcatggttg ctttcttttta ttttaacatt ttggaccaca tttgcaccac    420
ttgttttgtt ttttgcaaat cttttttggaa attcttttttc aaagtctttt gcaaatagtc    480
aaaggtatat gaataagatt gtaagaagca ttttcaagat ttgaaatttc tcccctgtt     540 tcaaatgctt ttcctttgac taaacaaaac tcccctgaa taaaattctc ctcttagctt     600
tcaagagggt tttaaataga tatcaattgg aaatatattt agatgctaat tttgaaaata    660
taccaattga aaatcaacat accaatttga aattaaacat accaatttaa aaaatttcaa    720
aaagtggtgg tgcggtcctt ttgctttggg cttaatattt ctccccttt ggcattaatc     780 gccaaaaacg gagactttgt gagccattta tactttctcc ccattggtaa atgaaatatg    840
agtgaaagat tataccaaat ttggacagtg atgcggagtg acggcgaagg ataaacgata    900
ccgttagagt ggagtggaag ccttgtcttc gccgaagact ccatttccct ttcaatctac    960
gacttagcat agaaatacac ttgaaaacac attagtcgta gccacgaaag agatatgatc   1020
aaaggtatac aaatgagcta tgtgtgtaat gtttcaatca aagttcgag atcaagaat   1080 atttagctca ttcctaagtt tgctaaaggt tttatcatct aatggtttgg taaagatatc    1140
gactaattgt tctttggtgc taacataagc aatctcgata tcacccctttt gttggtgatc    1200 cctcaaaaag tgataccgaa tgtctatgtg cttagtgcgg ctgtgttcaa cgggattatc    1260
cgccatgcag atagcactct cattgtcaca taggagaggg actttgctca atttgtagcc    1320
atagtcccta aggttttgcc tcatccaaag taattgcaca caacaatgtc ctgcggcaat    1380
atacttggct tcggcggtag aaagagctat tgagttttgt ttctttgaag tccaagacac    1440
cagggatctc cctagaaact gacaagtccc tgatgtgctc ttcctatcaa ttttacaccc    1500
tgcccaatcg gcatctgaat atcctattaa atcaaaggtg gatcccttgg ggtaccaaag    1560
accaaattta ggagtgtaaa ctaaatatct catgattctt ttcacggccc taaggtgaac    1620
ttccttagga tcggcttgga atcttgcaca catgcatata gaaagcatac tatctggtcg    1680
agatgcacat aaatagagta aagatcctat catcgaccgg tataccttt ggtctacgga    1740 tttacctccc gtgtcgaggt cgagatgccc attagttccc atgggtgtcc tgatgggctt    1800
ggcatccttc attccaaact tgttgagtat gtcttgaatg tactttgttt ggctgatgaa    1860
ggtgccatct tggagttgct tgacttgaaa tcctagaaaa tatttcaact tccccatcat    1920
agacatctcg aatttcggaa tcatgatcct actaaactct tcacaagtag atttgttagt    1980
agacccaaat ataatatcat caacataaat ttggcataca aacaaaactt tgaaatggt    2040 tttagtaaag agagtaggat cggctttact gactctgaag ccattagtga taagaaaatc    2100
tcttaggcat tcataccatg ctgttggggc ttgcttgagc ccataaagcg cctttgagag    2160
tttataaaca tggttagggt actcactatc ttcaaagccg agaggttgct caacatagac    2220
ctattcaccc catttgatca cttttttggt ccttcaggat ctaatagtta tgtataattt    2280
agagtctctt gttaatggc cagatatttc taattaatct aagaatttat gatatttttt    2340 aatttttttat catgtctgat gagaattaac ataaaggctc aattgggtcc tgaattaata    2400
atagagtgaa aattaatcca gaggctctat tagaaccttc aattagtaat accaagatat    2460
atataagata gtagagtata gtttaaatgt tggcattgtt cattctttct tttgttattt    2520
aatttatgct ttccacggtg gttagtggtt acttctgaag ggtccaaata atgcatgaag    2580
agtttgagga caagaagtct gccctaaaaa tagcgatgca aaggcatggt gtccaagcca    2640
tacatatagc gcactaattt tatcagcaga acaatggtat ttataggtcc tagtgcccag    2700
```
gcaacaagag acacgaataa agcatcgatc acgacac    2737

<210> SEQ ID NO 31
<211> LENGTH: 225
<212> TYPE: DNA
<213> ORGANISM: Zea mays

<400> SEQUENCE: 31
atggcggcga caatggcagt gacgacgatg gtgacgagga gcaaggagag ctggtcgtca    60
ttgcaggtcc cggcggtggc attcccttgg aagccacgag gtggcaagac cggcggcctc    120
gagttccctc gccgggcgat gttcgccagc gtcggcctca acgtgtgccc gggcgtcccg    180
gcggggcgcg acccgcggga gcccgatccc aaggtcgtcc gggcg    225

<210> SEQ ID NO 32
<211> LENGTH: 348
<212> TYPE: DNA
<213> ORGANISM: Zea mays

<400> SEQUENCE: 32
gatctgacaa agcagcatta gtccgttgat cggtggaaga ccactcgtca gtgttgagtt    60
gaatgtttga tcaataaaat acggcaatgc tgtaagggtt gttttttatg ccattgataa    120
tacactgtac tgttcagttg ttgaactcta tttcttagcc atgccaagtg cttttcttat    180
tttgaataac attacagcaa aaagttgaaa gacaaaaaaa aaaaccccg aacagagtgc    240
tttgggtccc aagctacttt agactgtgtt cggcgttccc cctaaatttc tcccctata    300
tctcactcac ttgtcacatc agcgttctct ttcccctata tctccacg    348

<210> SEQ ID NO 33
<211> LENGTH: 20
<212> TYPE: DNA
<213> ORGANISM: artificial
<220> FEATURE:
<223> OTHER INFORMATION: synthetic

<400> SEQUENCE: 33
gcctcaccgt cctcctctac    20

<210> SEQ ID NO 34
<211> LENGTH: 18
<212> TYPE: DNA
<213> ORGANISM: artificial
<220> FEATURE:
<223> OTHER INFORMATION: synthetic

<400> SEQUENCE: 34
cgggtccgag aacaccac    18

<210> SEQ ID NO 35
<211> LENGTH: 20
<212> TYPE: DNA
<213> ORGANISM: artificial
<220> FEATURE:
<223> OTHER INFORMATION: synthetic

<400> SEQUENCE: 35
gctatgtacg tcgccatcca    20

<210> SEQ ID NO 36
<211> LENGTH: 21
<212> TYPE: DNA
<213> ORGANISM: artificial

```
<220> FEATURE:
<223> OTHER INFORMATION: synthetic

<400> SEQUENCE: 36
ggacagtgtg gctgacacca t                                              21

<210> SEQ ID NO 37
<211> LENGTH: 25
<212> TYPE: DNA
<213> ORGANISM: artificial
<220> FEATURE:
<223> OTHER INFORMATION: synthetic

<400> SEQUENCE: 37
ggatccggat tcgaggatc aagct                                           25

<210> SEQ ID NO 38
<211> LENGTH: 25
<212> TYPE: DNA
<213> ORGANISM: artificial
<220> FEATURE:
<223> OTHER INFORMATION: synthetic

<400> SEQUENCE: 38
gtcgactttc gccgggcaaa ttcgc                                          25

<210> SEQ ID NO 39
<211> LENGTH: 27
<212> TYPE: DNA
<213> ORGANISM: artificial
<220> FEATURE:
<223> OTHER INFORMATION: synthetic

<400> SEQUENCE: 39
gtttaaacgg atttcgagga tcaagct                                        27

<210> SEQ ID NO 40
<211> LENGTH: 25
<212> TYPE: DNA
<213> ORGANISM: artificial
<220> FEATURE:
<223> OTHER INFORMATION: synthetic

<400> SEQUENCE: 40
ggatccaccc tgcatttttt atgcc                                          25

<210> SEQ ID NO 41
<211> LENGTH: 16
<212> TYPE: DNA
<213> ORGANISM: artificial
<220> FEATURE:
<223> OTHER INFORMATION: synthetic

<400> SEQUENCE: 41
gcgtcgccga caaccc                                                    16

<210> SEQ ID NO 42
<211> LENGTH: 17
<212> TYPE: DNA
<213> ORGANISM: artificial
<220> FEATURE:
<223> OTHER INFORMATION: synthetic

<400> SEQUENCE: 42
tggagaaggc ccgcgac                                                   17
```